United States Patent
Hofferberth et al.

(10) Patent No.: US 10,966,826 B2
(45) Date of Patent: Apr. 6, 2021

(54) GEOMETRICALLY-ACCOMMODATING HEART VALVE REPLACEMENT DEVICE

(71) Applicants: Children's Medical Center Corporation, Boston, MA (US); President and Fellows of Harvard College, Cambridge, MA (US); Massachusetts Institute of Technology, Cambridge, MA (US)

(72) Inventors: Sophie-Charlotte Hofferberth, Boston, MA (US); Pedro J. del Nido, Lexington, MA (US); Elazer R. Edelman, Brookline, MA (US); Peter E. Hammer, Needham, MA (US); Christopher Payne, Cambridge, MA (US)

(73) Assignees: Children's Medical Center Corporation, Boston, MA (US); President and Fellows of Harvard College, Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/764,763

(22) PCT Filed: Nov. 16, 2018

(86) PCT No.: PCT/US2018/061569
§ 371 (c)(1),
(2) Date: May 15, 2020

(87) PCT Pub. No.: WO2019/099864
PCT Pub. Date: May 23, 2019

(65) Prior Publication Data
US 2020/0368017 A1 Nov. 26, 2020

Related U.S. Application Data

(60) Provisional application No. 62/587,369, filed on Nov. 16, 2017.

(51) Int. Cl.
A61F 2/24 (2006.01)

(52) U.S. Cl.
CPC .......... *A61F 2/2418* (2013.01); *A61F 2/2433* (2013.01); *A61F 2210/0004* (2013.01);
(Continued)

(58) Field of Classification Search
CPC ......... A61F 2/24; A61F 2/2412; A61F 2/2418
(Continued)

(56) References Cited

U.S. PATENT DOCUMENTS

| | | | | |
|---|---|---|---|---|
| 2004/0260389 A1* | 12/2004 | Case | .............. | A61F 2/2475 623/1.24 |
| 2005/0075584 A1* | 4/2005 | Cali | .............. | A61F 2/2418 600/587 |

(Continued)

OTHER PUBLICATIONS

International Preliminary Report on Patentability dated May 28, 2020 in connection with International Application No. PCT/US2018/061569.
(Continued)

*Primary Examiner* — Suzette J Gherbi
(74) *Attorney, Agent, or Firm* — Wolf, Greenfield & Sacks, P.C.

(57) ABSTRACT

A replacement heart valve device is disclosed. In some embodiments, the device includes a frame coupled to one or more leaflets that are moveable between open and closed configurations. In some embodiments, the frame comprises at least two frame sections that join at a pair of commissural posts. In some embodiments, the device may be geometrically accommodating to adapt to different vasculature (Continued)

shapes and sizes and/or to be able to change size while implanted within a growing patient.

21 Claims, 40 Drawing Sheets

(52) U.S. Cl.
CPC .............. *A61F 2210/0014* (2013.01); *A61F 2230/0006* (2013.01); *A61F 2230/0008* (2013.01); *A61F 2230/0013* (2013.01); *A61F 2250/0004* (2013.01); *A61F 2250/0065* (2013.01); *A61F 2250/0082* (2013.01)

(58) Field of Classification Search
USPC ................................................ 623/2.1–2.19
See application file for complete search history.

(56) References Cited

U.S. PATENT DOCUMENTS

| | | | |
|---|---|---|---|
| 2009/0054973 A1 | 2/2009 | Johnson | |
| 2011/0098802 A1* | 4/2011 | Braido | A61F 2/2433 |
| | | | 623/1.26 |
| 2012/0101571 A1 | 4/2012 | Thambar et al. | |
| 2016/0158013 A1 | 6/2016 | Carpentier et al. | |
| 2017/0014228 A1 | 1/2017 | Emani et al. | |

OTHER PUBLICATIONS

International Search Report and Written Opinion for International Application No. PCT/US2018/061569, dated Feb. 4, 2019.

\* cited by examiner

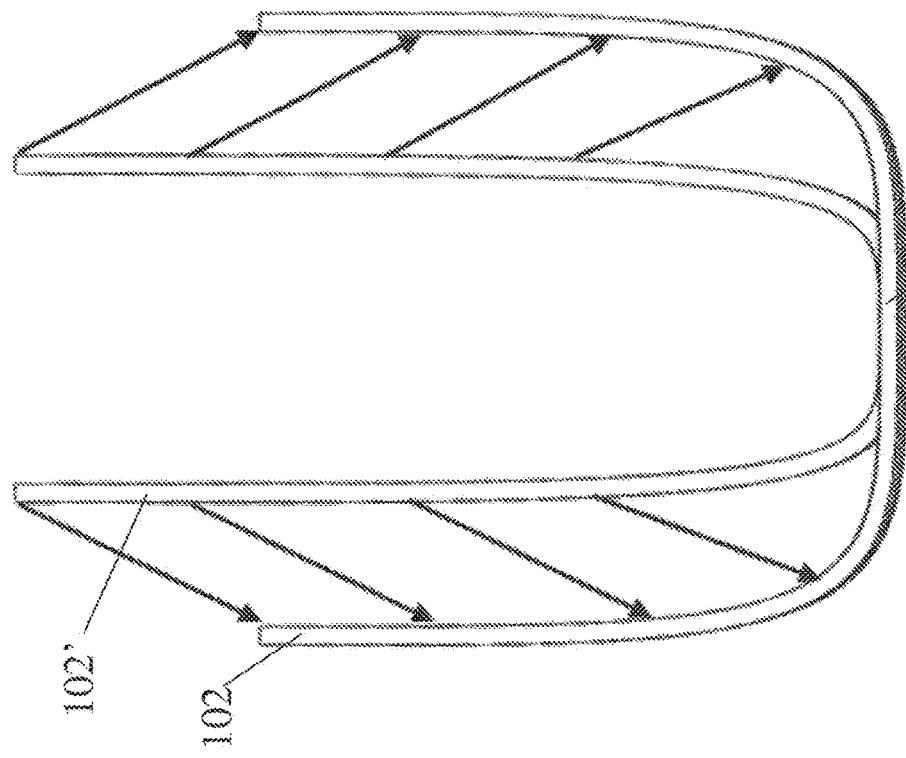
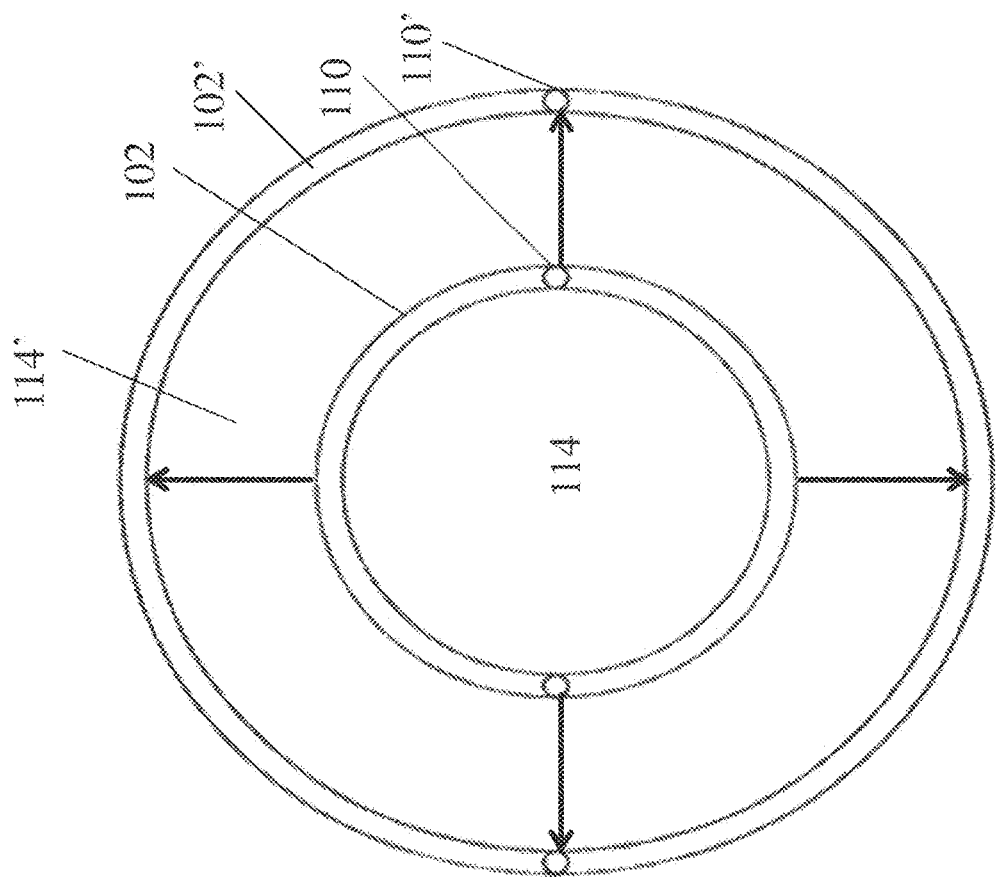
Fig. 4
Fig. 3

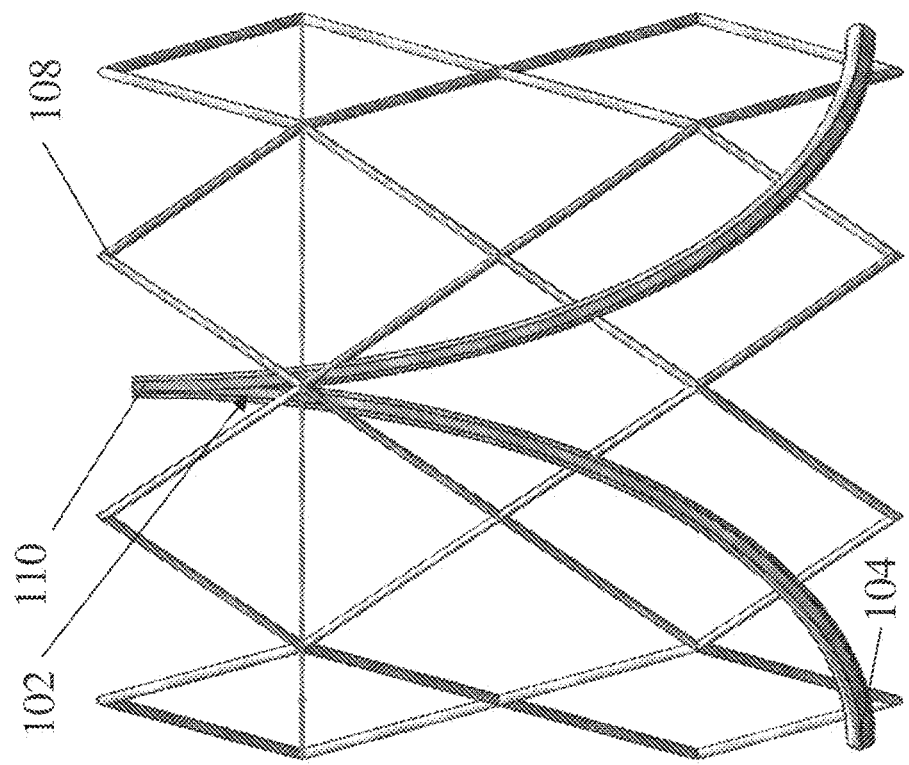
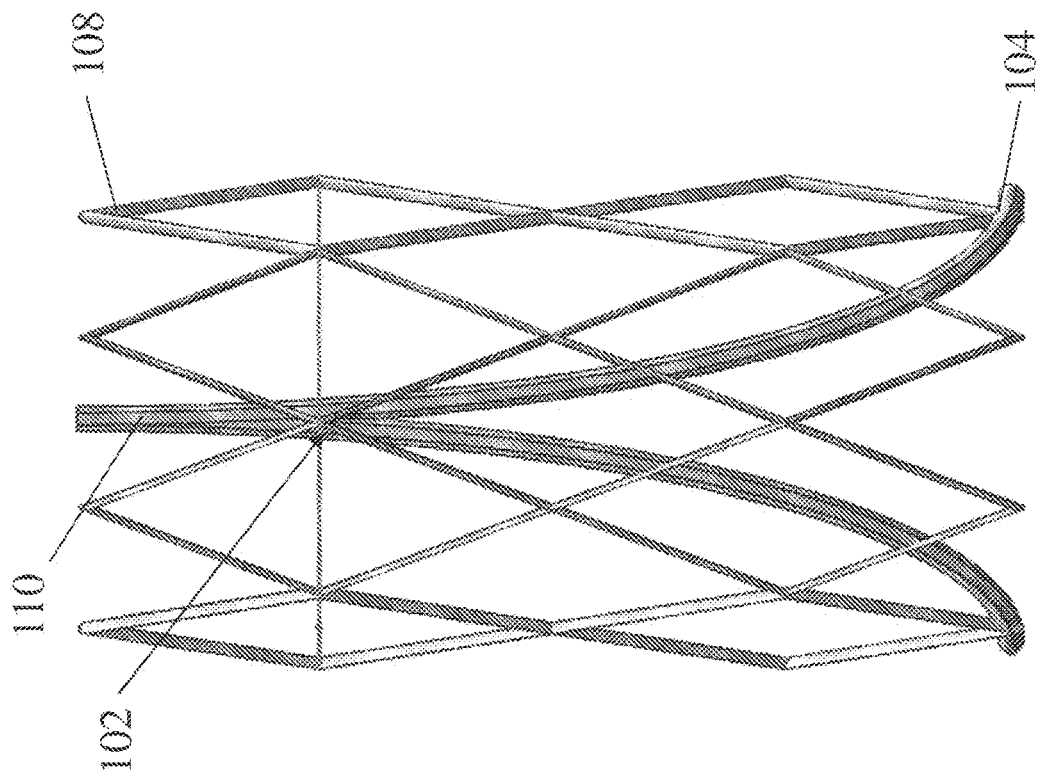

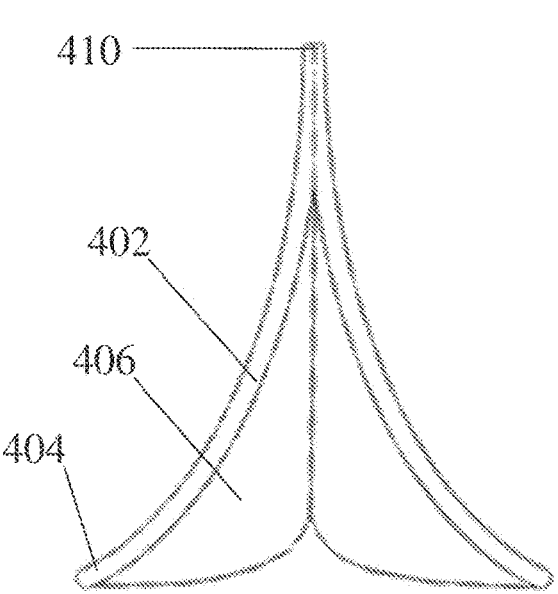
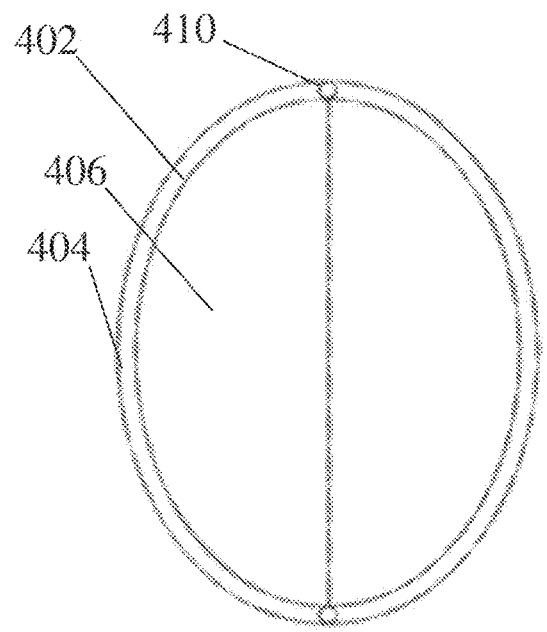
Fig. 14A    Fig. 14B
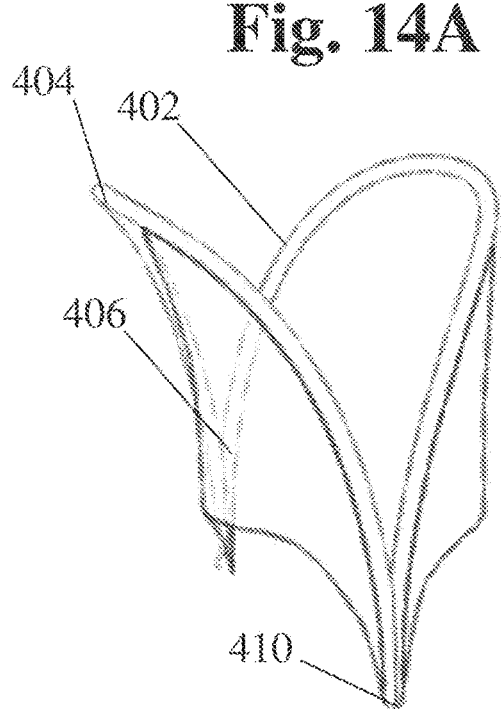
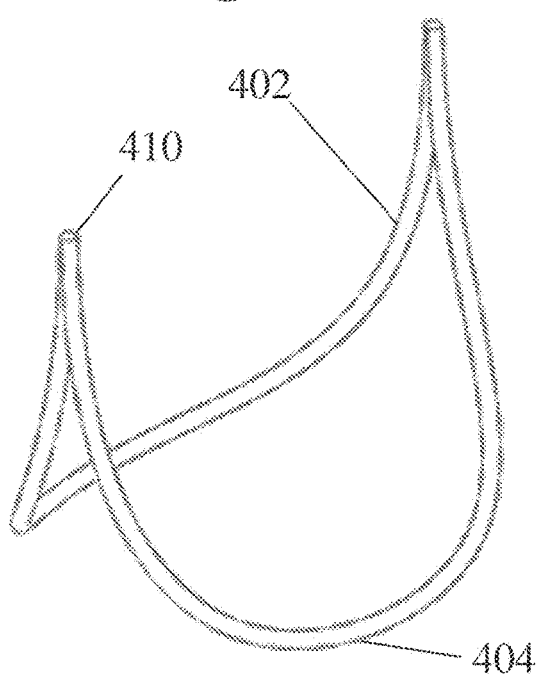
Fig. 14C    Fig. 14D

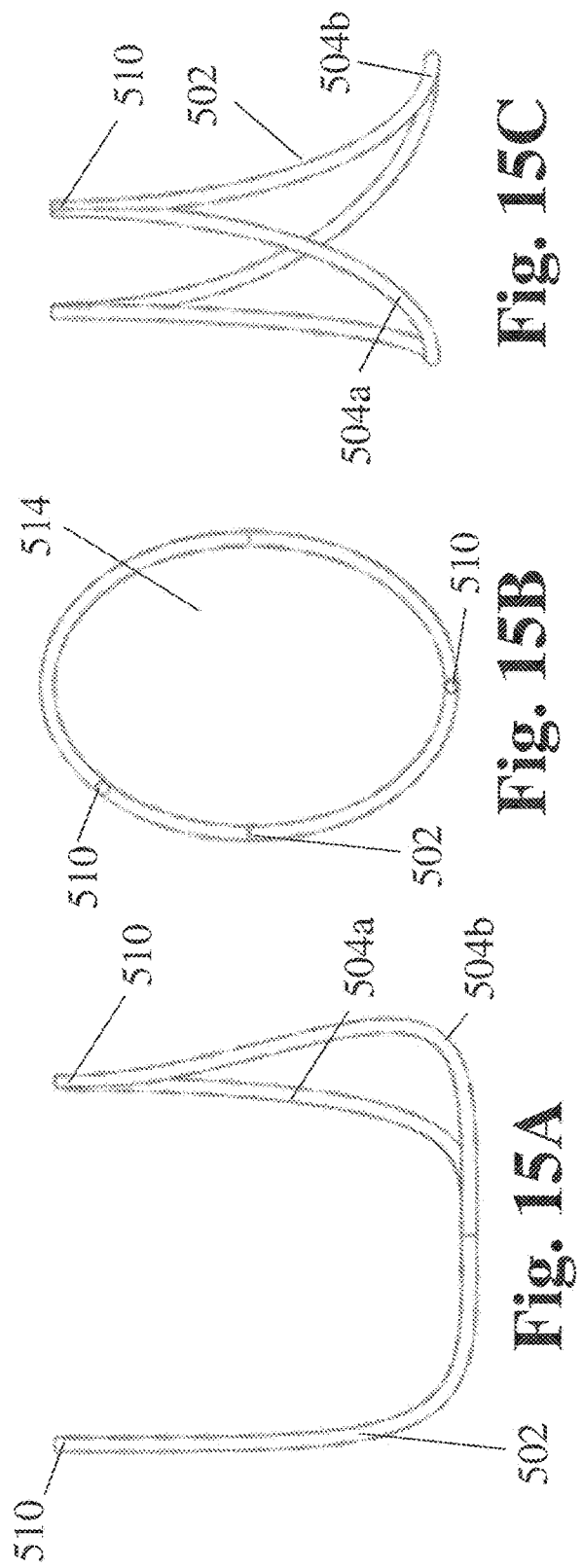

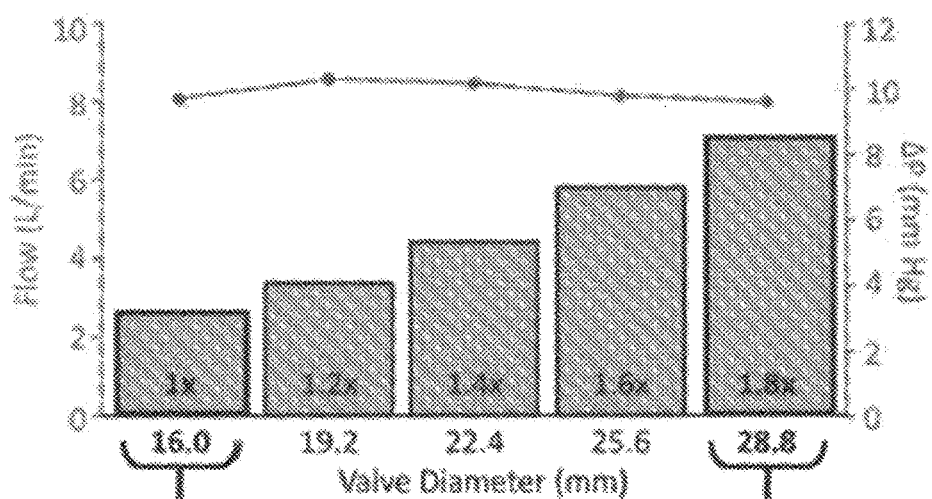
Fig. 23A
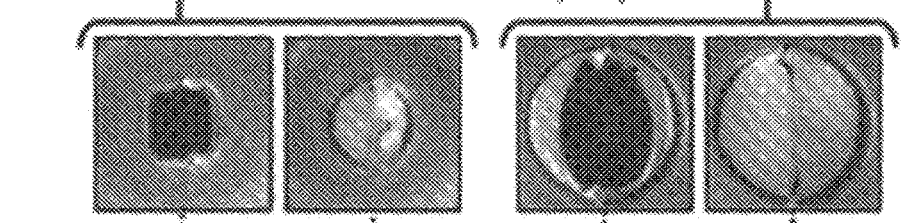
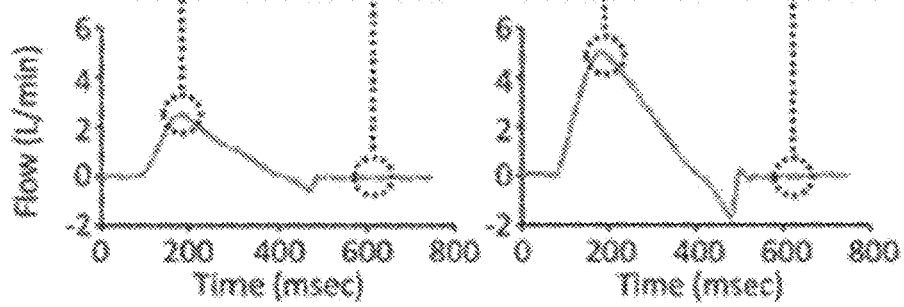
Fig. 23B

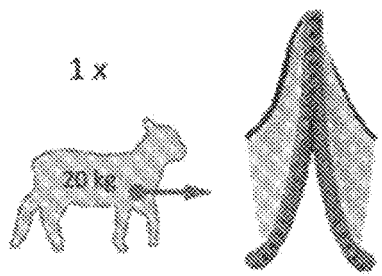 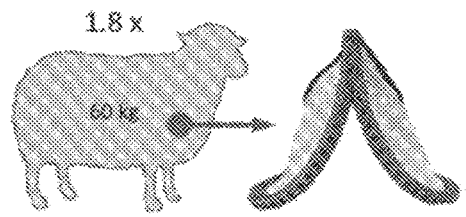
Fig. 24A  Fig. 24B
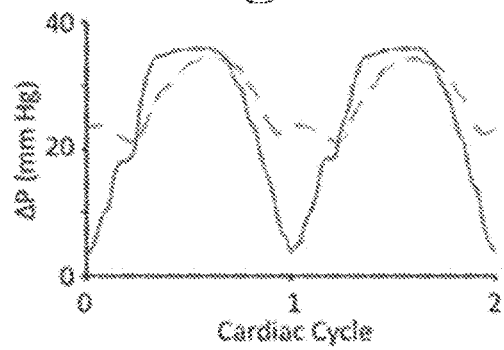 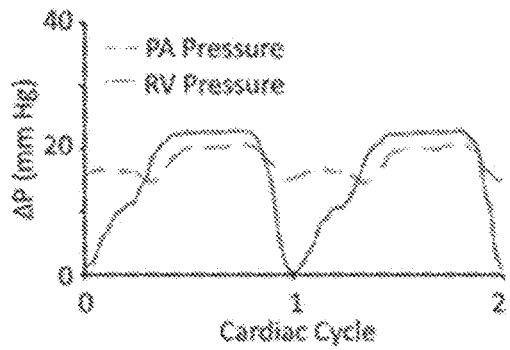
Fig. 24C  Fig. 24D
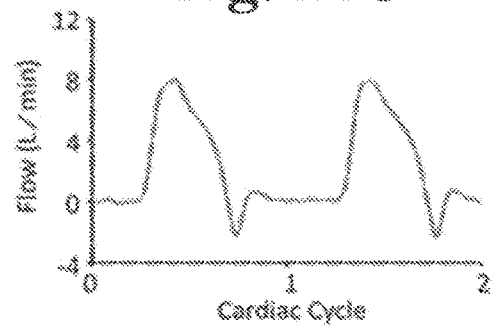 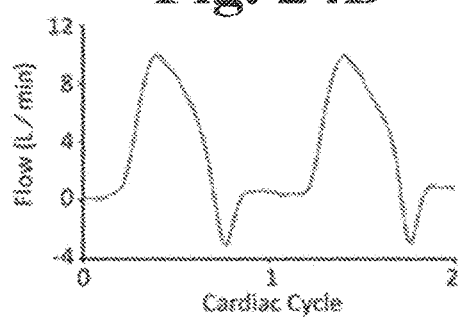
Fig. 24E  Fig. 24F
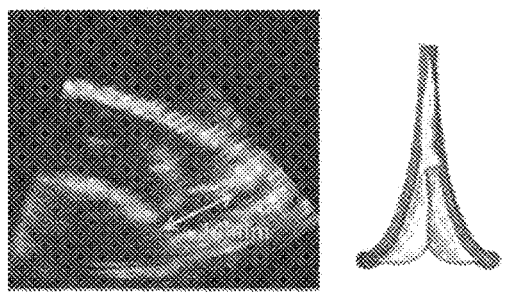 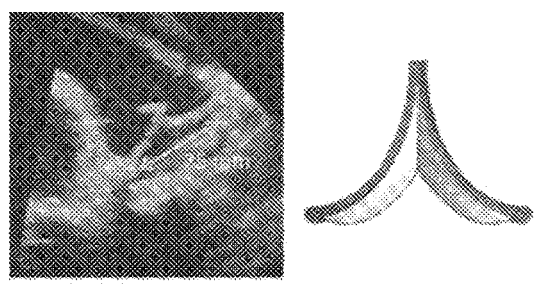
Fig. 24G  Fig. 24H

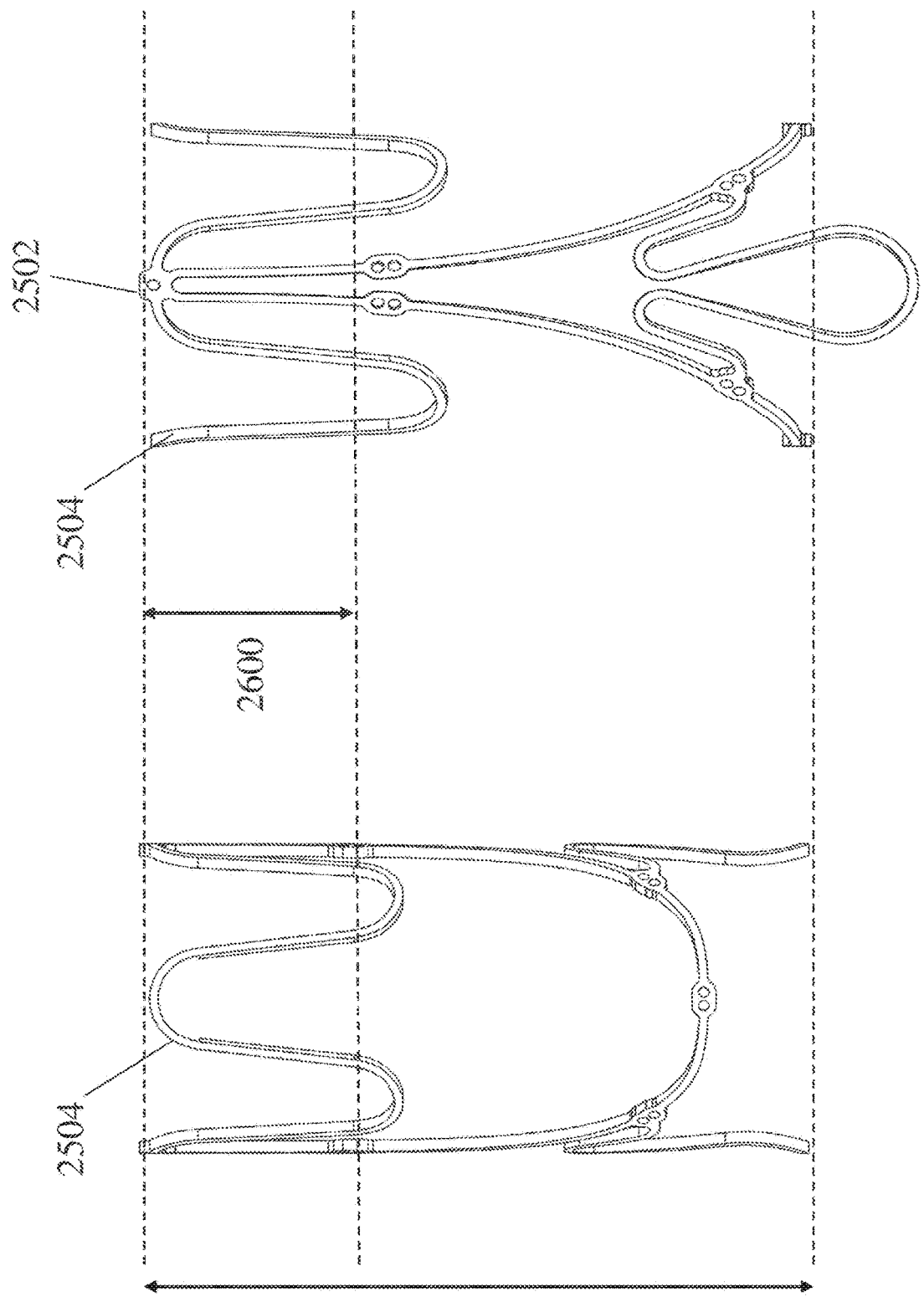

| | Mean PA pressure (mmHg) | Diastolic pressure (mmHg) | Transvalvular gradient (mmHg) | | Effective orifice area (cm$^2$) | Forward flow volume (mL) | Closing volume (mL) | Leakage volume (mL) | Regurgitation fraction (%) (% of forward flow volume) |
|---|---|---|---|---|---|---|---|---|---|
| | | | Mean | Peak | | | | | |
| Right Heart | 20 | 14.1 | 9.2 | 16.7 | 0.6 | 20.6 | 1.5 | 1.1 | 6 |
| Left Heart | 58.1 | 50.7 | 8.9 | 18.5 | 0.6 | 19.6 | 1.7 | 1.5 | 7 |

| | Mean PA pressure (mmHg) | Diastolic pressure (mmHg) | Transvalvular gradient (mmHg) | | Effective orifice area (cm²) | Forward flow volume (mL) | Closing volume (mL) | Leakage volume (mL) | Regurgitation fraction (%) (% of forward flow volume) |
|---|---|---|---|---|---|---|---|---|---|
| | | | Mean | Peak | | | | | |
| Right Heart | 20 | 14.1 | 9.2 | 16.7 | 0.6 | 20.6 | 1.5 | 1.1 | 6 |
| Left Heart | 58.1 | 50.7 | 8.9 | 18.5 | 0.6 | 19.6 | 1.7 | 1.5 | 7 |

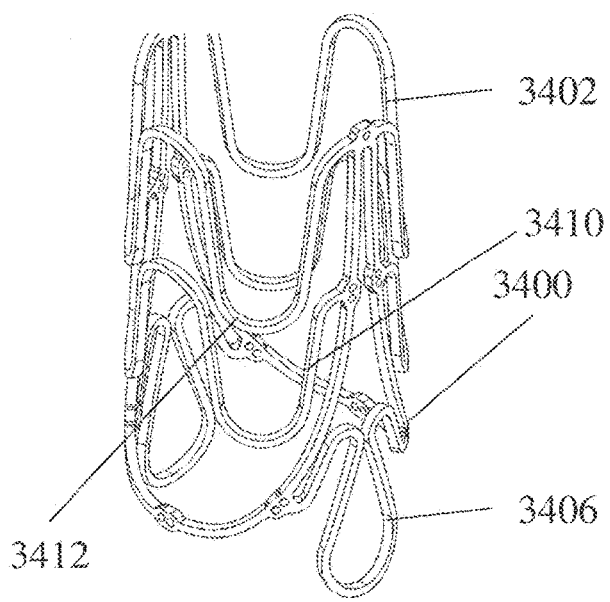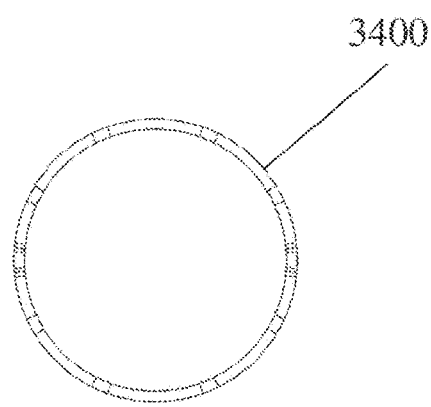
Fig. 35A    Fig. 35B
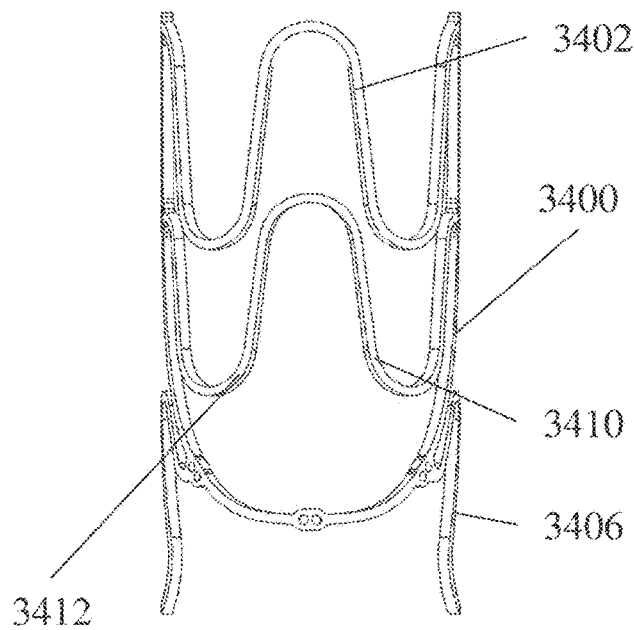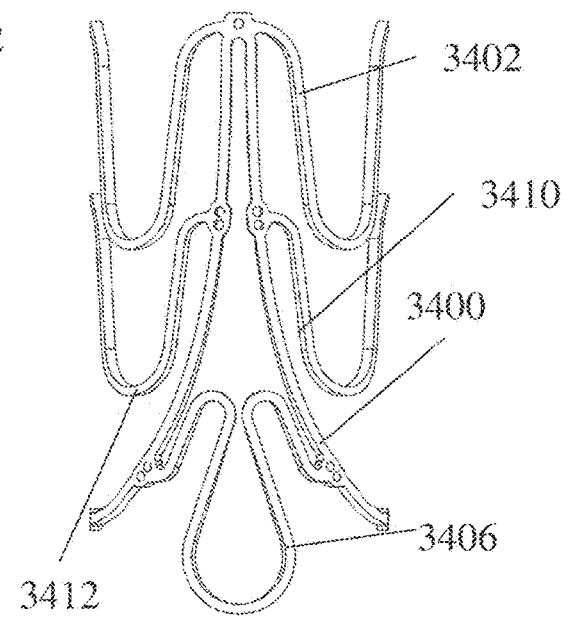
Fig. 35C    Fig. 35D

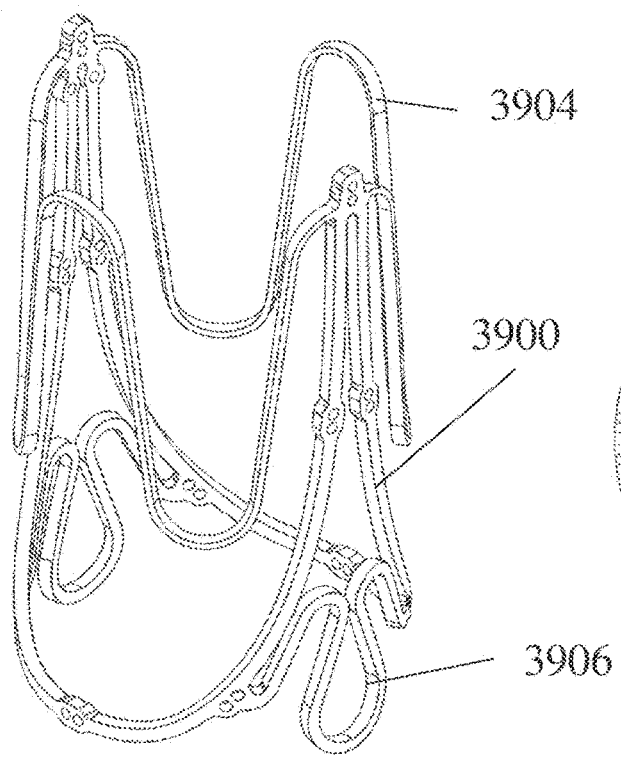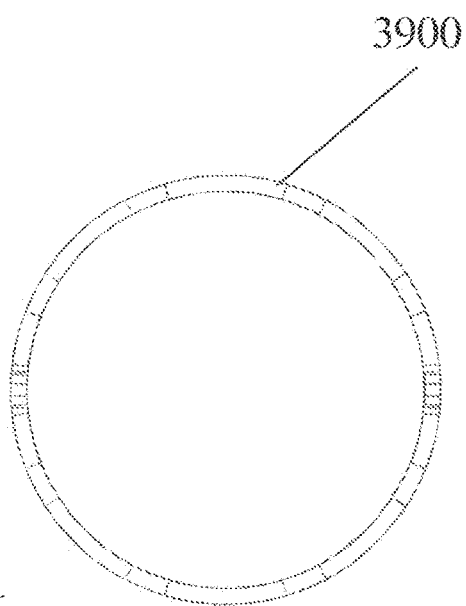
Fig. 39A  Fig. 39B
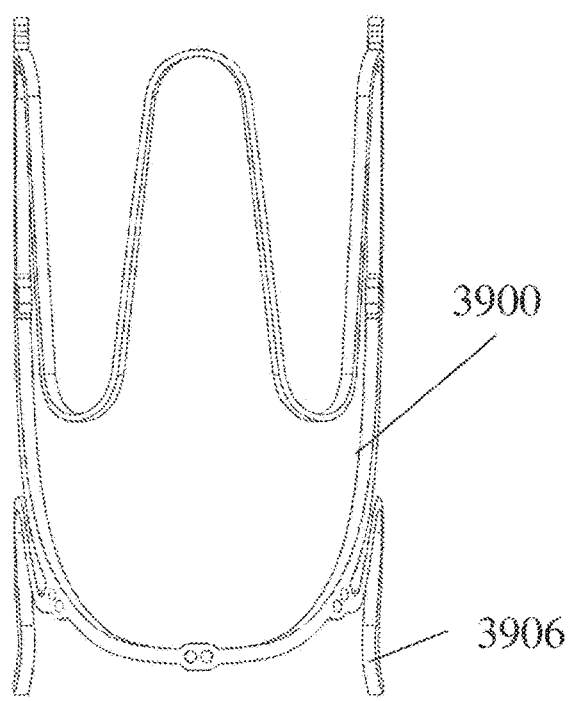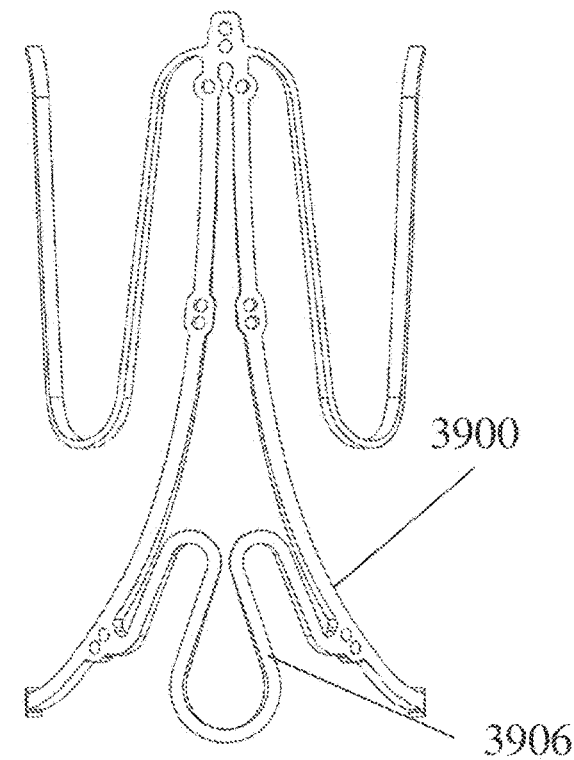
Fig. 39C  Fig. 39D

GEOMETRICALLY-ACCOMMODATING HEART VALVE REPLACEMENT DEVICE

CROSS-REFERENCE TO RELATED APPLICATIONS

This application is a National Stage Filing under 35 U.S.C. § 371 of International Application No. PCT/US2018/061569, filed Nov. 16, 2018, which claims the benefit of U.S. Provisional Patent Application No. 62/587,369, filed Nov. 16, 2017, the entire contents of each of which are incorporated herein by reference.

FIELD

Disclosed embodiments are related to valve replacement devices.

BACKGROUND

The human heart includes a series of valves that work to ensure that blood flows correctly through the chambers of the heart. Birth defects, trauma, or other pathologies can negatively impact the function of a person's native heart valves. Prosthetic heart valves have been developed to either supplement or entirely replace defective native heart valves.

SUMMARY

In one embodiment, a valve replacement device comprises a valve frame that defines an opening for passage of fluid, the opening having a diameter along a largest dimension of the opening. The valve frame is expandable to permit an increase in the diameter of the opening from 5 mm to 50 mm. The device further comprises a first leaflet coupled to the valve frame. The first leaflet has an open configuration in which the opening is exposed, and a closed configuration in which the first leaflet at least partially covers the opening. The first leaflet is moveable between the open and closed configurations as the diameter of the opening expands from 5 mm to 50 mm.

In another embodiment, the valve replacement device comprises a valve frame defining an opening for the passage of fluid. The valve frame has a diameter along a largest dimension of the opening. The valve frame also has a height in a direction perpendicular to the diameter. The valve frame is expandable to increase the diameter in an operational configuration and contractible to decrease the diameter in a contracted configuration. The valve frame has a height to diameter ratio ranging from 0.5:1 to 2.5:1 in the operational configuration. The device further includes a first leaflet coupled to the frame.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 3 is a top view of the frame of the valve replacement device of FIG. 1A over the course of expansion;

FIG. 4 is a front view of the frame of the valve replacement device of FIG. 1A over the course of expansion;

FIG. 6A is a side view of the frame and outer frame support of the valve replacement device prior to expansion;

FIG. 6B is a side view of the frame and outer frame support of the valve replacement device after some expansion;

FIG. 14A is a side view of another embodiment of the frame and leaflets of the valve replacement device;

FIG. 14B is a top view of the frame and leaflets of FIG. 14A;

FIG. 14C is an inverted perspective view of the frame and leaflets of FIG. 14A;

FIG. 14D is a perspective view of the frame of FIG. 14A;

FIG. 15A is a front view of another embodiment of the frame of the valve replacement device;

FIG. 15B is a top view of the frame of FIG. 15A;

FIG. 15C is a side view of the frame of FIG. 15A;

FIG. 15D is a perspective view of the frame of FIG. 15A;

FIG. 15E is a bottom perspective view of the frame of FIG. 15A;

FIG. 23A is a bar graph that depicts both measured flow rate and change in pressure across a valve replacement device having the HB/DB=1.7 valve frame of FIG. 22 at different opening diameters;

FIG. 23B is a line graph illustrating the change in flow rate and flow waveform characteristics of a valve replacement device having the HB/DB=1.7 valve frame of FIG. 22 over the course of a cardiac cycle, at different opening diameters;

FIG. 24A is a graphic conveying that one embodiment of the valve replacement device was tested in vivo in 20 kg lambs;

FIG. 24B is a graphic conveying that one embodiment of the valve replacement device was tested in vivo in 60 kg sheep;

FIG. 24C is a line graph showing the pressure difference (transvalvular pressure gradient, ΔP) between the right ventricle and pulmonary artery of 20 kg lambs, with the valve replacement device implanted, over the course of the cardiac cycle;

FIG. 24D is a line graph showing the pressure difference (transvalvular pressure gradient, ΔP) between the pulmonary artery and right ventricle of 60 kg sheep, with the valve replacement device implanted, over the course of the cardiac cycle;

FIG. 24E is a line graph showing the flow waveform and regurgitation volumes generated by the valve replacement device in its baseline configuration (1×) over the course of the cardiac cycle in 20 kg lambs;

FIG. 24F is a line graph showing the flow waveform and regurgitation volumes generated by the valve replacement device in its fully expanded configuration (1.8×) over the course of the cardiac cycle in 60 kg adult sheep;

FIG. 24G shows an echocardiogram of one of the 20 kg lambs, showing the valve replacement device implanted in its baseline configuration (1×) at 14 mm ID, alongside a graphic of the valve replacement device;

FIG. 24H shows an echocardiogram of one of the 60 kg sheep, showing the valve replacement device expanded to 25 mm (1.8×), alongside a graphic of the valve replacement device;

FIG. 26 shows side and front views of one embodiment of a valve frame of a valve replacement device, annotated to depict an attachment zone for a top reinforcement strut;

FIG. 35A is a perspective view of one embodiment of a valve frame of a valve replacement device;

FIG. 35B is a top view of the valve frame according to the embodiment of FIG. 35A;

FIG. 35C is a front view of the valve frame according to the embodiment of FIG. 35A;

FIG. 35D is a side view of the valve frame according to the embodiment of FIG. 35A;

FIG. 39A is a perspective view of a valve frame of a valve replacement device according to one embodiment;

FIG. 39B is a top view of the valve frame according to the embodiment of FIG. 39A;

FIG. 39C is a front view of the valve frame according to the embodiment of FIG. 39A; and FIG. 39D is a side view of the valve frame according to the embodiment of FIG. 39A.

DETAILED DESCRIPTION

Figure 1A:
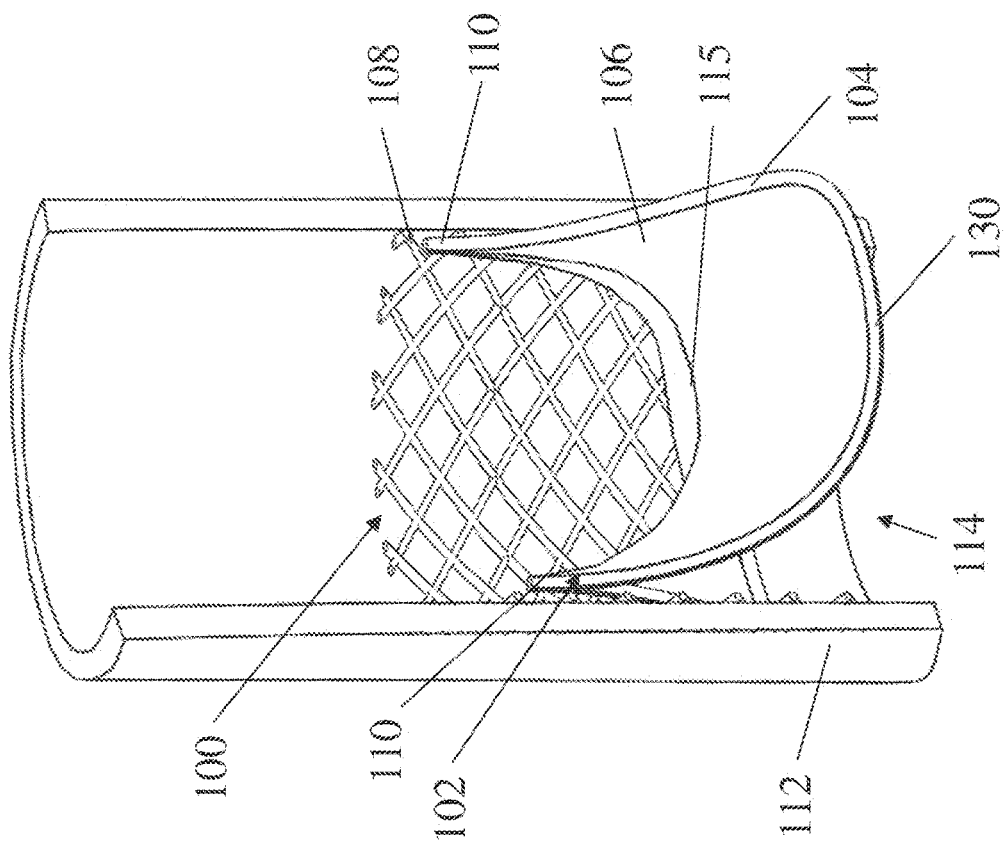
FIG. 1A is a perspective, partial section view of a vessel with a valve replacement device implanted within, prior to expansion.

Some embodiments described herein include a heart valve replacement device that is able to change in size and/or shape to adapt to different implantation environments. In some embodiments, such geometrically-accommodating heart valve replacement devices may be able to adapt to fit with different types of vasculature and/or used with differently sized patients. In some embodiments, some heart valve replacement devices described herein may be used with growing patients and may grow with the patient.

In some embodiments, it is contemplated that the device may also be used elsewhere in the vascular system apart from the heart, for example, as a venous valve prosthesis.

According to one aspect, some embodiments of the heart valve replacement device may enable heart valve function in a diverse range of structural environments, across a range of sizes. The inventors have recognized the need for a heart valve replacement device that is able to change in size and/or shape in order to accommodate varying environments.

According to one aspect, some embodiments of the heart valve replacement device grow with the patient and maintain functionality across a range of sizes as the valve opening increases in size. Current heart valve prosthetics are designed for adults and are intended to remain implanted for potentially up to decades at a time depending on the patient and the condition. Adult patients are commonly expected to get regular check-ups to ensure that the valve has not narrowed or become displaced to ensure optimal function. In some cases, adjusting or replacing a valve can require open-heart surgery. In adults, vasculature lumen diameters and heart sizes do not generally change significantly from year to year. However, in children, vasculature and hearts grow significantly in size as they mature. The inventors have appreciated that, as a result, with current devices, children who have undergone valve replacement have to undergo multiple procedures as they grow to implant suitably-sized valve replacement devices. The inventors have recognized the need for a valve replacement device that is effective over a range of sizes.

While some embodiments described herein are suitable for use in growing patients, it should be appreciated that the heart valve replacement devices described herein are not limited for use in growing patients. The devices may be used in non-growing applications as well. For example, some embodiments may be used as an adult transcatheter valve that can be size-adjusted post deployment for at least the reason of addressing paravalvular leakage that occurs in existing transcatheter valves.

In some embodiments, a first valve replacement device may be implanted in the first few years of life a patient's life, and once the device reaches a full state of expansion, a second valve may be deployed inside the initial implanted device to enable the patient to avoid repeat open-heart procedures.

In some embodiments, it is contemplated that the valve replacement device may also function as a valve within an expandable conduit, which may be a cylindrical tube connecting two heart structures, or some other expandable conduit system. For example, the valve replacement device of some embodiments may be affixed to a cylindrical tube made of expandable synthetic material that acts as a right ventricle to a pulmonary artery conduit. In these embodiments, the valved conduit may be expanded periodically via a transcatheter balloon dilation or other method to accommodate somatic growth of the patient and/or adjusted to match desired pressure and/or flow conditions.

Heart valve function can be characterized by different properties. One measure of heart valve function is regurgitant fraction, which is the amount of blood that leaks backwards through the valve against the intended direction of flow divided by the total amount of blood that flows through the heart valve in one stroke. A healthy, functional valve exhibits low amounts of regurgitation. The inventors have appreciated that, in some cases, a regurgitant fraction of 0%-20% is desirable. Another measure of heart valve function is the amount of mean and peak transvalvular pressure gradient exhibited by the valve. This pressure metric is of interest because it quantifies valve function in allowing unimpeded forward flow. The inventors have appreciated that, in some cases, a peak transvalvular pressure gradient of 0 mmHg-40 mmHg for the right side of the heart and 0 mmHg-30 mmHg for the left side of the heart is desirable.

In some embodiments, the valve replacement device includes one or more leaflets coupled to a frame. The leaflets surround an opening of the device through which blood can flow. The leaflets have an open configuration and a closed configuration. In the open configuration, the leaflets part and expose the opening of the device to permit blood flow through the opening. In the closed configuration, the leaflets coapt and obstruct the opening of the device to prevent backflow of blood. The leaflets move between the open and closed configurations based on the pressure differentials across the valve during the cardiac cycle. In some embodiments, the device includes two leaflets. However, other numbers of leaflets may be used, such as three, four, five or more leaflets. In some embodiments, the heart replacement device includes only one leaflet. The single leaflet may extend from one side of the frame to the other. In some embodiments, the leaflets are moon-shaped, e.g., ¾ to ½ moon shaped leaflets.

In some embodiments, the frame may comprise a pair of semi-elliptical frame sections joined at a pair of commissures. The frame sections curve laterally outwards away from each other, forming a half-hourglass shape. As the surrounding vasculature widens, the two frame sections spread further apart at the open end, increasing the opening of the device and matching the cross-sectional area of the expanding lumen to accommodate growth. Each leaflet may be attached to the inner perimeter of each of the frame sections, mimicking the leaflet vessel wall attachment line of a native venous valve.

In some embodiments, the device includes an outer frame support coupled to the frame. In some embodiments, the outer frame support may be a semi-rigid cylindrical mesh. The frame is attached to the inside of, and is kept stable by, the outer frame support. Due to the rigidity of the outer frame support, the outer surface of the outer frame support presses against the inner walls of the vasculature in which the device is implanted, keeping the lumen of the surrounding vasculature open and maintaining the orientation and position of the device. The outer frame support can function similarly to a stent, allowing the device to be delivered via catheter delivery or direct surgical implantation. It should be appreciated however, that, in some embodiments, the frame may be used on its own without the addition of the outer frame.

According to one aspect, in some embodiments, the frame of the valve replacement device maintains a constant perimeter length (e.g., the site of leaflet attachment is non-lengthening) throughout the growth process, i.e., the perimeter length does not stretch or elongate during growth. Instead, as the frame sections spread apart to accommodate growth, the height of the commissures reduces. In some embodiments of this non-lengthening design, accommodation of radial growth is achieved by balloon expanding a plastically-deformable material (e.g. steel, cobalt chromium, etc.). As a result, the leaflets attached to the frame sections do not become deformed (i.e. do not stretch, lengthen or unfold) as the valve opening expands. The extent of coaptation of the leaflets (i.e. length of leaflet material in contact with other valve leaflets in closed state) may decrease as the opening expands.

In some embodiments, the frame sections of the frame are configured to maintain their shape as the device expands to accommodate growth, and thus the leaflets are not distended or stretched over the course of growth.

In an alternative embodiment, rather than preserving a constant perimeter length of the frame as the opening of the device grows, the frame may lengthen as the device grows. This may serve to decrease the amount of height change that the device undergoes during opening expansion. The frame may be made from any suitable material and/or may be constructed in any suitable form to permit the frame perimeter to lengthen as the device grows. For example, the frame may be made from an elastic material that can elastically stretch and elongate, may include telescoping segments, may include bio-erodible segments, or may include any other suitable mechanism that would allow the frame perimeter to elongate while the frame segments spread out away from one another.

In some embodiments, the frame may include segments having a bio-erodible outer sleeve with a core comprising telescoping or folded flexible segments. As the outer sleeve erodes, the core becomes exposed. When the vasculature expands, the radial pulling force on the frame causes the core to expand or unfold, allowing the frame to expand.

In some embodiments of the valve replacement device, the frame expands laterally outwards asymmetrically in that the frame sections move apart at different rates. The shape of each frame section may be maintained throughout growth/expansion, but the opening may grow more in one direction than the other. To accomplish the asymmetric expansion, these embodiments could have frame sections made from materials of differing stiffness, or could have angled commissures such that expansion favors one side over the other.

The frame and/or outer frame support may be self-expanding or may expanded by other means, such as by balloon expansion.

The valve replacement device may be delivered via minimally invasive means such as by a transcatheter approach, or may be implanted via open-heart surgery.

In some embodiments, the curve profile of the arcs of the frame sections can be obtained by projecting an elliptical quadrant on to a cylinder. It is contemplated that the cylinder could be representative of the shape of the inner wall of a vessel. The cylinder would have a radius equivalent to that of the valve held by the valve frame. The other frame section would match the projected curve profile but mirrored about the centerline of the cylinder. It should be understood that other frame section shapes and curve profiles are contemplated as well. However, it is also contemplated that other possible methods of defining the shape of the frame sections are contemplated and the current disclosure is not so limited. The frame sections may also have other shapes.

In some embodiments, a valve replacement device may include reinforcement features such as struts that connect the two frame sections of the valve frame. Such reinforcement struts may serve to maintain the shape of the valve frame during expansion. Some embodiments of the valve replacement device may include a top reinforcement strut that connects the two frame sections. The top reinforcement strut may be attached to the frame at or near the top of the pairs of commissures. The top reinforcement strut may have a length that is equal to or greater than the circumference of the frame opening at its maximum expansion diameter. The top reinforcement strut may form an annulus, or an ellipse, or may be asymmetrically shaped in its fully expanded state. In a non-expanded shape, the top reinforcement strut may have an undulating profile extending about a longitudinal axis of the valve replacement device such that the top reinforcement strut has a circular or elliptical or asymmetric profile when viewed from the top regardless of the state of the valve replacement device's expansion. In some embodiments, the top reinforcement strut may have undulations that gives the top reinforcement strut a smaller diameter before expansion of the frame, but allowing the top reinforcement strut to expand with the frame. The top reinforcement strut may be comprised of a material with sufficient stiffness to provide reinforcing integrity to the frame as it expands, but with enough flexibility to allow the undulations to straighten out to permit the top reinforcement strut to expand.

In other embodiments, the top reinforcement strut may have a variety of different geometries that may be varied according to the application of the valve replacement device. For example, the top reinforcing feature may be diamond shaped to more readily allow the valve to be compressed over a catheter for percutaneous transvenous or transarterical valve deployment. Other shapes are also contemplated and the current disclosure is not so limited.

Other shapes for the top reinforcement feature are contemplated. For instance, the top reinforcement feature could comprise multiple expandable segments connecting the frame sections instead of a single annulus. The segments could be telescoping segments, or be otherwise folded or compressed to allow the feature to expand. The top reinforcement strut could also take on non-annular shapes as long as the feature can expand with the frame and fit within the implanted environment.

Some embodiments of the valve replacement device could include reinforcement features not attached to the commissures of the valve frame. For instance, some embodiments could have a lower reinforcement strut connecting the respective lower sides of the frame sections to each other. The lower reinforcement struts may also have an undulating or otherwise compressed or folded shape that allows the lower feature to expand with the frame. Similar to the top reinforcement strut, the lower feature may be comprised of a material with enough stiffness to give the valve frame additional structural strength, while being flexible enough to allow the lower reinforcement strut to expand and/or straighten out or unfold.

The lower reinforcement strut may be flared beyond the cylindrical plane of the valve frame opening to allow for device fixation to native heart structures, or may be used as a fixation method for a valve-in-stent transcatheter deployment or valve-in-valve transcatheter deployment, among other applications.

In other embodiments, the lower reinforcement strut may have a variety of different geometries that may be varied according to the application of the valve replacement device. For example, the top reinforcing feature may be diamond shaped to more readily allow the valve to be compressed over a catheter for percutaneous transvenous or transarterical valve deployment. Other shapes are also contemplated and the current disclosure is not so limited.

The top and lower reinforcement struts, or any other reinforcement strut, may also be tuned to alter or control the shape of the valve as the valve expands. The material properties, geometry, thickness of the reinforcement struts, etc. may be modified to achieve a specific opening geometry with expansion. The reinforcement struts may also differ in material, geometry, or thickness to achieve a specific opening geometry with expansion. One reinforcement strut may even differ in material or thickness within said reinforcement strut to achieve a specific opening geometry with expansion. In some embodiments, it is contemplated that the reinforcement struts could control the expansion of the frame to cause the opening to be elliptical in shape, or asymmetrically shaped, or circular in shape. Other shapes are contemplated as well. For example, a reinforcement strut may be materially thicker on one side, or shorter on one side, or be made of a stiffer material on one side to ensure that that side does not expand to the same degree as the other side of the frame.

While top and lower reinforcement features are described, it should be understood that some embodiments can include one of or both of the top and lower reinforcement features. Additionally, some embodiments may include additional features that connect the frame sections and may be located between the top and lower reinforcement features.

In some embodiments, the valve replacement device may include a plurality of holes spaced along the frame. The holes may act as anchor points for sutures to assist in the attachment of the leaflets to the frame. In some embodiments, the leaflets have additional protruding segments of material that is affixed to the frame via interspersing slots along the length of the leaflet attachment line, and then mechanically fixed on the outside of the frame.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

Figure 1B:
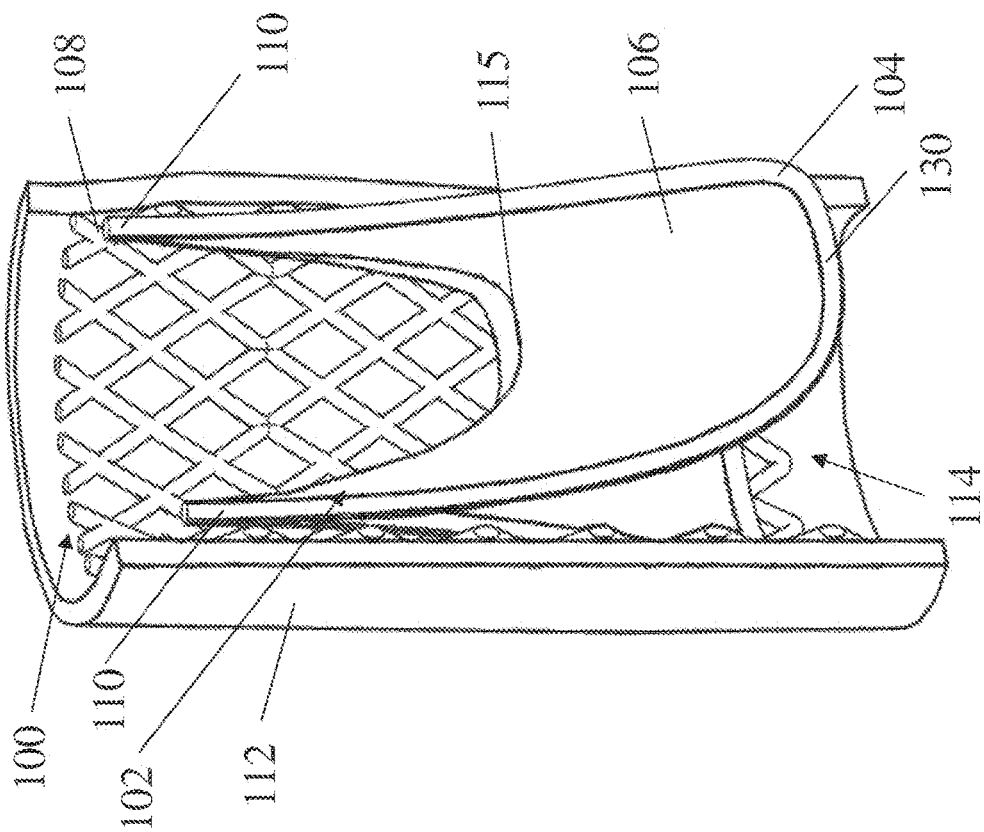
FIG. 1B is a perspective, partial section view of the vessel and valve replacement device of FIG. 1A with the device having undergone some expansion.

FIG. 1A shows one embodiment of the valve replacement implanted within a representative vessel. Valve replacement device 100 comprises a frame 102 and an outer frame support 108. Frame 102 may be symmetrical, with two frame sections 104 that converge at commissural posts 110. The frame sections may each be U-shaped arcs. Lining the arc of each frame section 104 is a leaflet 106. The leaflets 106 hang off of frame sections 104 such that in the device's closed configuration, the leaflets hang down and coapt, obstructing the device opening. As blood flows through the vessel (flowing upwards from the bottom as viewed in FIG. 1A), the flow of blood pushes the leaflets apart, exposing the opening and placing the leaflets in an open configuration. As blood flow begins to slow, the leaflets once again collapse to the closed configuration, preventing regurgitation of blood. As can be seen in FIG. 1B, as the vessel around the device grows, the device similarly expands with the vessel to continue effectively serving as a replacement valve.

Figure 2:
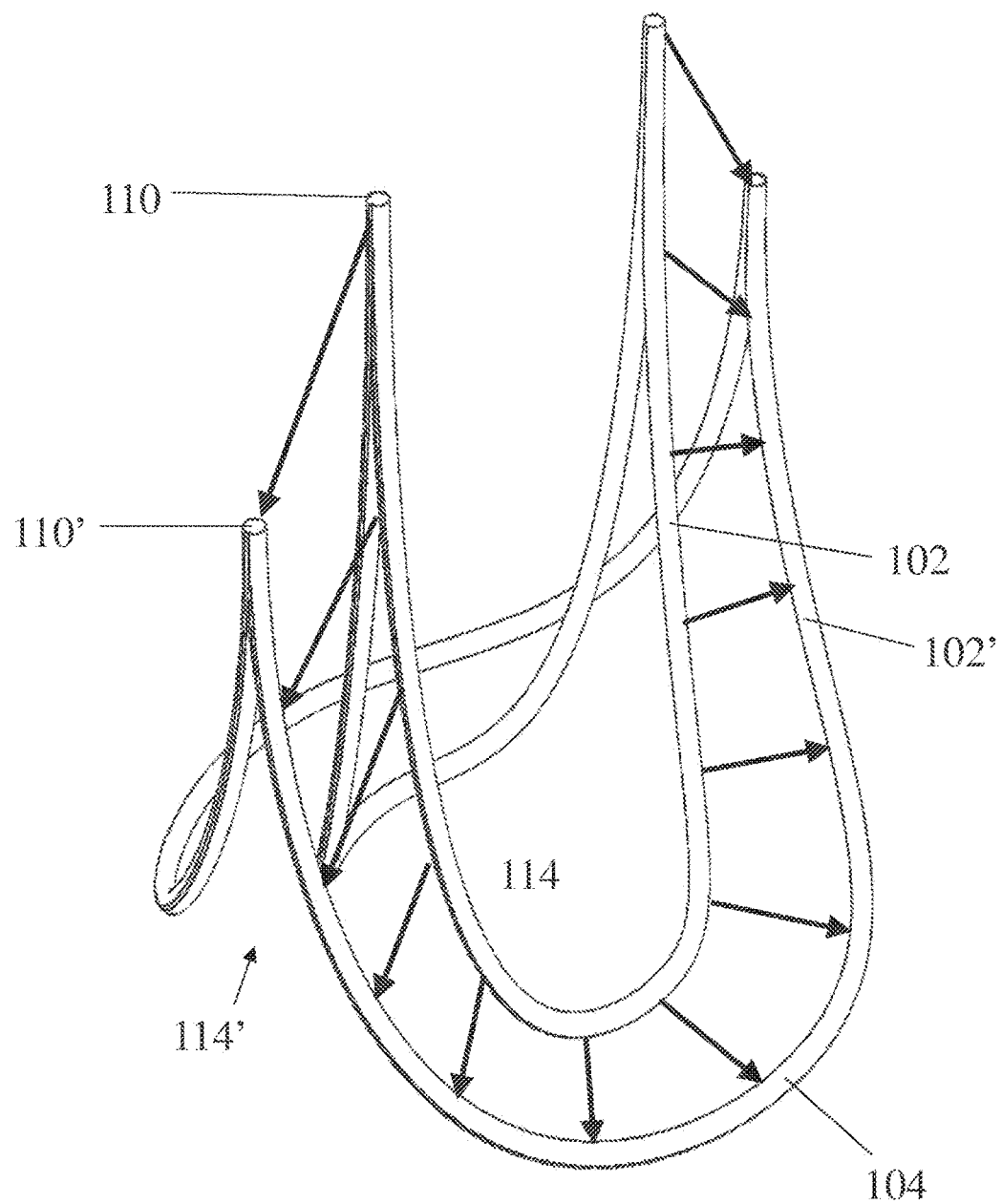
FIG. 2 is a perspective view of the frame of the valve replacement device of FIG. 1A over the course of expansion.

FIGS. 2, 3, and 4 show different perspectives of one embodiment of the frame as it expands. Frame 102 shows the frame initially, while 102' shows the frame after some expansion. As best seen in FIGS. 2 and 3, the opening of the frame expands from a pre-expansion opening 114 to a larger expanded opening 114' Similarly, commissural posts 110 shows the posts prior to expansion, and 110' shows the posts after some expansion. The frame may have a vertical height (axial length) of between 5 mm-50 mm, and an internal diameter of 5 mm-50 mm at its baseline prior to expansion.

In some embodiments, the frame may have a height to diameter ratio of about 0.5:1 to 2.5:1, or 0.6:1 to 2.4:1, or 0.7:1 to 2.3:1, or 0.8:1 to 2.2:1, or 0.9:1 to 2.1:1, or 1:0 to 2:1, or 1.1:2.0, or 1.2:1 to 1.9:1, or 1.3:1 to 1.9:1, or 1.3:1 to 1.8:1, or 1.4:1 to 1.7:1, or 1.5:1 to 1.8:1, or 1.6:1 to 1.7:1, or 0.6:1 to 2.5:1, or 0.7:1 to 2.5:1, or 0.8:1 to 2.5:1, or 0.9:1 to 2.5:1, or 1.0:1 to 2.5:1, or 1.1:1 to 2.5:1, or 1.2:1 to 2.5:1, or 1.3:1 to 2.5:1, or 1.4:1 to 2.5:1, or 1.5:1 to 2.5:1, or 1.6:1 to 2.5:1, or 1.7:1 to 2.5:1.

Figure 5A:
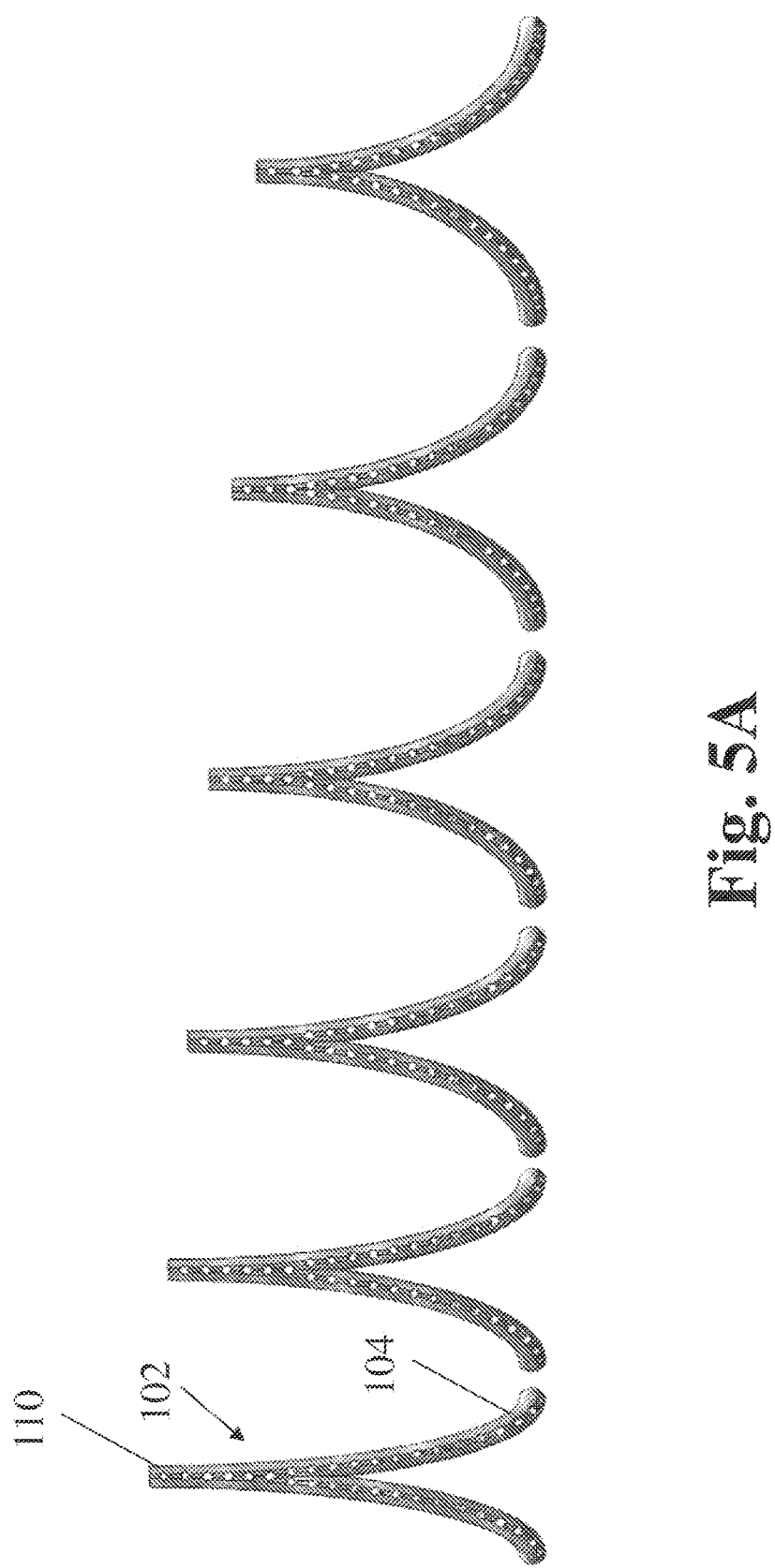
FIG. 5A is a side view of the frame of the valve replacement device of FIG. 1A during increasing stages of expansion from left to right.
Figure 5B:
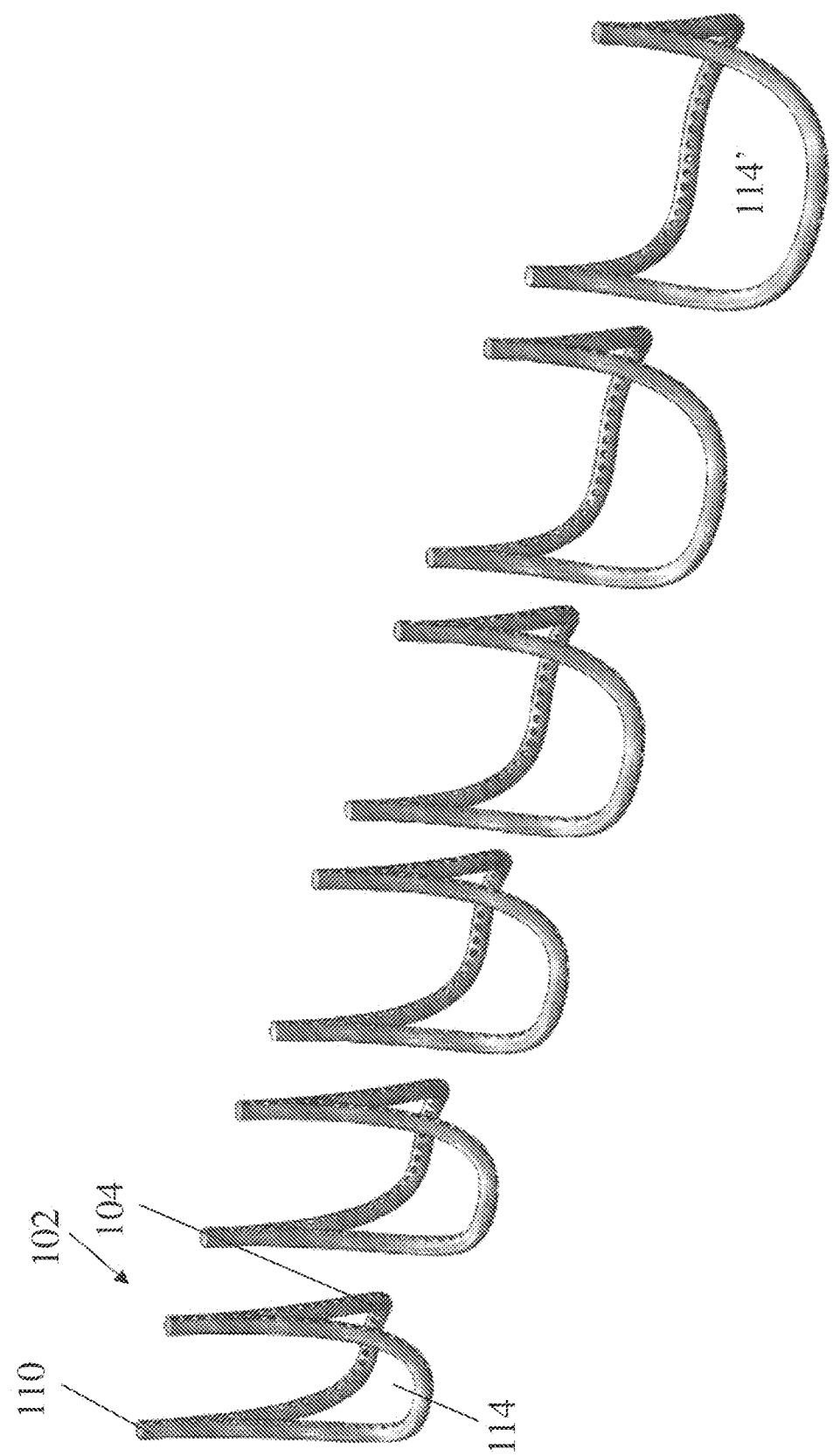
FIG. 5B is a perspective view of the frame of the valve replacement device of FIG. 1A during increasing stages of expansion from left to right.
Figure 7A:
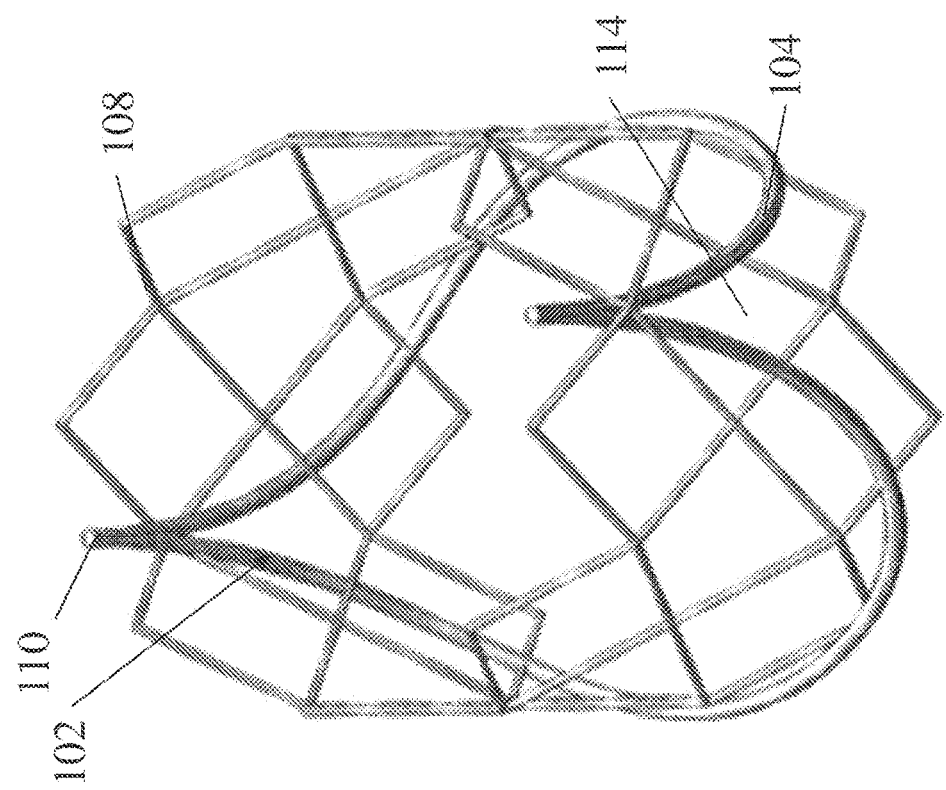
FIG. 7A is a top perspective view of the frame and outer frame support of FIG. 6A prior to expansion.
Figure 7B:
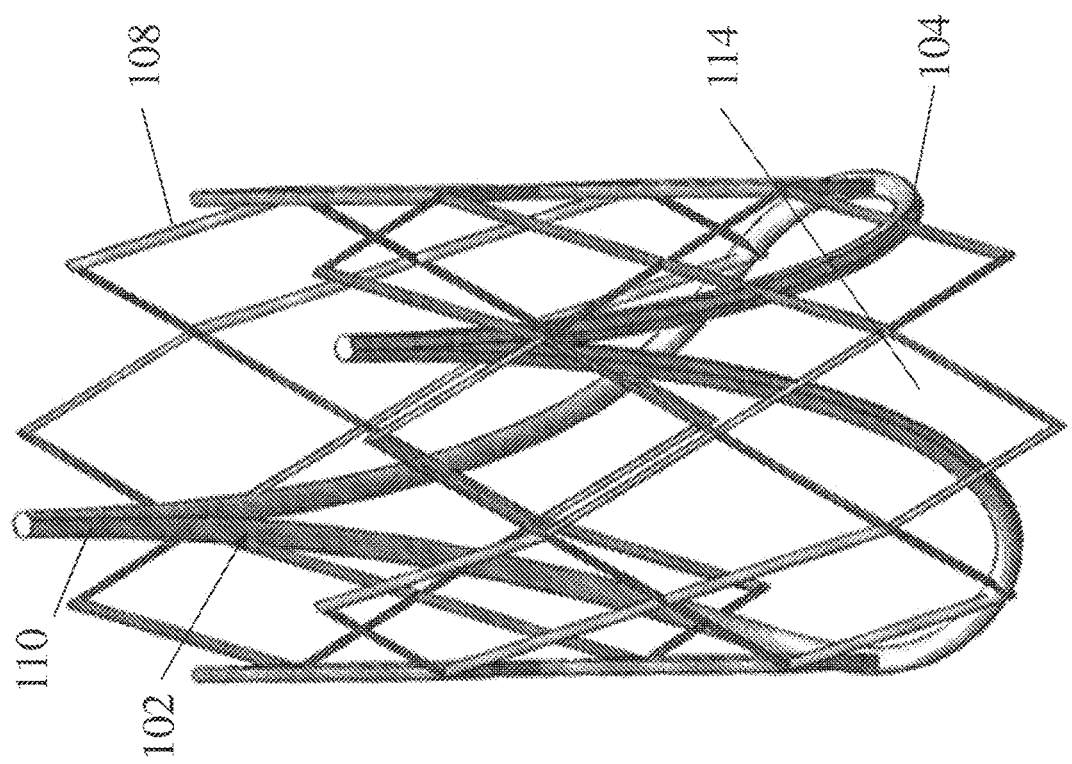
FIG. 7B is a top perspective view of the frame and outer frame support of FIG. 6A after some expansion.

As the frame expands, the two frame sections 104 move laterally away from each other. As the frame sections 104 move away from each other, the commissural posts 110 decrease in height. FIGS. 5A and 5B show a time lapse of the frame expanding from a small diameter configuration (left) to a large diameter configuration (right). As can be seen from FIGS. 3 and 4, in some embodiments, as the frame expands, it may expand evenly in all radial directions. In some embodiments, the spreading mechanism of the frame sections 104 that occurs during growth to expand the overall frame 102 may preserve the perimeter length of each frame section 104. As seen in FIG. 5B, the pre-expansion opening 114 expands to a larger expanded opening 114' as the frame expands.

The frame may be made of: nitinol, titanium, cobalt chromium alloy, stainless steel, a biodegradable polymer, a bioresorbable polymer, a synthetic material, platinum iridium, a magnesium or iron alloy, and/or any other suitable material.

In some embodiments, each leaflet 106 may have a ¾ to ½ moon shape so that the concaved-out side matches the arc of the frame sections 104 that the leaflet is attached to. The leaflet 106 may be sutured, adhered, or otherwise attached to a frame section. The concave-in side or the free edge 115 (see FIGS. 1A, 1B for an illustrative example of a free edge) of the leaflet may have a length of up to 4 times the diameter of valve in baseline state/configuration, while the leaflet vertical height may be up to 2.5 times the diameter of valve in baseline state/configuration. The height of the center of the leaflet can range from 0.2 to 0.8 times the height of the leaflet at the commissural posts. As the frame expands, the leaflet-commissure attachment angle increases, resulting in straightening of the leaflet's free edge 115. The excess leaflet height ensures that there is sufficient coaptation for the device to function effectively as a valve across the full range of the device's expansion. The coaptation height can be up to three quarters of the opening diameter prior to valve frame expansion. While the depicted embodiments show equally sized and shaped leaflets that are symmetric to one another, the valve leaflets may be different in size and/or shape from one another. In some embodiments, one larger leaflet may cover the majority of the valve opening in the closed position, with one or more smaller leaflets forming a crescent-like shape in the closed position.

While dimensions for the leaflets are provided above, it should be understood that other sizes are also contemplated. For example, the free edge of the leaflet may have a length of between 2 to 6 times or some other range. The leaflet vertical heights may be between 1.5 to 3.5 times the diameter of the valve in the baseline configuration or 2.2 to 2.7 times. The mid-height of the valve may be from 0.1 to 1 times the height of the leaflet at the commissural posts. Other ranges are further contemplated.

While the depicted embodiments show designs utilizing two leaflets, designs using three or more leaflets with two or more frame sections are also contemplated. Designs using a single leaflet are also contemplated.

The leaflets can be made of a bioabsorbable polymer, a synthetic polymer, a tissue-engineered construct, a decellularized homologous tissue engineered leaflet, a thin film nitinol, an expanded PTFE membrane, a gluteraldehyde-treated bovine pericardium, a gluteraldehyde-treated porcine pericardium, a photo-oxidized bovine pericardium, a bovine jugular vein valve, or any other suitable composition or material. In some embodiments, the leaflets are made of GORE-TEX 0.1 mm Pericardial Membrane having a Young's modulus of around 60 MPa at physiological loads. Young's modulus ranges from 30 MPa to 4 GPa, or 70 MPa to 4 GPa, or 100 MPa to 4 GPa, or 200 MPa to 4 GPa, or 500 MPa to 4 GPa for the leaflet material are also contemplated.

FIGS. 6A, 6B, 7A, and 7B show views of the frame and the outer frame support at different stages of expansion according to one embodiment of the device. The outer frame support 108 in this embodiment is a mesh cylinder with open cells. As shown in FIGS. 1A and 1B, the outer frame support may provide stability for the device and maintain the orientation of the frame relative to the vessel 112. As the frame 102 expands, the mesh tube comprising outer frame support 108 may expand as well, reducing the height of the outer frame support while increasing its diameter to match the diameter of the vessel.

While the depicted embodiment shows the outer frame support in the form of a mesh cylinder with open cells, it should be understood that the outer frame support may take different forms as well. The outer frame support may have closed cells or may have mixed open and closed cells. The outer frame support may also comprise a partially solid cylinder with expandable segments, or any other arrangement that would allow the outer frame support to expand with the frame.

In some embodiments, the valve replacement device may include an outer flexible covering that may wrap around the outer frame support, or, in the absence of a separate outer frame support, may wrap around the frame itself. The flexible covering may prevent tissue ingrowth into the outer frame support, as well as the formation of abnormal layers of fibrovascular or granulation tissue. The frame and the flexible covering may be chemically inert, or they could be treated with compounds to imbue desirable properties including but not limited to anti-adhesive properties, or anti-thrombogenic properties.

Figure 8:
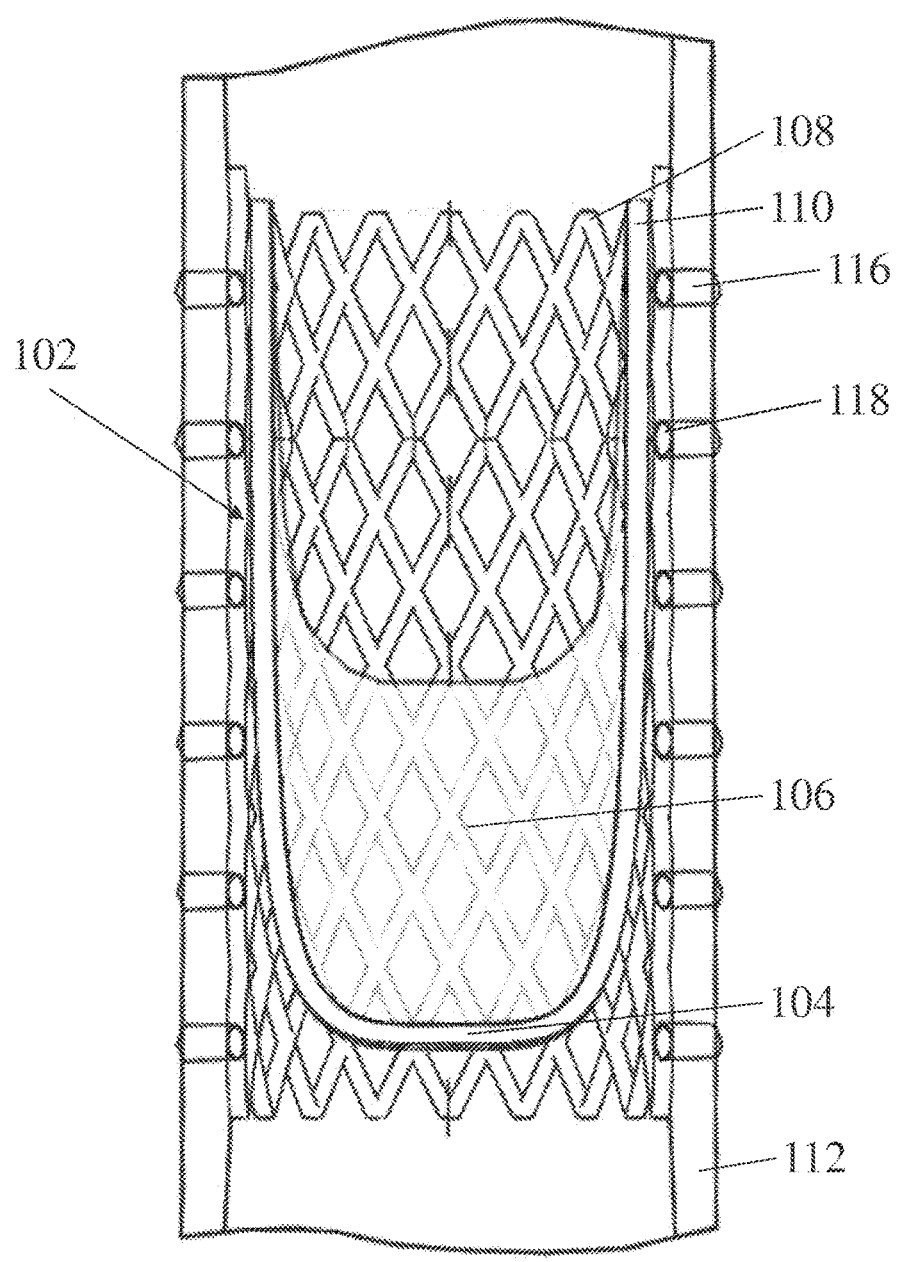
FIG. 8 is a cross-sectional view of one embodiment of the valve replacement device implanted in a vessel according to one embodiment.

FIG. 8 shows one embodiment of the valve replacement device implanted in a vessel 112. In this embodiment, the outer frame support 108 is secured to the vessel 112 by a series of sutures 118 spaced along the length of the outer frame support 108. The sutures 118 fix the outer frame support to the vessel such that as the vessel grows, the vessel provides a radially outward force on the outer frame support that causes the outer frame support to expand, in turn causing the expansion of frame 102. In some embodiments, the outer frame support may include a plurality of holes 116 to receive such sutures.

Figure 9:
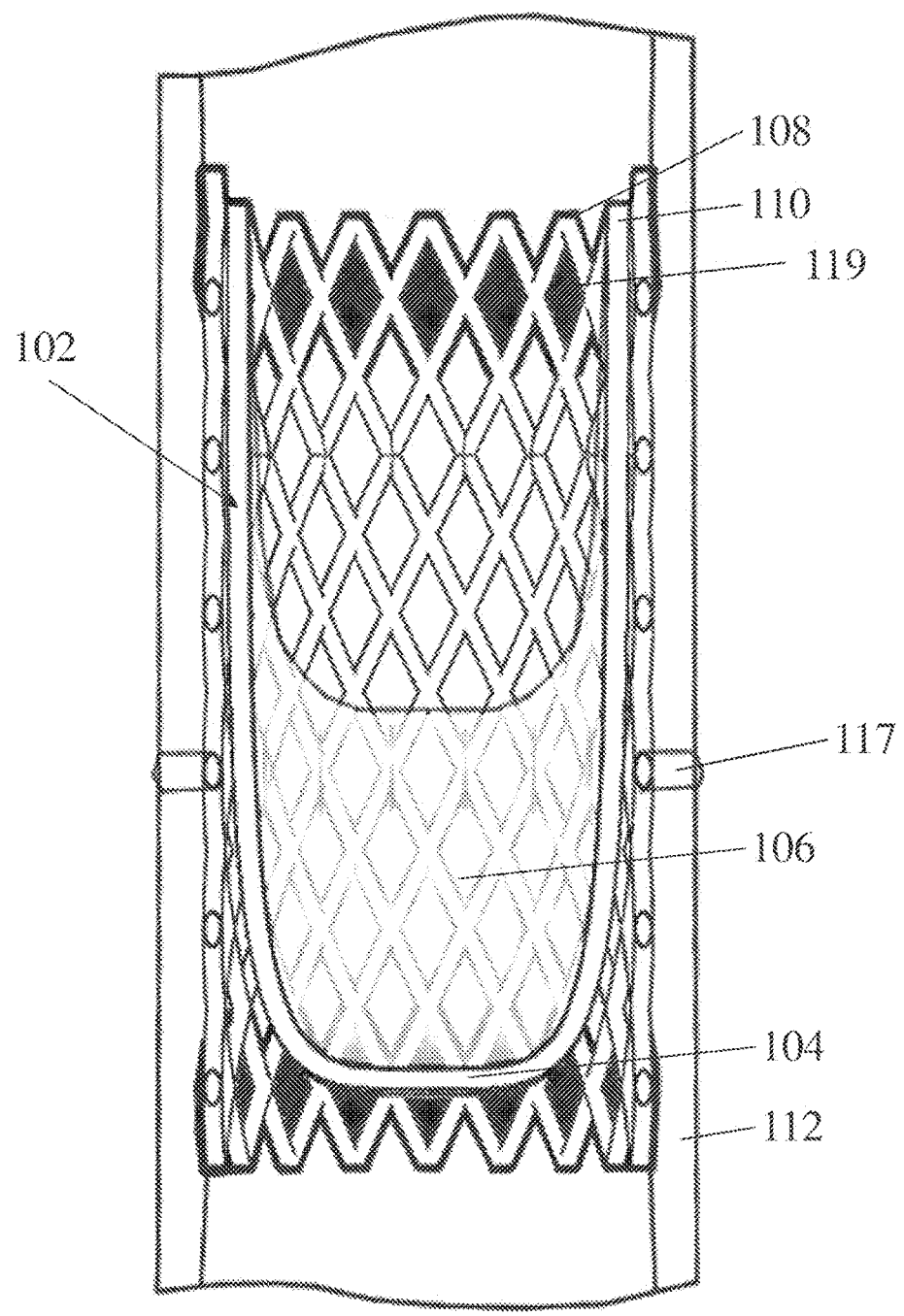
FIG. 9 is a cross-sectional view of one embodiment of the valve replacement device implanted in a vessel according to another embodiment.

In some embodiments, the outer frame support may be secured to the vasculature at only a single attachment location. For example, the outer frame support may be secured to the vasculature at only a single attachment line along the height of the device. In the embodiment shown in FIG. 9, the outer frame support 108 is secured along a single line 117 to the vessel 112. Having a single attachment location between the vasculature and the device may help permit changes in height and diameter of the device, as well as accommodate axial growth of the vasculature. In some embodiments, the device may also include proximal and distal seals 119 at either axial end of the device. The proximal and distal seals 119 may prevent paravalvular leak, stasis of blood flow, or otherwise aberrant blood flow profiles. In some embodiments the valve may have an outer covering made of expandable synthetic material that extends beyond the base of the valve. The material may be used as a sewing ring to fix the valve in the position of the native valve annulus. This may be the only site of device attachment.

Figure 10:
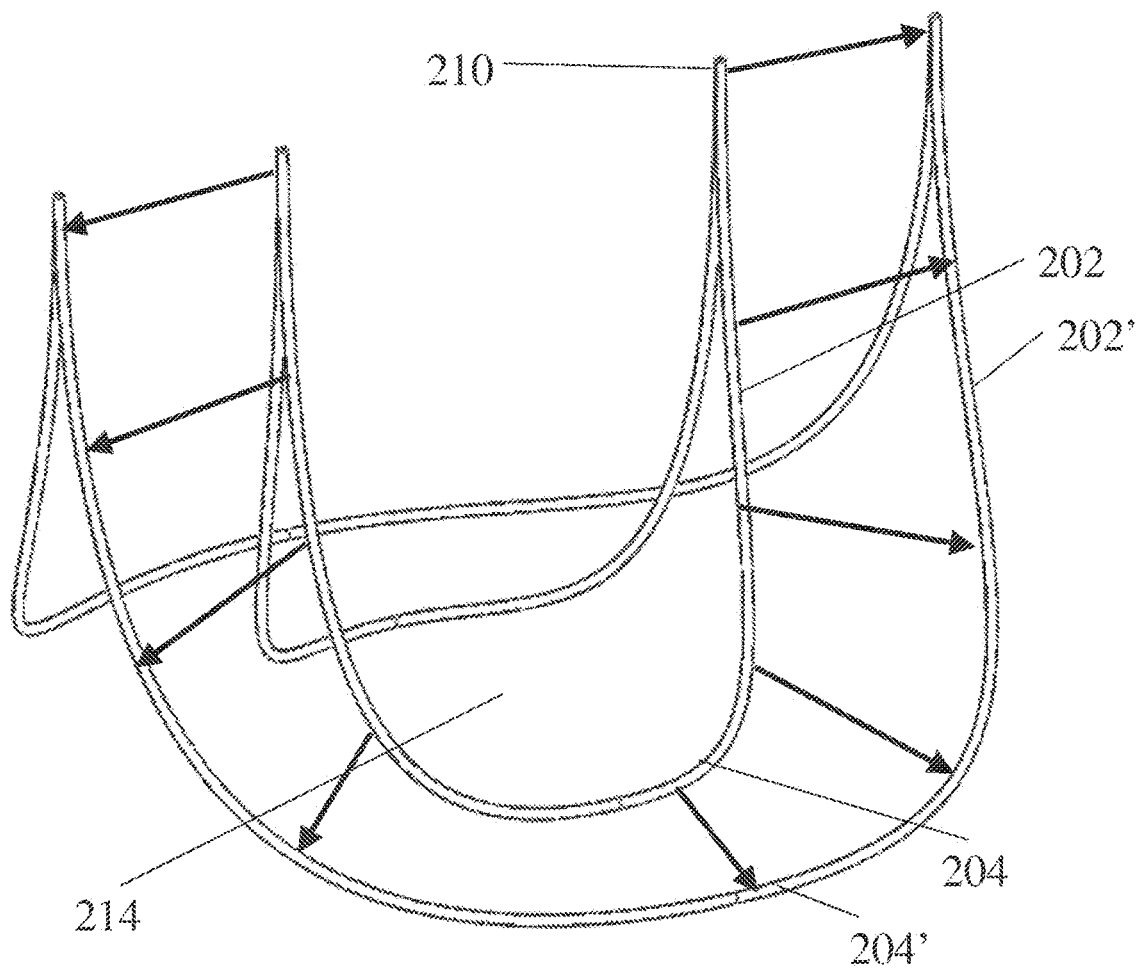
FIG. 10 is a perspective view of one embodiment of the frame of the growth-accommodating valve replacement device over the course of expansion.
Figure 11:
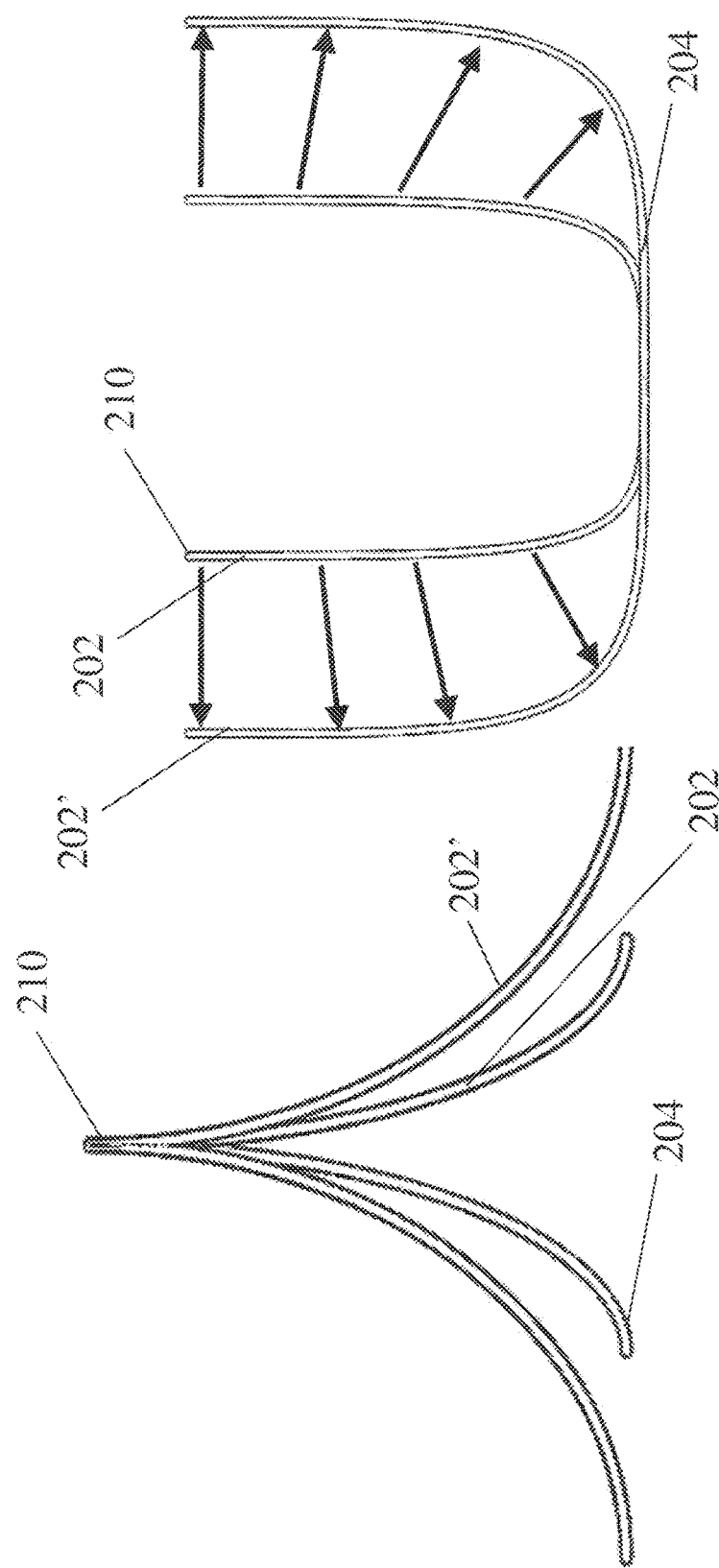
FIG. 11A is a side view of the frame of FIG. 10 over the course of expansion.
FIG. 11B is a front view of the frame of FIG. 10 over the course of expansion.
Figure 12:
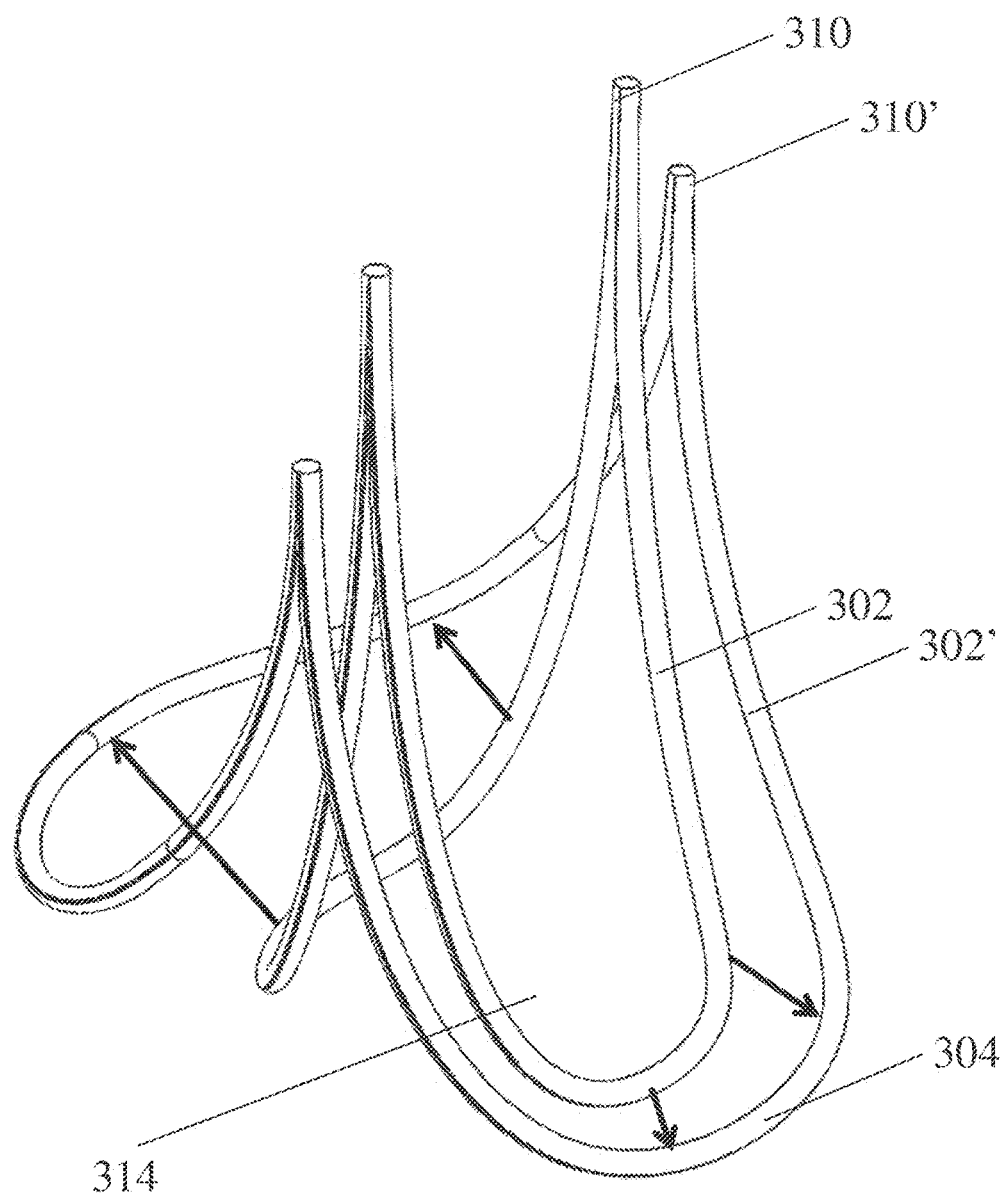
FIG. 12 is a perspective view of another embodiment of the frame of the valve replacement device over the course of expansion.
Figure 13A:
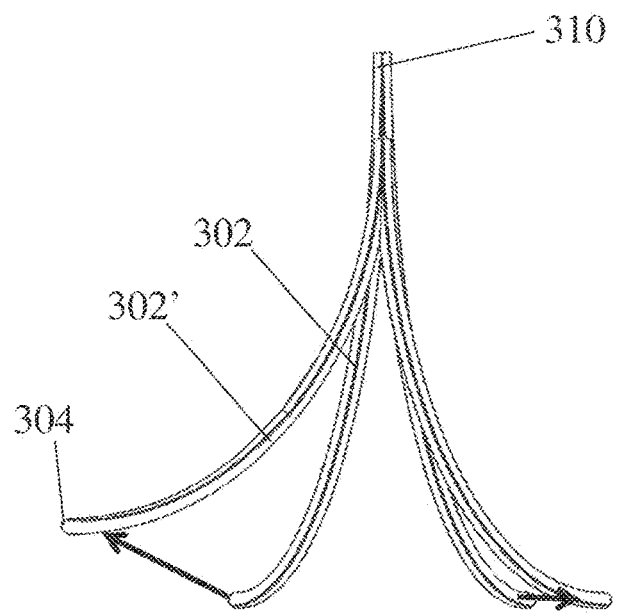
FIG. 13A is a side view of the frame of FIG. 12 undergoing some expansion.
Figures 13B, 13C:
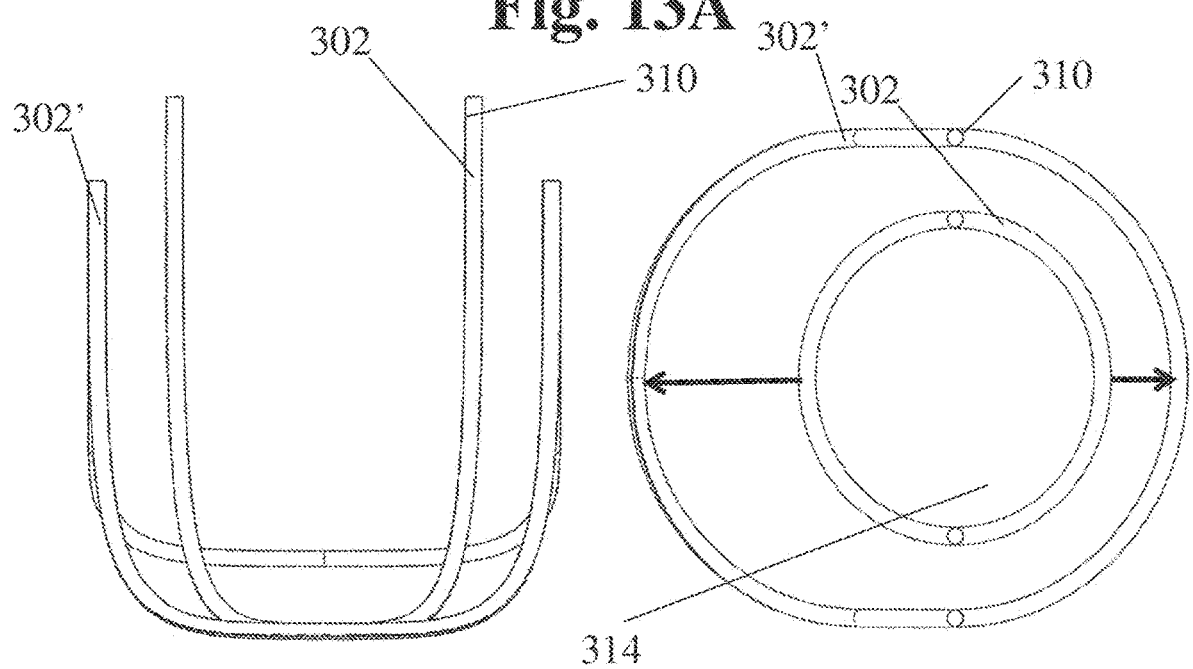
FIG. 13B is a front view of the frame of FIG. 12 undergoing some expansion.
FIG. 13C is a top view of the frame of FIG. 12 undergoing some expansion.
Figure 16A:
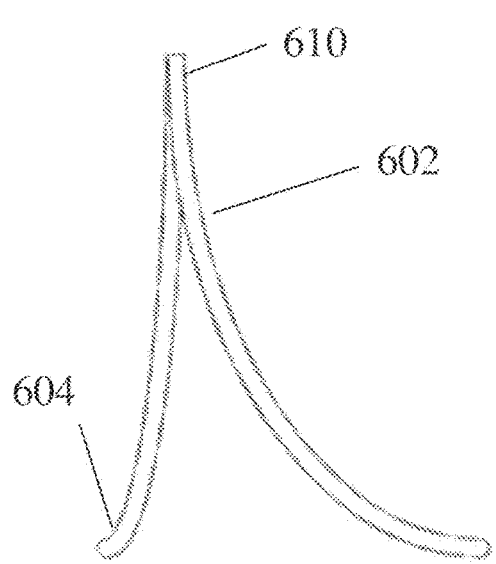
FIG. 16A is a side view of another embodiment of the frame of the valve replacement device.
Figure 16B:
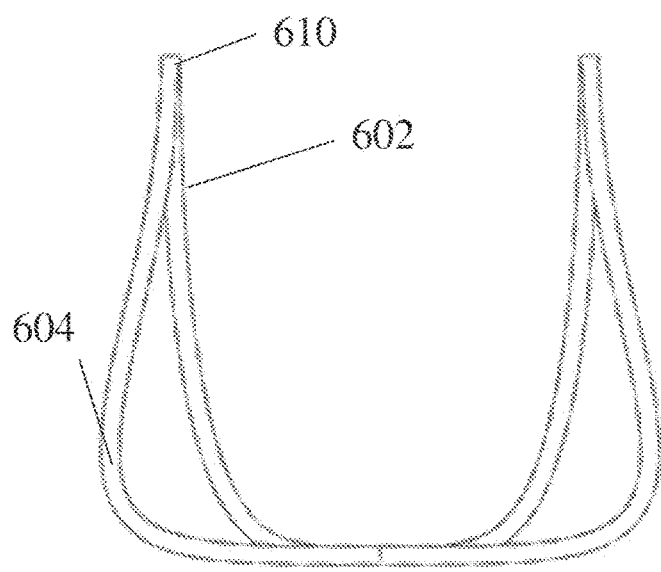
FIG. 16B is a front view of the frame of FIG. 16A.
Figure 16C:
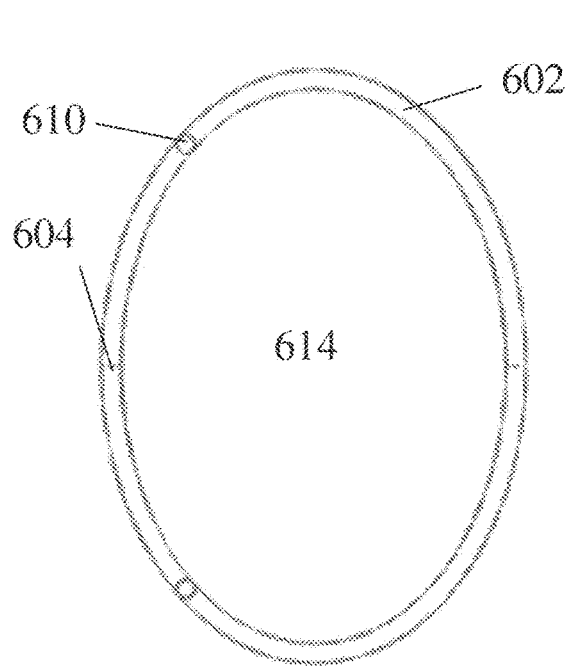
FIG. 16C is a top view of the frame of FIG. 16A.
Figure 16D:
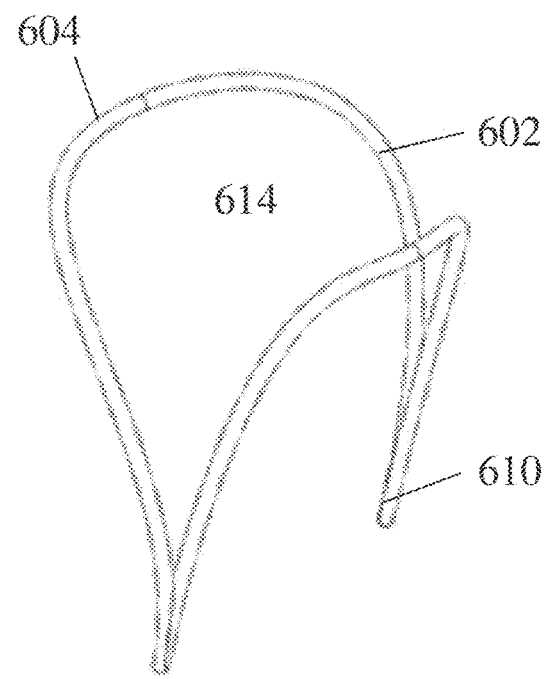
FIG. 16D is an inverted perspective view of the frame of FIG. 16A.

FIGS. 10, 11A, and 11B show another embodiment of the frame. In this embodiment, as the frame 202 expands, the frame sections 204 lengthen and separate from each other to increase the size of opening 214. 202' shows frame 202 after some expansion. Frame section 204 represents the location and shape of the frame section prior to expansion and 204' represents the location and shape of the frame section after some expansion. In some embodiments, the height of commissural posts 210 and the height of entire frame overall is maintained as the opening diameter increases.

For devices having elongating frame perimeter lengths, in some embodiments, the leaflets are configured to increase in size as the opening diameter increases. For example, in some embodiments, the leaflets may be sutured to the frame sections with extra material folding up like an accordion between sutures. As the frame sections expand, the distance between the sutures expand, unfolding the accordion like folds, providing additional sections of leaflet to accommodate the lengthening. In other embodiments, the leaflets are sutured normally to the frame sections, but the leaflets are particularly flexible or distensible and simply stretch as the frame sections expand.

While the depicted embodiments depict a symmetrical valve frame having a circular opening and frame sections that expand evenly, it should be understood that the current disclosure is not limited as such. In other embodiments of the device, the opening may be elliptical or otherwise irregular in shape to accommodate different structural environments and physiological valve applications.

FIGS. 12, 13A, 13B, and 13C show an embodiment of the frame where the two frame sections expand asymmetrically. Frame 302 begins with commissural posts 310 at one height, then after expansion, frame 302' has commissural posts 310' at a reduced height due to expansion. In these embodiments, the commissural posts 310 or the frame sections 304 may be unequal in some way to produce asymmetric expansion. They may be flared inwards between or equal to 5 degrees to 45 degrees, flared outwards between or equal to 45 degrees, could be of unequal heights prior to valve frame expansion, could have different thicknesses, or could be comprised of materials with differing stiffnesses. Regardless, when the frame 302 attempts to expand with the vasculature, the two frame sections separate laterally at different rates, creating an elliptical opening 314.

FIGS. 14A to 14D show an embodiment of the frame 402 and leaflets 406 defining an elliptical opening. In this embodiment, frame sections 404 are wider than in previous embodiments to produce an elliptical shape from the top view as seen in FIG. 14B. Commissural posts 410 are located at opposite sides along the major axis of the ellipse formed by the opening of the device. As the frame sections diverge, the opening of the device may remain coplanar with the perpendicular cross-section of the surrounding vasculature. While the figure shows commissural posts of equal heights, in some embodiments, the commissural posts may have unequal heights, or could be flared inwards or outwards 5-45 degrees. In some embodiments, the valve replacement device may be used as an inflow valve. In some embodiments, the valve replacement device may mimic the shape of a native atrioventricular valve.

FIGS. 15A to 15F show another embodiment of the frame 502 that defines an elliptical opening 514. In this embodiment, frame sections 504a and 504b are differently sized and or shaped from one another prior to valve frame expansion. As seen in FIG. 15B, only one of the commissural posts 510 are located on the major axis of the ellipse formed by the opening, while the other commissural post is located anterior to the major axis. Due to the different size and/or shape of the valve frame sections relative to one another, the leaflets of this embodiment are similarly different from one another to match their respective frame sections. In some embodiments, the leaflets could have the same mechanical properties as one another or could have different mechanical properties than one another to suit different applications. For example, the larger leaflet could be more extensible compared to the smaller leaflet to account for the size difference. In other embodiments, the commissural posts tilt axially relative to the surrounding vasculature. Embodiments with the tilted commissural posts can accommodate curved flow patterns through the device and enable preserved valve function in a variety of structural environments depending on the degree of the tilt. This tilting may give rise to an opening that does not sit in the same plane as the perpendicular cross-section of the lumen of the local vasculature.

FIGS. 16A to 16D show another embodiment of the frame 602 having frame sections 604. This embodiment has an asymmetric frame 602 that defines an elliptical opening 614. However, in this embodiment, both commissural posts 610 are located anterior to the major axis of the ellipse seen in FIG. 16C. Due to this arrangement, the frame 602 is asymmetric, resulting in one leaflet covering the majority of the opening.

In some embodiments, the plane formed by the opening could be orthogonal to the flow of fluid in the surrounding vasculature, or could be offset relative to the flow of fluid. In some embodiments, the plane formed by the opening may be coplanar with the perpendicular cross-section of the surrounding vasculature, or may be tilted relative to this perpendicular cross-section. For example, in the embodiment shown in FIG. 1A, the plane formed by the opening 114 of the device is coplanar with the perpendicular cross-section of the surrounding vasculature, which is vessel 112. In addition, the plane formed by the opening 114 is also orthogonal to the flow of fluid through vessel 112.

Figure 17:
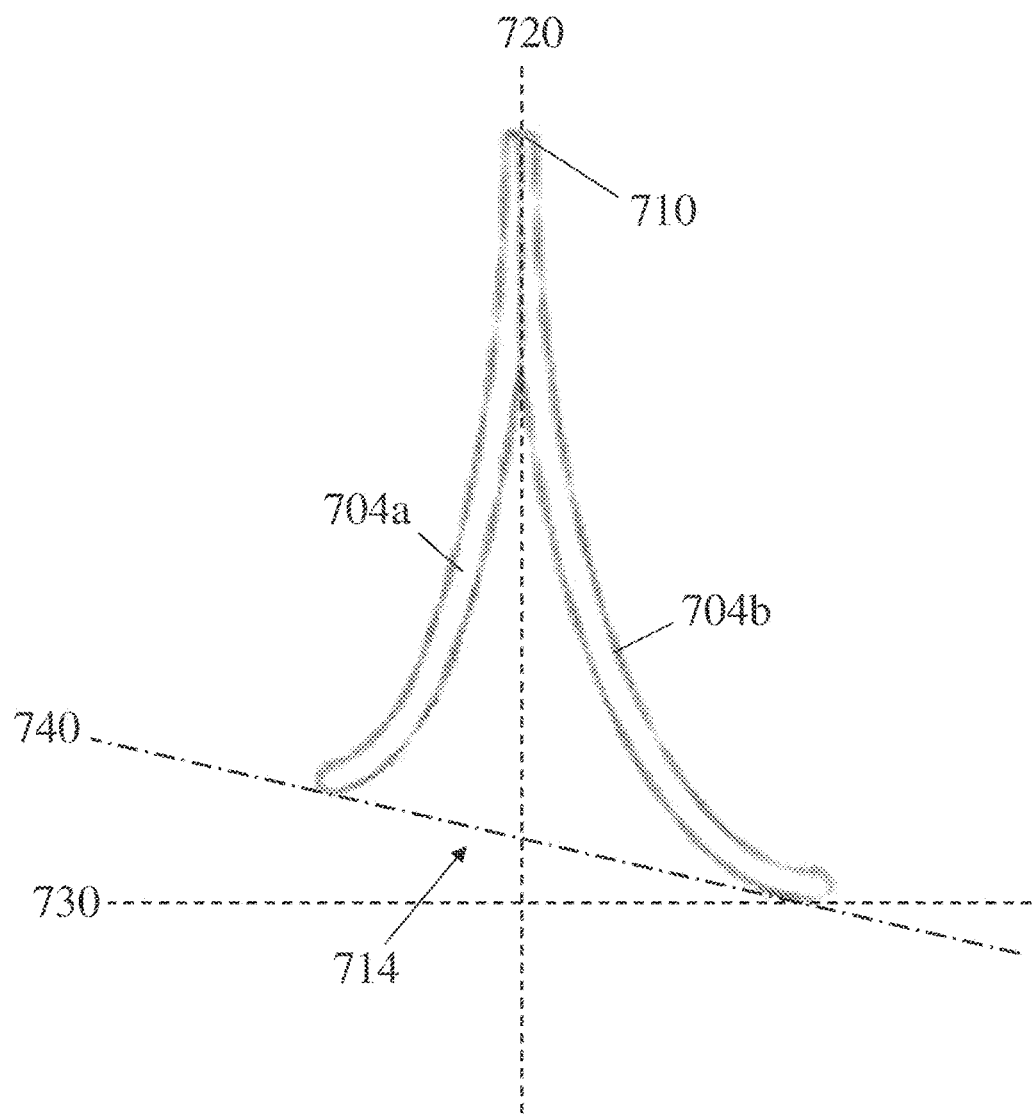
FIG. 17 is a side view of another embodiment of a valve frame section.

In some embodiments, the valve replacement device includes one or more commissural posts that extend in a direction defining a vertical. The plane formed by the opening could be orthogonal to the direction of the commissural posts, or may be tilted relative to the orthogonal. For example, in the embodiment shown in FIG. 1A, the plane formed by the opening 114 of the device is orthogonal to a vertical direction defined by the direction of the commissural posts 110. In contrast, the embodiment shown in FIG. 17, where the valve frame has sections 704a, 704b of different lengths, is an example of a tilted opening. The plane 740 defined by the opening 714 is not orthogonal to the vertical direction 720 defined by the direction of the commissural posts 710, but is instead, tilted to the orthogonal 730.

In some embodiments, the valve frame may be made up of more than one frame section. The frame section may form a U-shape having two arms extending away from the intermediate section forming a base of the first frame section. In some embodiments, the intermediate section lies on a single plane. For example, in the embodiment shown in FIGS. 1A and 1B, the valve frame has a frame section having an intermediate section 130 that lies on a single plane. This can also be seen in FIG. 4.

However, it should be appreciated that other arrangements are possible. For example, in some embodiments, the intermediate section could be non-planar, such that it is curved or otherwise shaped so that it does not lie along a single plane. In some embodiments, the intermediate section has a saddle-shaped curve, either facing up in the same direction in the U-shape, or down in an opposite direction as the U-shape.

Figure 18:
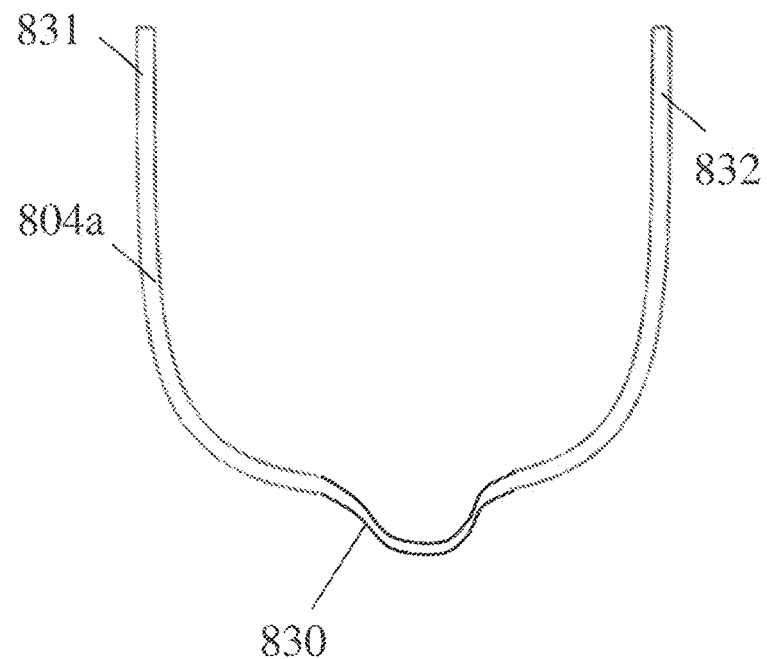
FIG. 18 is a front view of one embodiment of a valve frame section.
Figure 19:
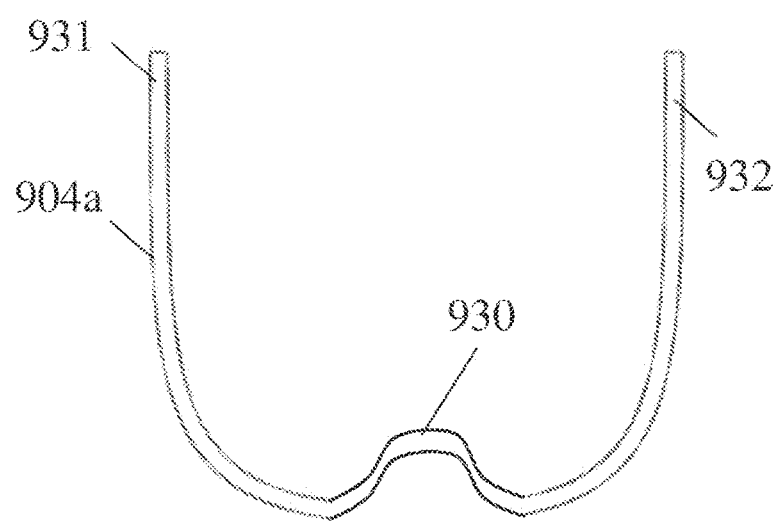
FIG. 19 is a front view of another embodiment of a valve frame section.

Two illustrative embodiments of valve frame sections with bases that are non-planar are shown in FIGS. 18 and 19. FIG. 18 is a front view of a valve frame section. The frame section 804a has a U-shape having a first arm 831 and a second arm 832 extending away from an intermediate section 830, which as a saddle-shaped curve that faces in the same direction as the U-shape. In the illustrative embodiment shown in FIG. 19, which is also a front view of a valve frame section, the frame section 904a has a U-shape having a first arm 931 and a second arm 932 extending away from an intermediate section 930, which has a saddle-shaped curve that faces in an opposite direction as the U-shape.

In some embodiments, the valve frames could be asymmetrically shaped or could expand asymmetrically due to flared or tilted commissural posts, or have different thicknesses or materials between the frame sections. The commissural posts may mirror one another with regard to size and/or shape, or they may be different from one another. The valve frame and two commissural posts may exhibit variable bending stiffness to allow for change in opening shape (i.e.

cylindrical opening becomes oval/elliptical under peak diastolic loads) during the cardiac cycle.

Figures 20A, 20B:
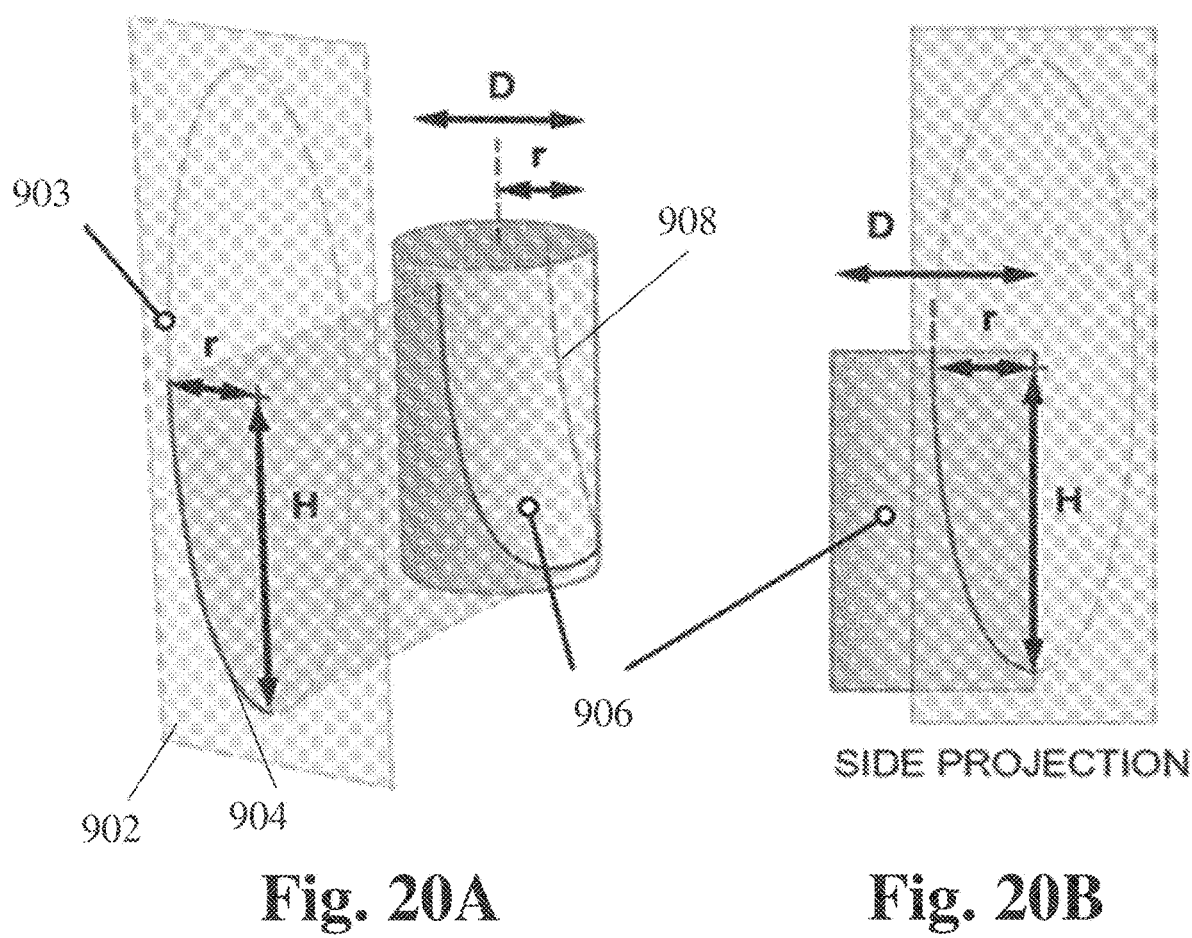
FIG. 20A is a perspective view graphical visualization of a plane containing an ellipse, and a cylinder, onto which a portion of the ellipse is projected, where the projected curve defines the curvature of one embodiment of a valve frame section.
FIG. 20B is a side view graphical visualization of the plane and cylinder of FIG. 20A.

FIGS. 20A and 20B show the curve profile of one of the frame sections of a valve frame of a valve replacement device according to some embodiments. In this embodiment, the curve profile 908 may be approximately defined by projecting an elliptical quadrant 904 from plane 902 on to a cylinder 906, which could represent the inner wall of a representative vessel. The ellipse profile 903 may have a semi-major axis length equivalent to the height of the frame (H) and a semi-minor axis having a length equivalent to radius (r) of the frame. The cylinder may have a radius equivalent to that of the frame opening. The projected ellipse co-vertex can be coincident with the cylinder centerline, the ellipse vertices, and the ellipse center such that they are all coincident with the outer edge of a central cross-section of the cylinder when viewing from the side view of FIG. 20B. In this configuration, a center of the ellipse from which the elliptical quadrant is derived coincides with a point along a circumference of an axial end of the cylinder, and a minor axis and a major axis of the ellipse are co-axial with edges of a cross-section of the cylinder.

The curve profile 908 can be mirrored about the center plane of the cylinder to generate the curve profile of the opposite frame section.

It is also contemplated that a compound curve or polynomial spline could be projected on to the cylinder to generate the curve profile of the full frame.

Figure 21:
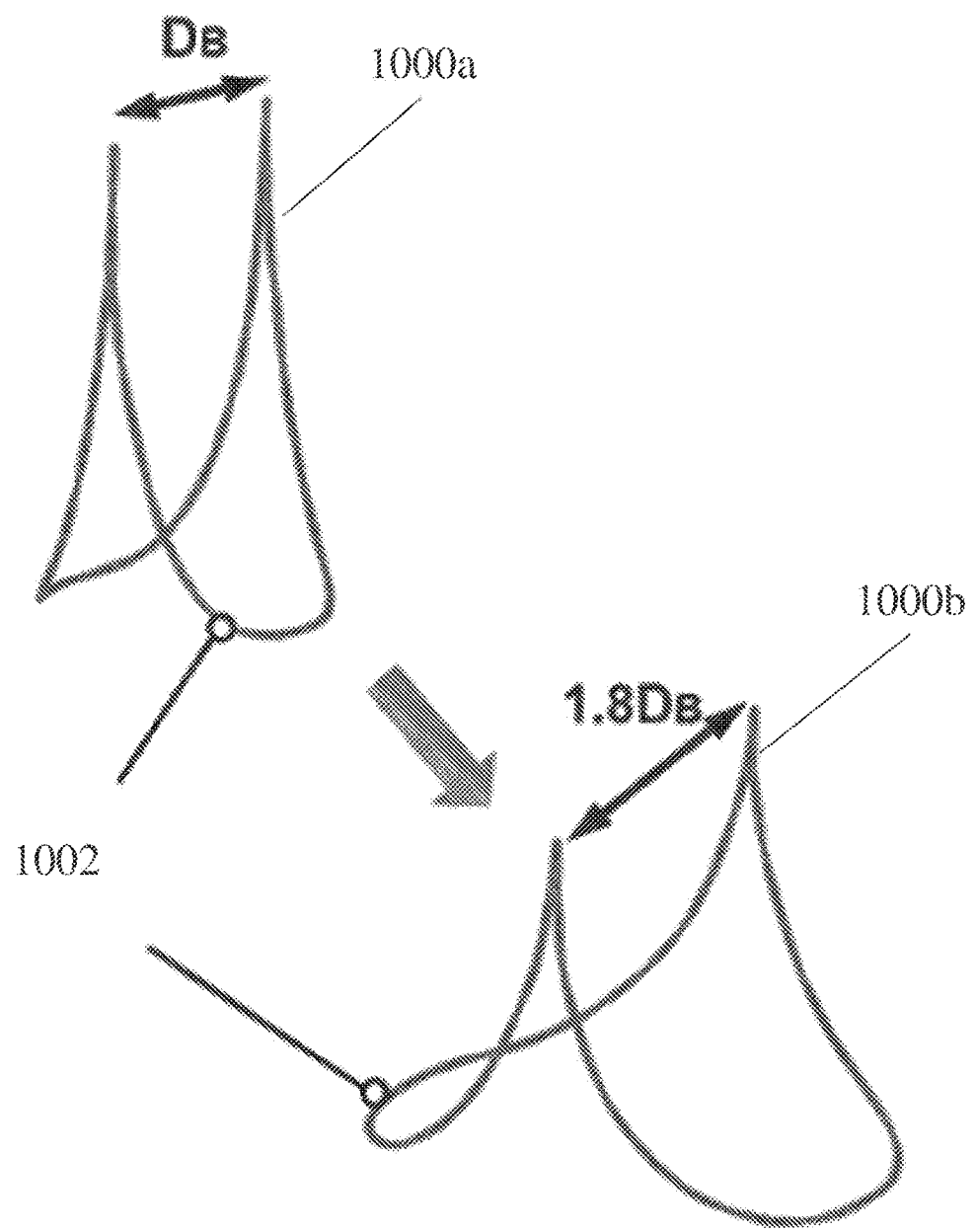
FIG. 21 is a perspective view of one embodiment of a valve frame of a valve replacement device according to one embodiment in a non-expanded state and in an expanded state.
Figure 22:
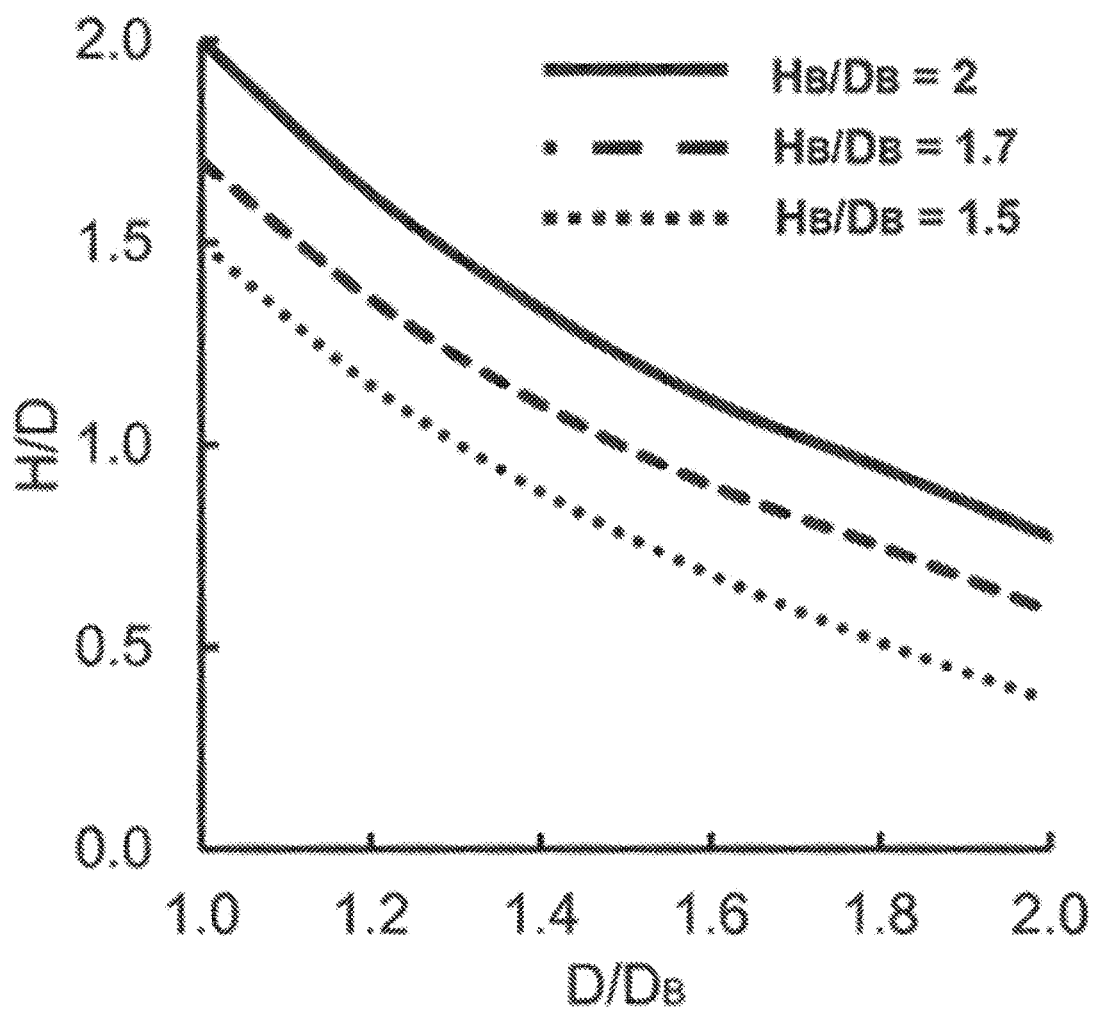
FIG. 22 is a line graph showing the height/diameter ratios of different embodiments of a valve frame of a valve replacement device with different baseline height to diameter ratios over the course of expansion.

FIG. 21 shows one embodiment of a valve frame of a valve replacement device at two different states: an unexpanded state 1000a and an expanded state 1000b. In this embodiment, the length of the valve frame 1002 is held constant during expansion of the valve frame. Instead of elongating the actual length of the valve frame, radial growth of the frame is accommodated by a reduction in valve frame height. FIG. 22 shows a line graph depicting how the height-to-diameter ratio (H/D) for embodiments of the valve frame, with differing baseline height to diameter ratios (HB/DB), change as the device expands from the baseline diameter DB to the final diameter 2DB. While embodiments with baseline HB/DB ratios of 2, 1.7 and 1.5 are shown, other ratios are also contemplated as described above.

One embodiment of the valve replacement device was subjected to hydrodynamic performance testing. The valve replacement device was tested at five different expansion states of the valve frame (16 mm, 19.2 mm, 22.4 mm, 25.6 mm, and 28.8 mm). FIG. 23A is a bar and line graph that depicts both measured flow, regurgitation volumes and transvalvular pressure gradient (measurement of pressure drop across the valve during opening phase, systole) across a valve replacement device having the HB/DB=1.7 valve frame of FIG. 22, at different expansion states. It was the device exhibited unobstructed forward flow throughout expansion; as flow was increased to match the increasing valve diameter (to mimic physiologic conditions in a growing patient), the transvalvular pressure gradient (ΔP) did not increase with valve expansion.

Figure 23C:
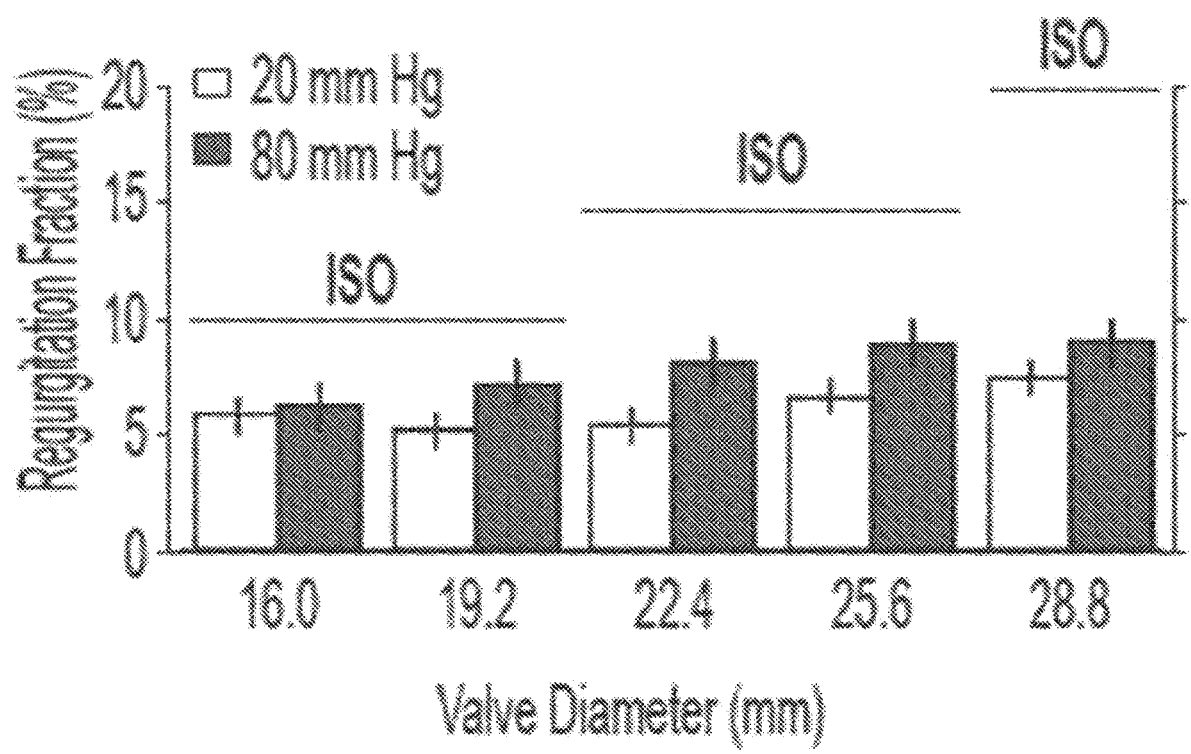
FIG. 23C is a bar graph showing regurgitant fraction at two different diastolic pressures (representing right and left heart conditions) for different opening diameters of a valve replacement device having the HB/DB=1.7 valve frame of FIG. 22.
Figure 23D:
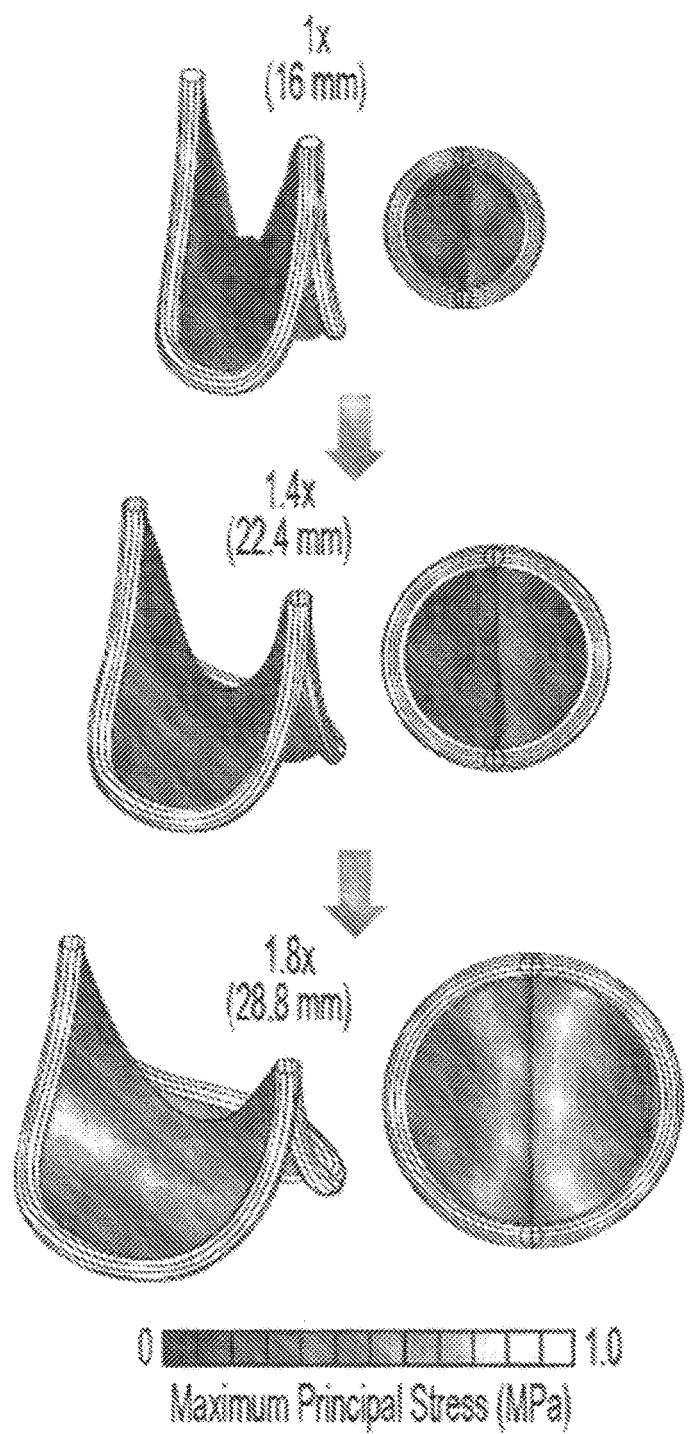
FIG. 23D shows simulated peak stresses (Maximal principal stress, MPa) under a load of 20 mmHg (approximation of right heart conditions) across leaflets of a valve replacement device having the HB/DB=1.7 valve frame of FIG. 22 when in the closed configuration, simulated using finite element analysis.

FIG. 23B shows a line graph depicting the change in flow characteristics over time as the valve replacement device opened and closed. Two valve sizes are depicted, 16 mm and 28.8 mm ID. FIG. 23C shows the regurgitant fraction measured at the various valve diameters at different diastolic pressures (i.e. pressure load on leaflets in closed state): 20 mmHg (represents physiologic right heart diastolic pressure) and 80 mmHg (represents physiologic left heart diastolic pressure). It was found that the device exhibited trivial valve leakage in the diastole condition across all states of expansion (i.e. 1× up to 1.8× ID). FIG. 23D shows the results of finite element analysis, conducted to evaluate magnitude and distribution of stresses on the growth-accommodating valve in the loaded state (i.e. leaflets in closed position). Data presented demonstrates peak stresses (Maximal principal stress, MPa) under 20 mmHg of loading pressure. The data showed that the magnitude of peak stresses on the valve leaflets in the closed state were relatively low throughout expansion from 16 mm to 28.8 mm (from 1 times to 1.8 times the baseline diameter). Much of the stress was distributed at the location of highest deformation, and no stress was concentrated at the site of the leaflet-frame attachment. Further, there was relatively low stresses at the frame commissures, which represents a departure from traditional 3-leaflet bio-prosthetic valve designs known in the art.

FIGS. 24A, 24C, 24E, and 24G show the results of in vivo testing conducted by implanting one embodiment of the valve replacement device with a 14 mm internal diameter in four lambs. FIGS. 24B, 24D, 24F, and 24H show the results of in vivo testing where the same embodiment of the valve replacement device expanded to 25 mm (1.8 times baseline diameter) and implanted in four adult sheep. In these studies, the valve replacement devices were used to replace the pulmonary valve of the lambs and sheep. FIGS. 24C and 24D show the measured change in the right ventricular (proximal to the valve) and pulmonary artery pressure (distal to the valve), over the course of the cardiac cycle of the animals. It was found that regardless of the valve expansion state, there was no transvalvular gradient across the valve. FIGS. 24E and 24F show representative flow waveforms of measured physiological flow across the valve replacement devices over the course of the cardiac cycle. It was found that regardless of the diameter of the opening, forward flow of the physiological fluids were unobstructed, and there was no leakage across the valve replacement devices in diastole. FIGS. 24G and 24H show echocardiograms conducted to visualize the implanted valve replacement devices in vivo. The changes in frame height and leaflet coaptation height at different states of valve diameter expansion become apparent between the two animal groups.

FIGS. 25A-D show one embodiment of the valve frame of a valve replacement device. In this embodiment, the valve frame 2500 includes a top reinforcement features such as a reinforcement strut 2504 attached to the commissures 2502 of the frame. The device also includes lower reinforcement strut 2506 connecting the lower portions of the frame sections. In this embodiment, top reinforcement strut 2504 has an circular profile in the fully expanded state, and attaches to the commissures at diametrically opposed points of the annulus. The top reinforcement strut of this embodiment includes undulations 2508 that serve to reduce the diameter of the top reinforcement strut when the feature is in an unexpanded state. As the frame expands, the pair of commissures separate, increasing the distance between the pairs of commissures and applying an expanding stress to the top reinforcement strut. The undulations permit the top reinforcement strut to expand with the feature by straightening out the undulations. The total length of the reinforcement strut may be equal to or larger than the largest possible circumference of the opening to ensure that the frame can expand to the largest possible circumference without limiting expansion, obstructing the valve opening, or distorting the geometry of the leaflet attachment frame.

Figure 25A:
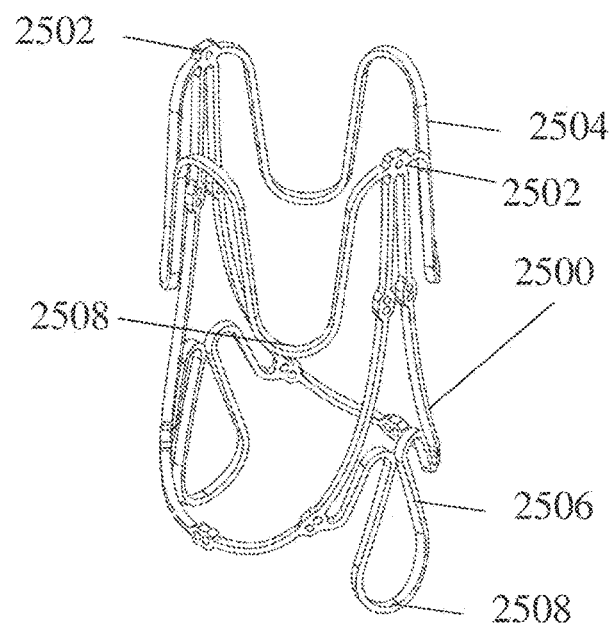
FIG. 25A is a perspective view of one embodiment of a valve frame of a valve replacement device.
Figure 25B:
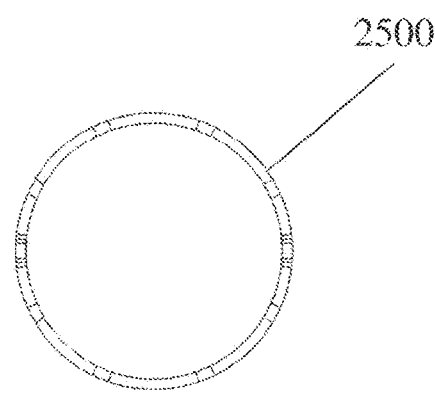
FIG. 25B is a top view of the valve frame of FIG. 25A.
Figure 25C:
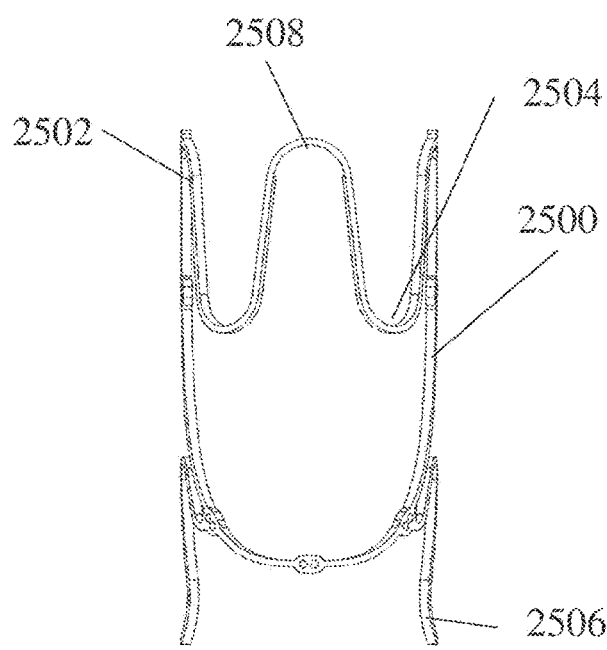
FIG. 25C is a front view of the valve frame of FIG. 25A.
Figure 25D:
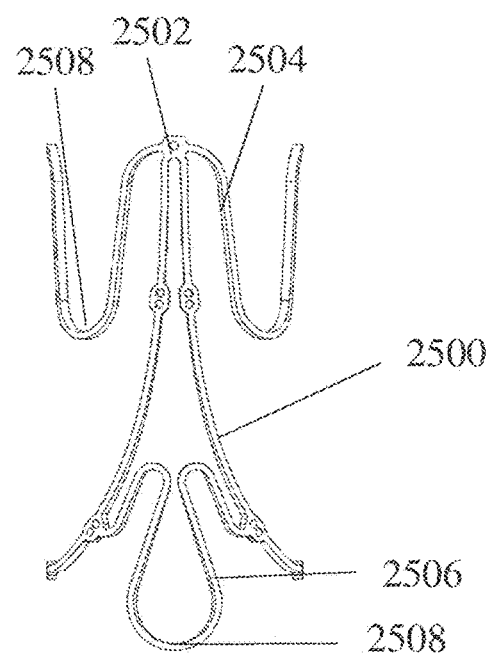
FIG. 25D is a side view of the valve frame of FIG. 25A.

While an annular top reinforcement strut with undulations is depicted in FIGS. 25A, 25C, and 25D, it should be understood that any shape or arrangement that connects the commissures of the frame sections while allowing the frame to expand is also contemplated. For example, instead of an annular shape, the top reinforcement strut could be elliptical, diamond-shaped, or polygonal, or could comprise separate connecting portions instead of one continuous closed loop. The top reinforcement strut could also have a telescoping design, be made of an elastic material that can be reversibly deformed when the reinforcement strut is expanded, or simply have more or fewer or larger or smaller undulations than depicted in the figures.

FIG. 26 shows an attachment zone 2600 for the top reinforcement strut. In some embodiments, the top reinforcement strut is attached to the valve frame within the top 30% of height of the commissure. However, it should be understood that other embodiments where the top reinforcement strut is attached outside of the top 30% zone of the device are also contemplated.

In some embodiments, the top reinforcement strut is attached to the frame at or near the top of the pairs of commissures.

Lower reinforcement strut 2506 as depicted in the embodiment of FIGS. 25A-D includes undulation 2508 that allows the lower support feature to have a smaller diameter when the valve frame is in its non-expanded configuration. As the frame sections separate when the valve diameter increases, the undulation straightens out, expanding the diameter of lower reinforcement strut 2506 to allow the lower feature to expand with the frame.

While a lower reinforcement strut with a distinct tear drop shape extending below the frame of the device is depicted, the lower feature could be of any shape that allows the lower feature to help maintain the desired geometric profile of the leaflet attachment frame across expansion state. The lower reinforcement strut may also be used as a fixation site for transcatheter deployment, or for attachment to native heart structures, or for other applications. For example, the lower support feature could have a telescoping design, be made of an elastic material that can be reversibly deformed when the feature is expanded, or simply have more or fewer or larger or smaller undulations.

Figure 27:
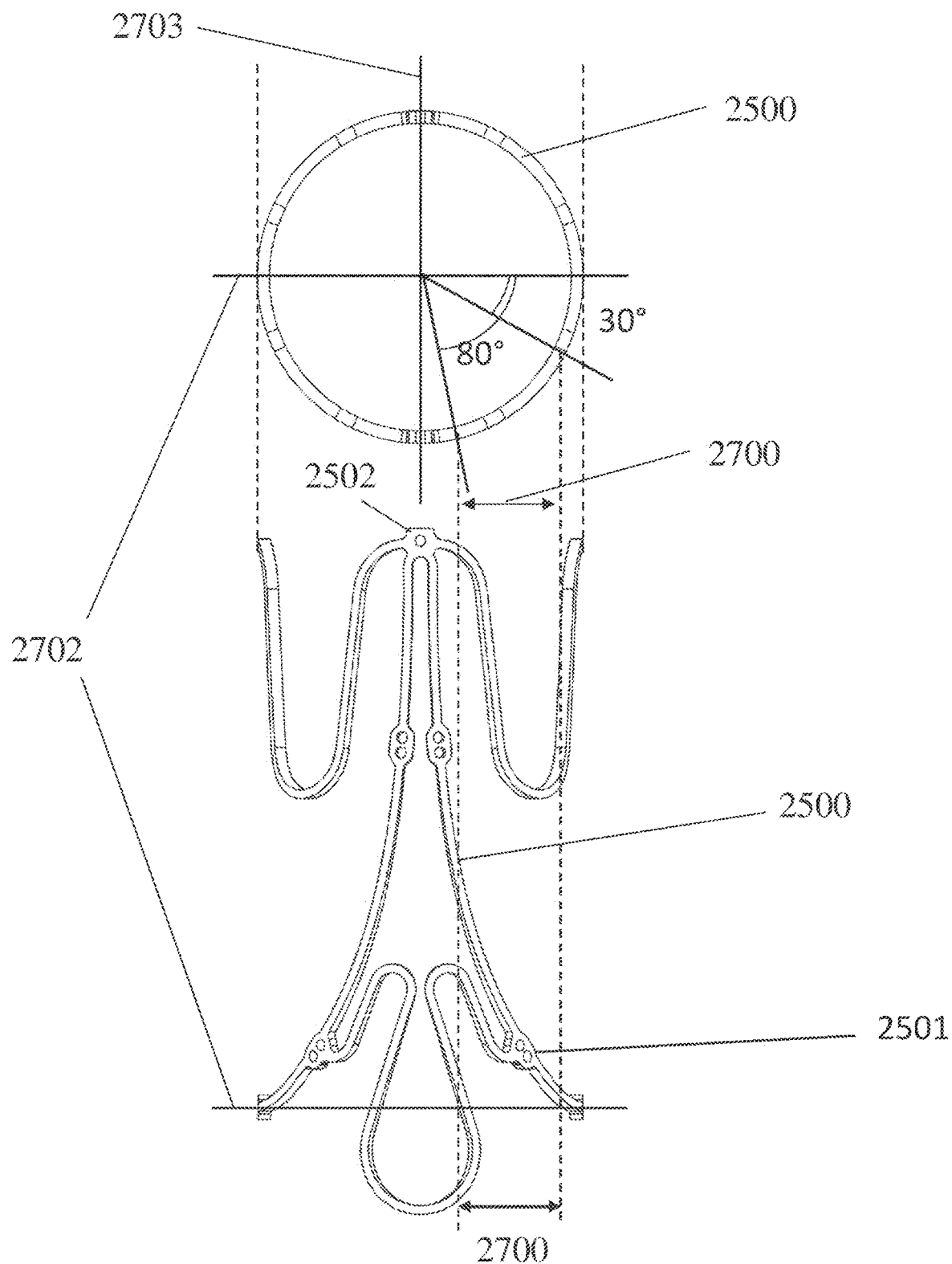
FIG. 27 shows top and side views of one embodiment of a valve frame of a valve replacement device, annotated to depict an attachment zone for a bottom reinforcement strut.

FIG. 27 shows an attachment zone 2700 for the lower reinforcement strut. FIG. 27 shows a top view of the valve frame from FIG. 25B, imposed over the side view from FIG. 25D. Line 2702 is an imaginary axis that passes through the diameter of the opening and is perpendicular to an imaginary line connecting the tops of the two commissures of the valve frame. When viewing the top view, if line 2702 were the x-axis and the perpendicular line 2703 were the y-axis, assuming 0° begins on the right intersection between line 2702 and the frame (at 0° of a unit circle) and opens counter clockwise, attachment zone 2700 is between 280° and 330°. As seen in FIG. 27, the 280° to 330° corresponds to the lower portions of the arc of the frame sections as seen in the side view. In some embodiments, the lower feature is attached at 310°, as represented by point 2501.

It should be understood that other embodiments where the lower reinforcement strut is attached outside of the attachment zone 2700 of the device are also contemplated.

Figure 28:
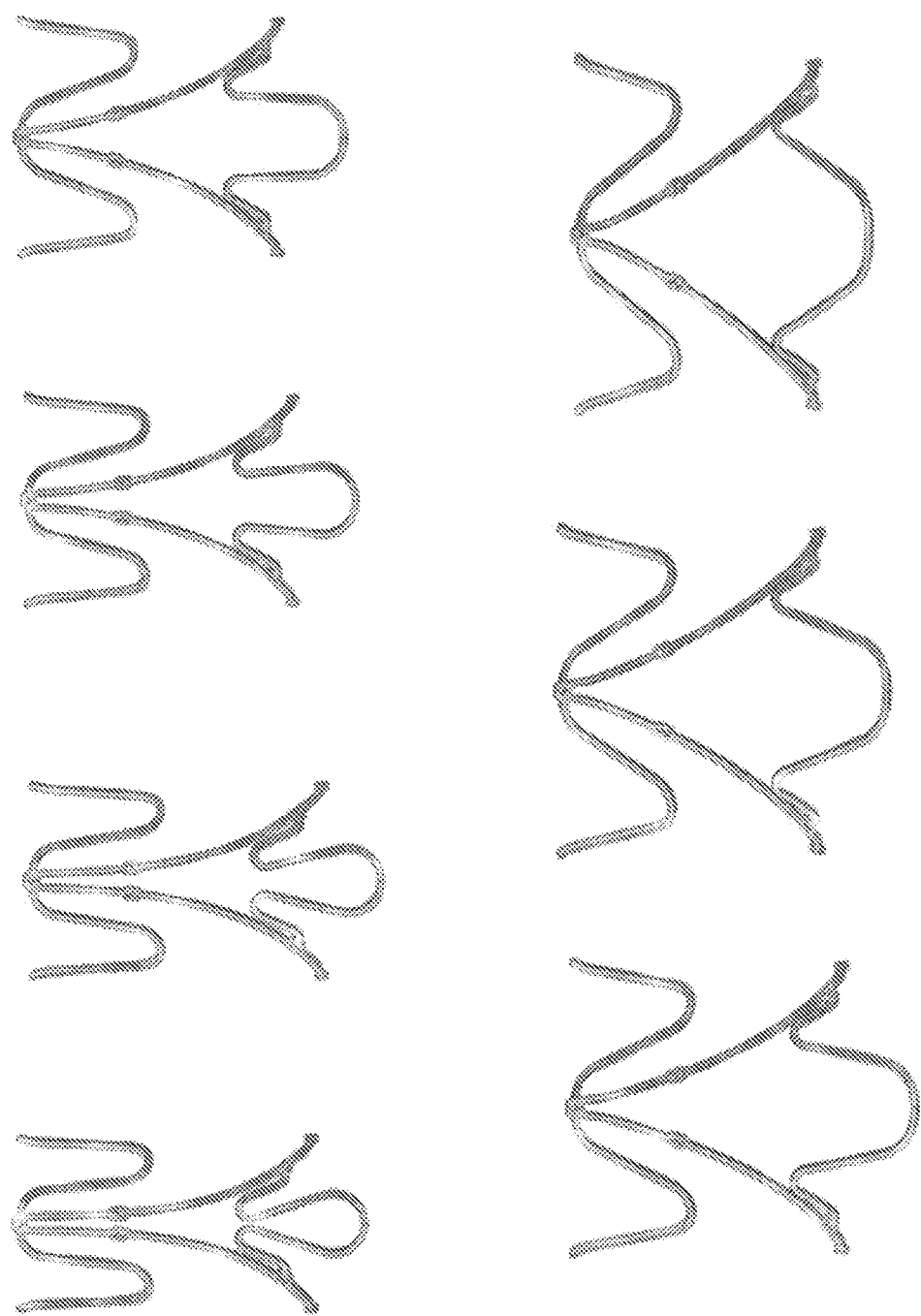
FIG. 28 shows side views of the valve frame of FIG. 25A expanded to progressively larger opening diameters.

FIG. 28 shows side views of the valve frame of FIG. 25A at different expansion sizes (12.7 mm, 14 mm, 16 mm, 18 mm, 20 mm, 22 mm, and 24 mm respectively).

Figure 29:
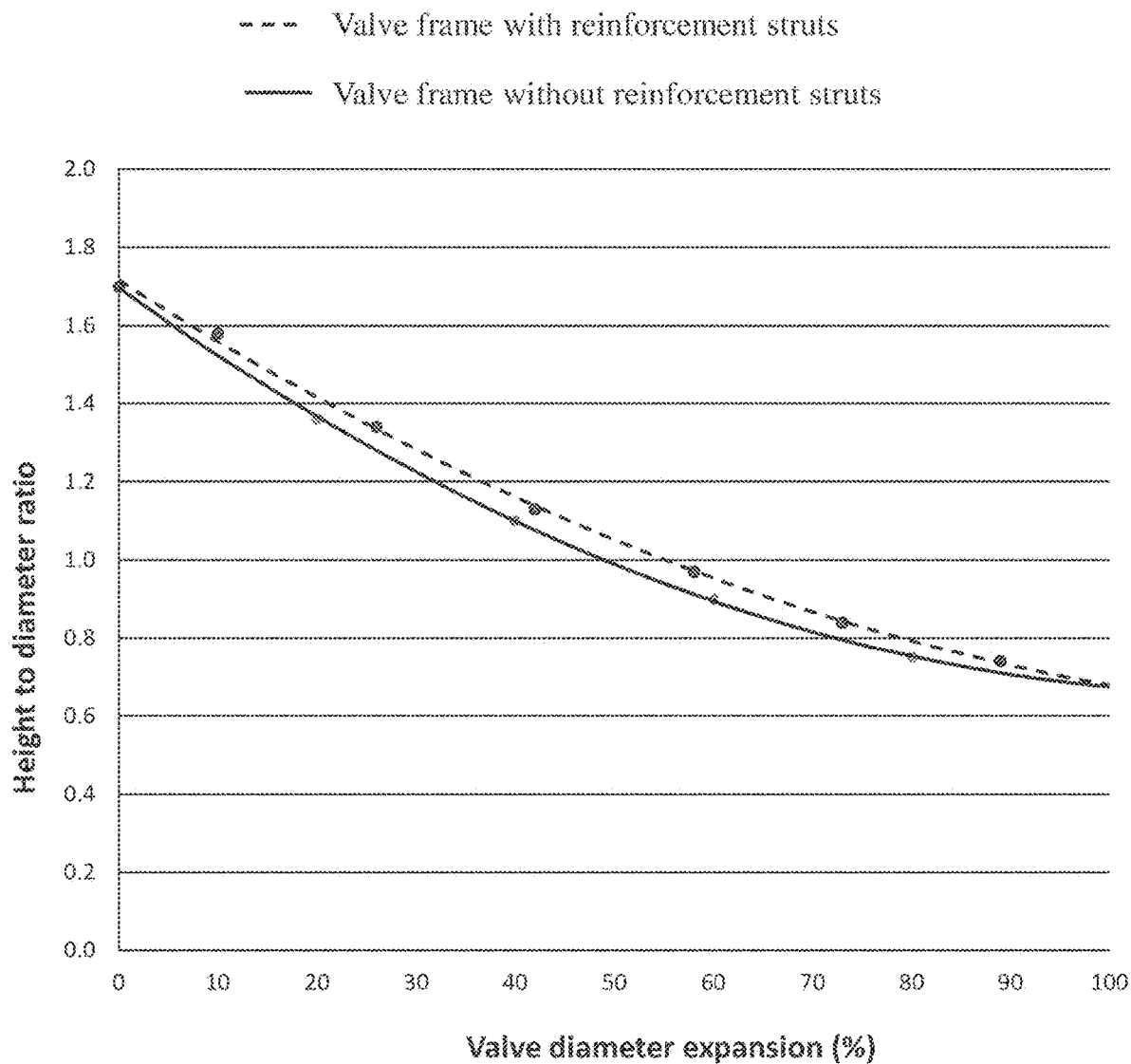
FIG. 29 is a scatter plot showing the height to diameter ratio of a valve replacement device having the valve frame of FIG. 25A compared to an embodiment of a valve replacement device that does not include reinforcement struts at the valve frame.

FIG. 29 shows a graph depicting how the height to diameter ratio of the embodiment of FIGS. 25A-D having reinforcement struts, and the embodiment of FIG. 21, which does not have reinforcement struts, changes with expansion of valve diameter. The embodiment with reinforcement struts was expanded via balloon expansion, while the embodiment without reinforcement struts was expanded in simulation in 20% increments. The solid line represents the behavior of the valve replacement device without reinforcement struts (e.g. FIG. 21), while the dashed line represents the behavior the valve replacement device of FIG. 25A-D with both a top and lower reinforcement strut. The devices each have a baseline height to diameter ratio of 1.7:1 and were expanded to double their baseline diameter. It was found that the devices both achieve a very similar kinematic profile of an expanding valve frame in which the height to diameter ratio decreases as the valve frame diameter increases.

Figures 30A, 30B:
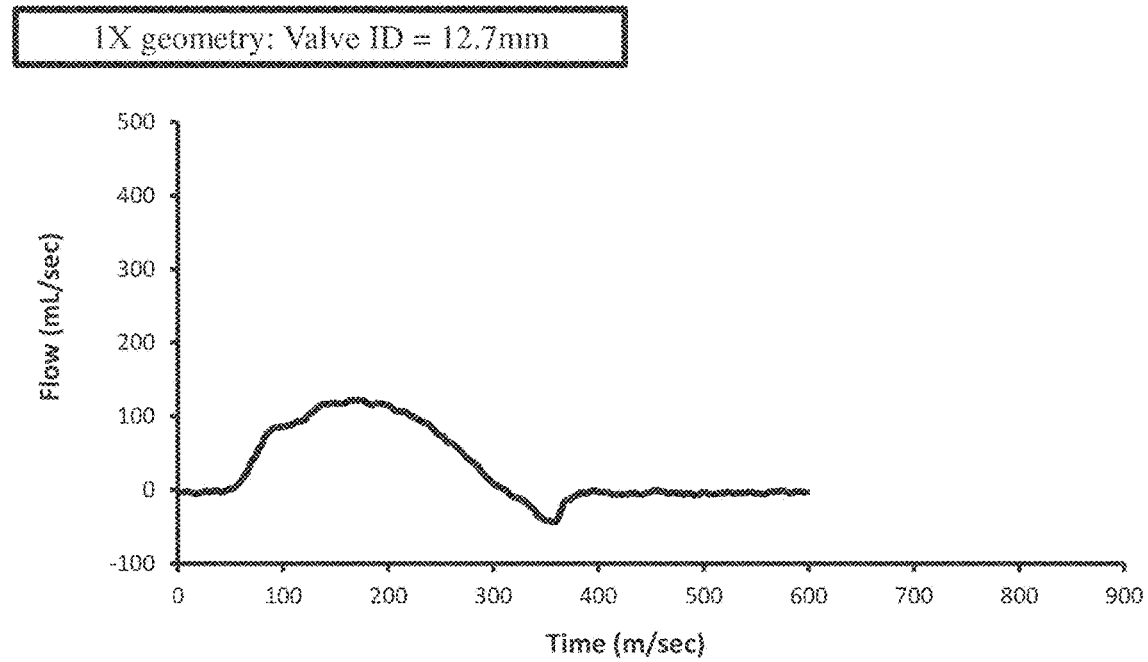
FIG. 30A is a line graph showing flow waveform and regurgitation volumes over the course of a simulated circulatory flow loop, through the valve replacement device of FIG. 25A, at baseline diameter, during in vitro hydrodynamic testing.
FIG. 30B is a table containing data obtained over the course of the in vitro testing of a valve replacement device having the valve frame of FIG. 25A, at baseline diameter.
Figures 31A, 31B:
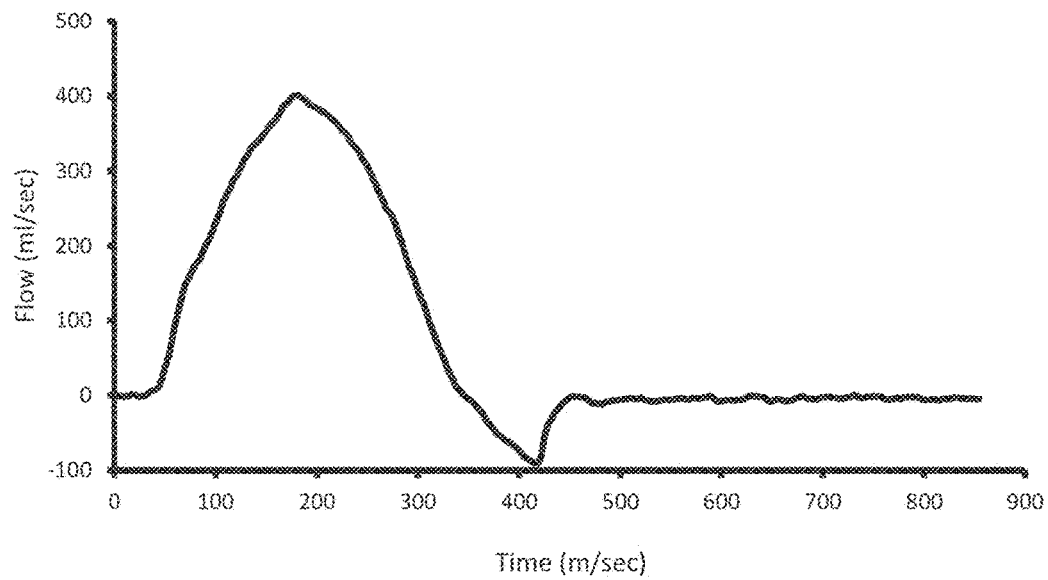
FIG. 31A is a line graph showing flow waveform and regurgitation volumes over the course of a simulated circulatory flow loop, through a valve replacement device having the valve frame of FIG. 25A, at an expanded size of 1.8 times the baseline diameter, during in vitro hydrodynamic testing.
FIG. 31B is a table containing data obtained over the course of the in vitro testing of a valve replacement device having the valve frame of FIG. 25A, at an expanded size of 1.8 times the baseline diameter.

FIGS. 30A-B and FIG. 31A-B show the results of in vitro hydrodynamic performance testing of a valve replacement device having the valve frame of FIG. 25A-D. A functional prototype of the device was tested in a sophisticated mock circulatory flow loop at various states of expansion. The device was tested at its baseline configuration (12.7 mm internal diameter, 1×), then expanded with a balloon catheter to 23 mm internal diameter (1.8×) and re-tested under physiologic pressure and flow conditions. FIG. 30A shows the flow profile across the device at an opening diameter of 12.7 mm over the course of a cardiac cycle. FIG. 30B shows other measured values including the transvalvular pressure gradient across the valve, fluid flow profile through the device, including the leakage volume and the regurgitant fraction. FIG. 31A shows the flow profile across the device at 1.8 times the baseline diameter (23 mm) over the course of the cardiac cycle. FIG. 31B reflects the same types of measurements as FIG. 30B but for the device at an expanded state of 23 mm in opening diameter. It was found that valve functionality remained unchanged at each tested valve diameter.

Figure 32C:
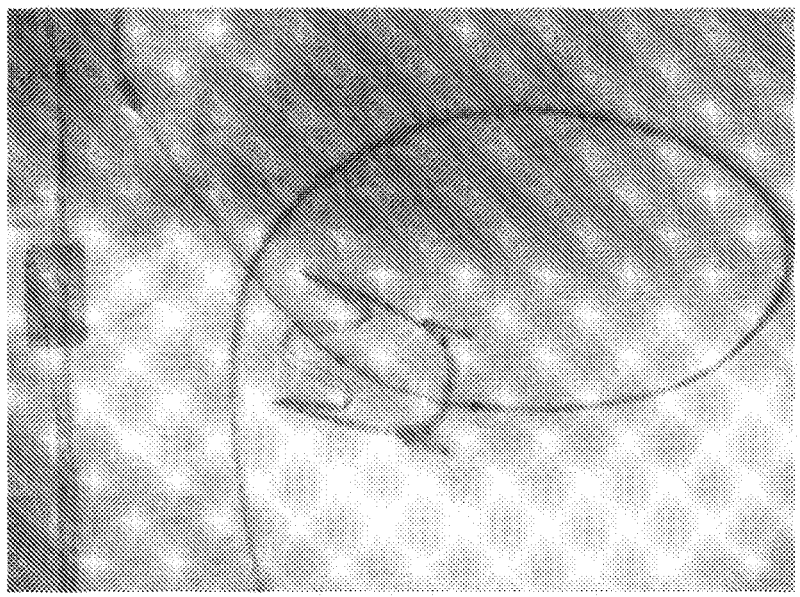
FIG. 32C is an x-ray radiograph of the valve replacement device of FIG. 32A in a partially expanded configuration.
Figure 32B:
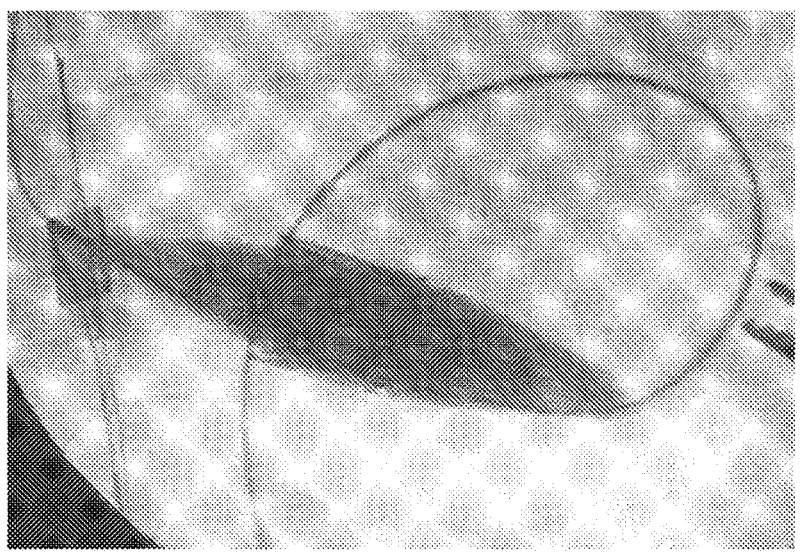
FIG. 32B is an x-ray radiograph of the valve replacement device of FIG. 32A in the process of transcatheter balloon dilation.
Figure 32A:
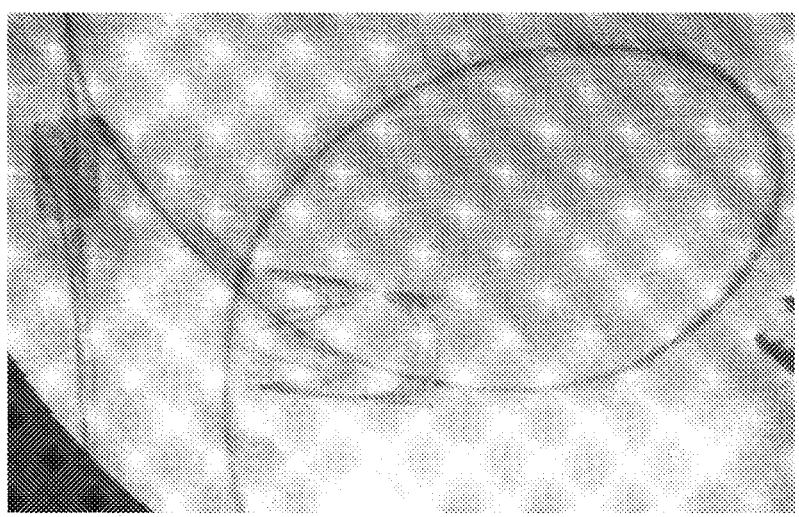
FIG. 32A is an x-ray radiograph of the valve replacement device according to one embodiment implanted in a 25 kg sheep.

FIGS. 32A-32C show the valve replacement device according to one embodiment implanted in a 25 kg sheep. The unexpanded (12.7 mm) valve replacement device was implanted in the pulmonary valve position in 25 kg sheep. The device was dilated to 16 mm, 18 mm, and 20 mm using transcatheter balloon dilation. FIG. 32A shows the device dilated to 16 mm, FIG. 32B shows the dilation process, and FIG. 32C shows the device post dilation of FIG. 32B at 18 mm. It was found that the valve geometries (the leaflet attachment line and reinforcement struts) matched the geometric profiles pre and post expansion. The valve successfully expanded under radial force generated by clinical standard balloon catheter in an implanted in vivo setting using balloon pressure recommended by the balloon manufacturer, and the valve frame maintained its structural integrity after multiple sequential dilations.

FIGS. 33A-33D show an alternative embodiment of a valve frame 3200 with a shortened lower reinforcement strut 3206. In this embodiment, the lower reinforcement strut undulations has a shorter tear drop shaped undulation trough 3208 that does not extend past the bottom of the valve frame.

FIG. 34A-34D show an alternative embodiment of a valve frame 3300 with a plurality of holes 3303 along the frame of the device. It is contemplated that having holes along the frame provide anchoring points for suturing the leaflets to the frame. It should be understood that any number of holes, spaced any distance from each other, of any size, could be used. The holes may not be formed directly into body of the frame but may instead be formed in sections that stem off of the frame body.

FIGS. 35A-35D show an alternative embodiment of a valve frame 3400 including middle reinforcement struts in addition to top reinforcement struts 3402 and lower reinforcement strut 3406. In this embodiment, the middle reinforcement strut 3410 may have two semi-annular portions that connect the two frame sections. The portions of the middle reinforcement strut 3410 may include undulations 3412 that may reduce the size profile of middle attachment feature. Similar to the top and lower reinforcement struts, the undulations can straighten out to allow the middle reinforcement strut to expand with the frame. The middle reinforcement strut may have a length that is equal to or greater than the perimeter of the opening at maximum expansion.

Figure 36A:
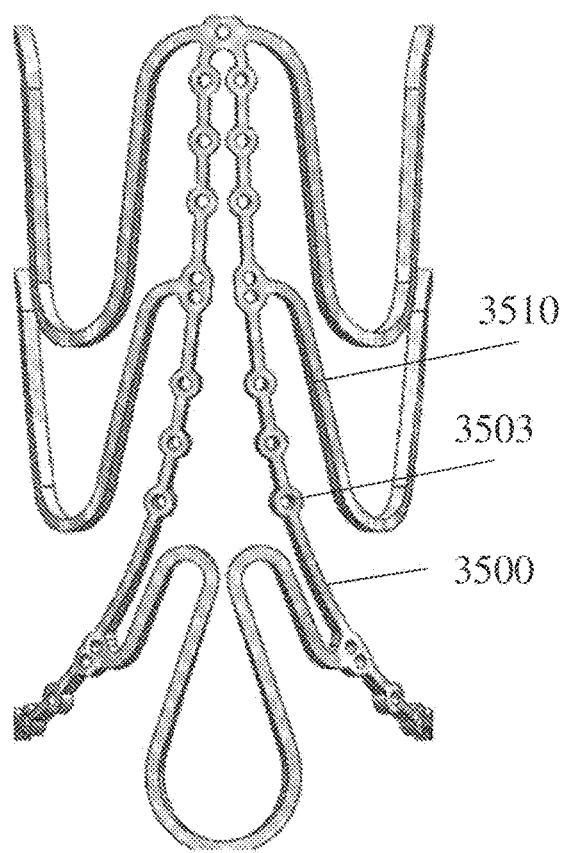
FIG. 36A is a side view of one embodiment of a valve frame of a valve replacement device.
Figure 36B:
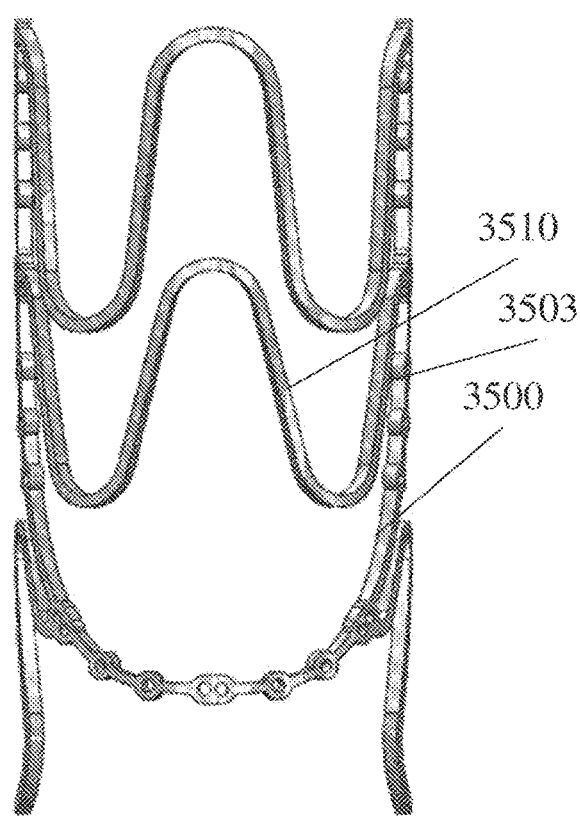
FIG. 36B is a front view of the valve frame of FIG. 36A.

FIG. 36A-36B show an alternative embodiment of a valve frame 3500 with the plurality of holes 3503 along the frame of the device that may provide anchoring points for suturing the leaflets to the frame, as well as a middle reinforcement strut 3510 to aid in reinforcement of the frame.

While embodiments have been depicted with no reinforcement struts or one or more of a top, middle, and lower reinforcement strut, it should be understood that contemplated embodiments could have any number of reinforcement struts located in any number of locations. The reinforcement struts may serve to allow the frame to expand to their fully expanded diameters while providing structural support to the frames such that the geometry of the expanded frame allows for preserved valve function (e.g. unobstructed forward flow and no or minimal regurgitation).

In some embodiments, the reinforcement struts and/or valve frame may be constructed from SS-316L or CoCr-MP35N, or any other material with sufficient stiffness to provide structural integrity to the device, while being ductile enough to allow undulations to straighten with valve frame expansion, or to otherwise allow other expanding designs to expand with the valve frame expansion. The reinforcement struts may have widths and wall thicknesses identical to those of the frame, or may be thicker or thinner than the frame.

In some embodiments, the reinforcement struts can be laser cut, stamped, or otherwise cut from a single sheet of material. In other embodiments, the reinforcement struts need not be formed from a single piece of material. For example, a reinforcement strut can be made of a combination of different materials, e.g. by joining one piece of material to another piece of material. A reinforcement struts may have a uniform or non-uniform thickness.

Figure 33A:
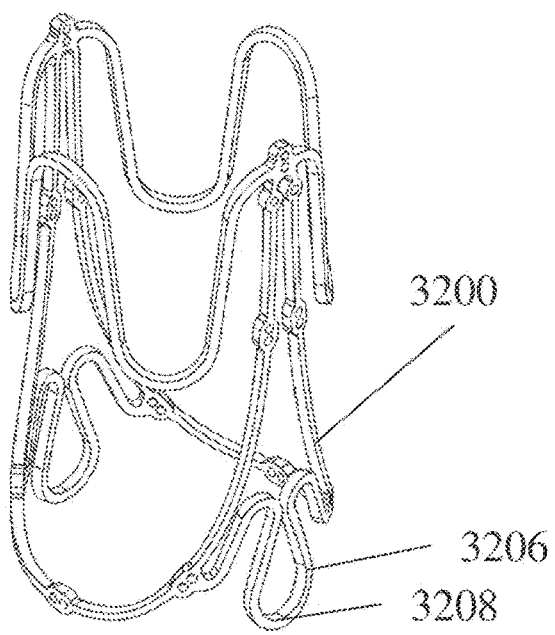
FIG. 33A is a perspective view of a valve frame of a valve replacement device according to one embodiment.
Figure 33B:
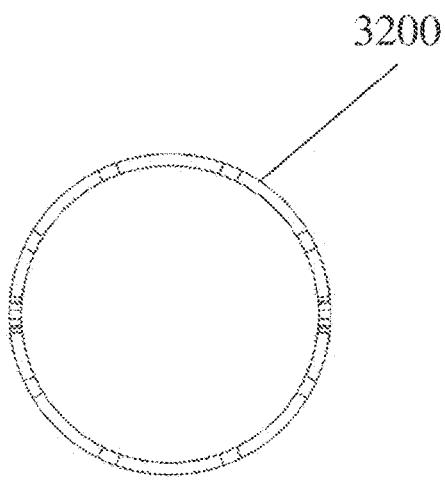
FIG. 33B is a top view of the valve frame according to the embodiment of FIG. 33A.
Figure 33C:
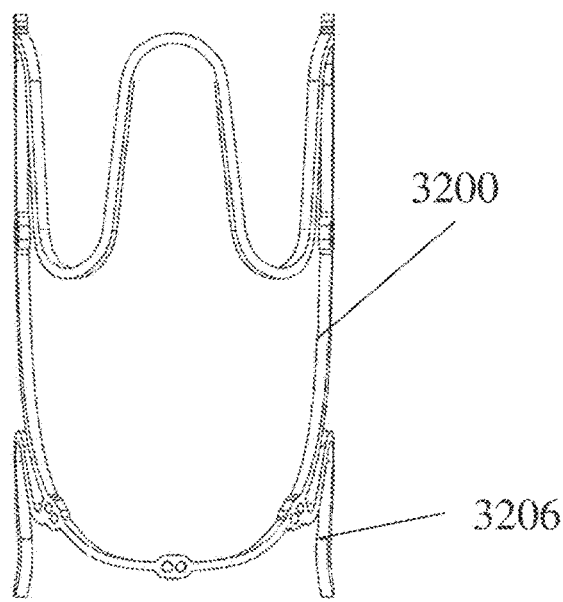
FIG. 33C is a front view of the valve frame according to the embodiment of FIG. 33A.
Figure 33D:
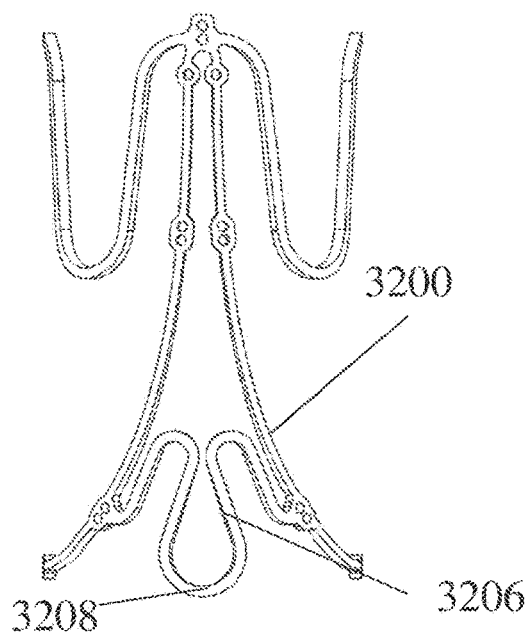
FIG. 33D is a side view of the valve frame according to the embodiment of FIG. 33A.
Figure 34A:
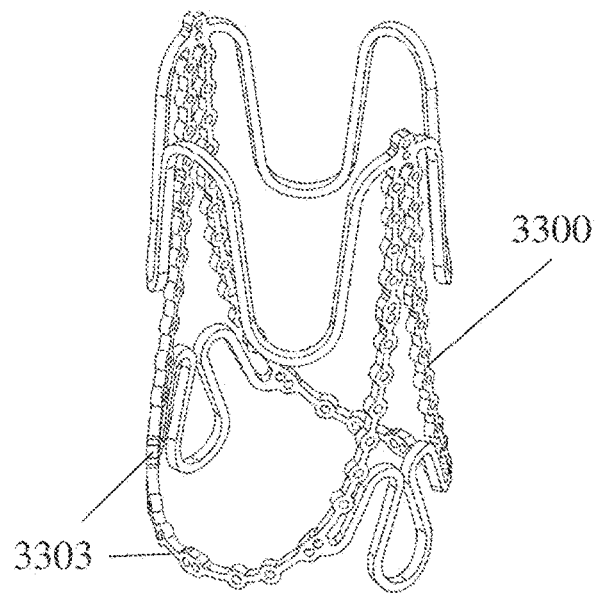
FIG. 34A is a perspective view of one embodiment of a valve frame of a valve replacement device.
Figure 34B:
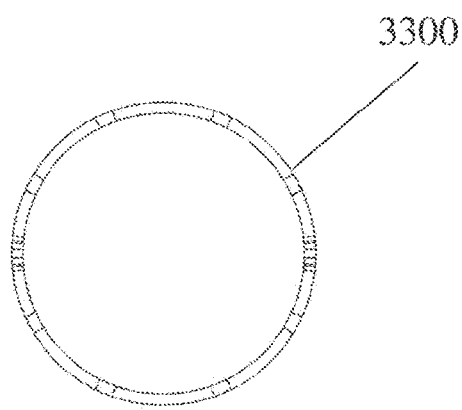
FIG. 34B is a top view of the valve frame according to the embodiment of FIG. 34A.
Figure 34C:
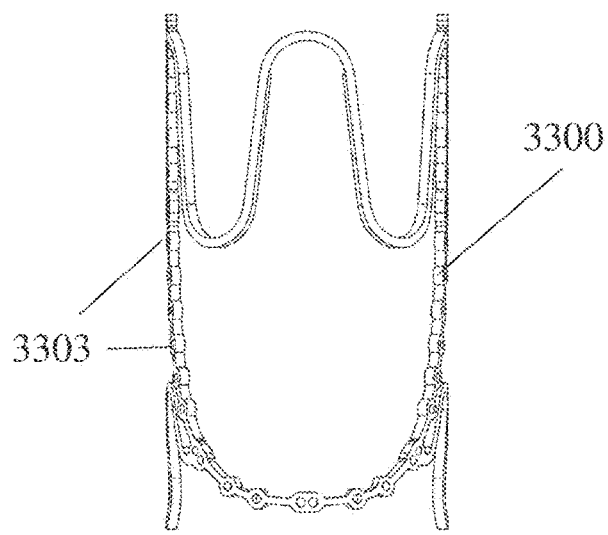
FIG. 34C is a front view of the valve frame according to the embodiment of FIG. 34A.
Figure 34D:
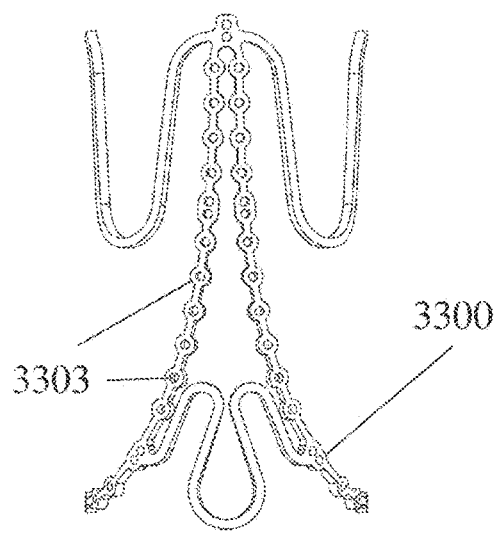
FIG. 34D is a side view of the valve frame according to the embodiment of FIG. 34A.
Figure 37A:
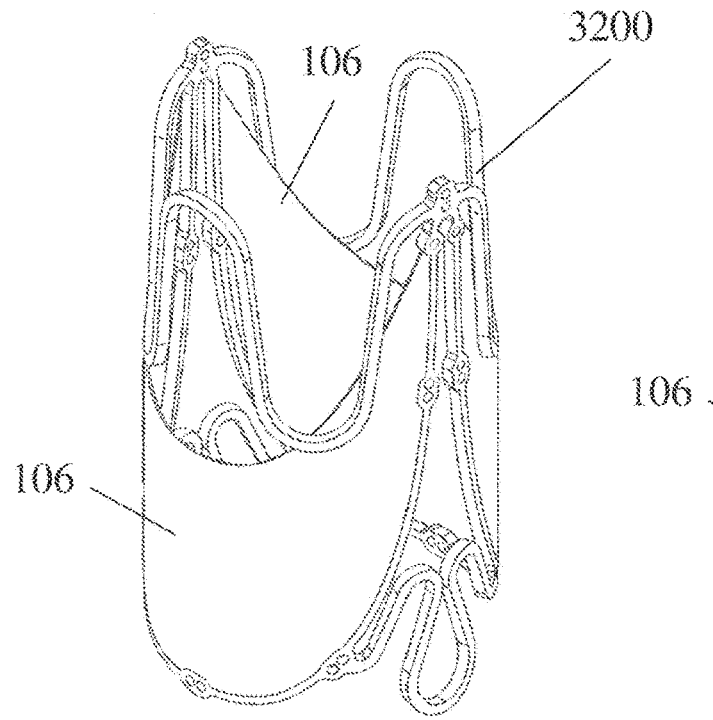
FIG. 37A is a perspective view of the valve frame of FIG. 33A with leaflets attached to the frame.
Figure 37B:
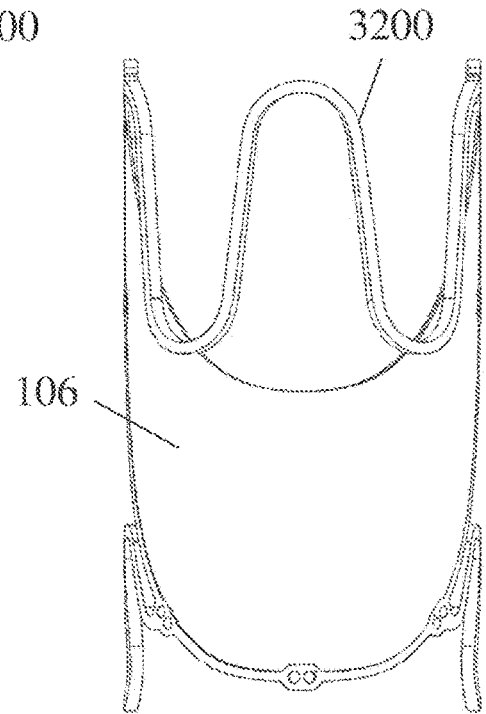
FIG. 37B is a front view of the arrangement of FIG. 37A.
Figure 37C:
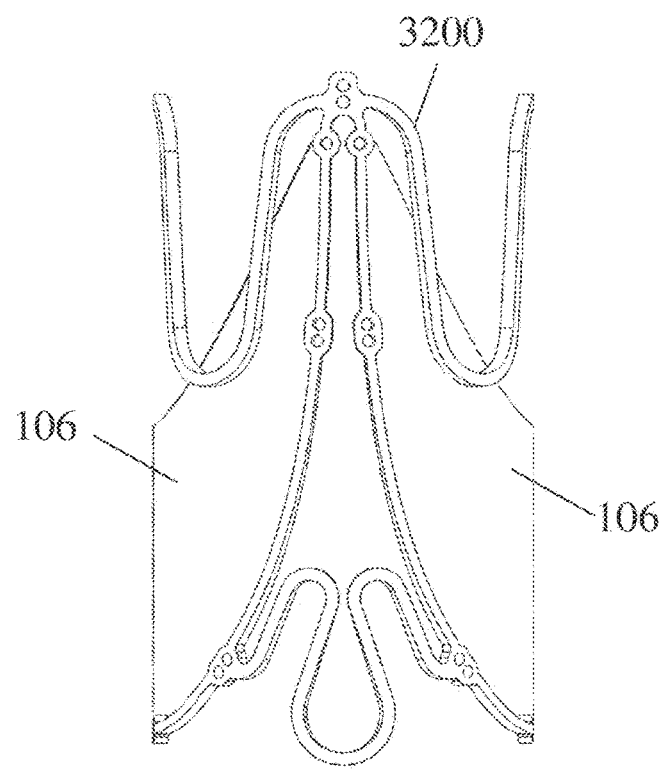
FIG. 37C is a side view of the arrangement of FIG. 37A.
Figure 38A:
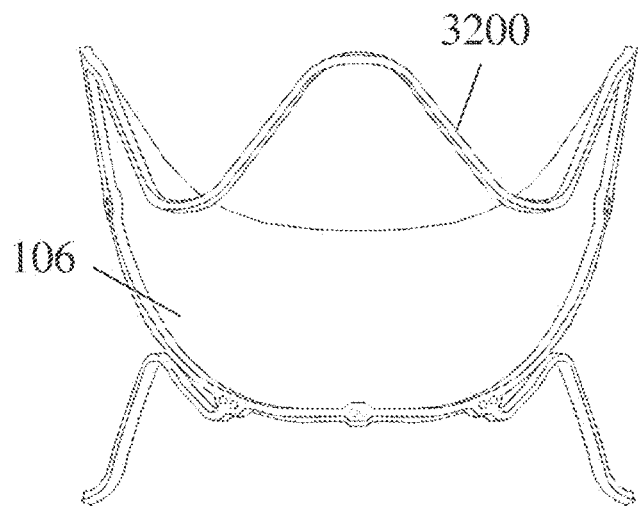
FIG. 38A is a front view of the arrangement of FIG. 37A in an expanded state.
Figure 38B:
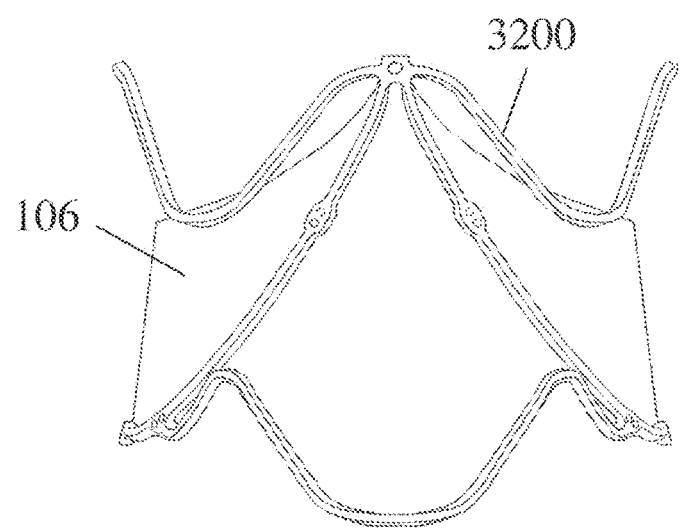
FIG. 38B is a side view of the arrangement of FIG. 37A in an expanded state.

FIGS. 37A-37C show the valve frame 3200 of the FIG. 33A embodiment attached to leaflets 106 to illustrate how leaflets may be attached to the valve frame. For the other reinforcement strut embodiments shown in FIGS. 25A, 33A, 34A, 35A, and 36A, leaflets may be attached to such valve frames in a similar orientation as shown in FIGS. 37A-37C. FIG. 38A shows a front view of the valve frame and leaflet combination of FIG. 37A in an expanded state, and FIG. 38A shows a side view of FIG. 38A.

FIGS. 39A-39D show an alternative embodiment of the valve replacement device. In this embodiment, the valve frame 3900 includes a top reinforcement strut 3904 and lower reinforcement strut 3906 connecting the lower portions of the frame sections. This embodiment is an example of how the mechanical properties and/or geometry and/or width or thickness of the frame support features can be modified to impact the expansion geometry (i.e. shape of the opening) of the valve frame 3900. In this embodiment, the top reinforcement strut 3904 has a thickness that is reduced compared to the thickness of the leaflet attachment line and the thickness of the lower reinforcement strut 3906, making it less stiff than these other frame components. Without wishing to be bound by theory, it is contemplated that these modifications result in an altered expansion profile of the device wherein the pair of commissures undergoes greater deformation in the radial direction due to being less constrained, resulting in asymmetric/non-circular widening at the upper end of the valve replacement device. The lower reinforcement strut maintains a circular opening at the base of the valve.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A valve replacement device, comprising:
   a valve frame defining an opening for passage of fluid, the opening having a diameter along a largest dimension of the opening, the valve frame being expandable to permit an increase in the diameter of the opening from 5 mm to 50 mm; and
   a first leaflet coupled to the valve frame, the first leaflet having an open configuration in which the opening is exposed, and a closed configuration in which the first leaflet at least partially covers the opening,
   wherein the valve frame is configured to expand to permit an increase in the diameter of the opening, and wherein the first leaflet is configured to be moveable between the open and closed configurations as the diameter of the opening expands from 5 mm to 50 mm,
   wherein the first leaflet maintains a constant surface area with expansion or contraction of the valve frame,
   wherein the valve frame includes first and second frame sections configured to move laterally apart from each other as the valve frame expands, and
   wherein at least one of the first and second frame sections have a curve profile defined by an elliptical quadrant projected upon a cylinder.

2. The valve replacement device of claim 1,
   further comprising a second leaflet having an open configuration in which the opening is exposed, and a closed configuration in which the first and second leaflets contact one another to at least partially cover the opening, wherein the first leaflet and second leaflets are configured to be moveable between the open and closed configurations over the diameter size range of the opening, wherein in the closed configuration, the first and second leaflets permit a regurgitant fraction of no more than 0 to 20% over a diameter size range of the opening of 5 mm to 50 mm.

3. The valve replacement device of claim 1, wherein the valve frame expands asymmetrically by expanding faster in a first lateral direction than an opposing lateral direction.

4. The valve replacement device of claim 1, wherein the valve frame expands asymmetrically by expanding further in a first lateral direction than an opposing lateral direction.

5. The valve replacement device of claim 1, wherein the opening is asymmetric.

6. The valve replacement device of claim 1,
wherein the valve frame comprises first and second frame sections connected by a pair of commissures, and
wherein the valve frame is asymmetric such that the first and second frame sections are different from one another.

7. A valve replacement device, comprising:
a valve frame defining an opening for passage of fluid, the opening having a diameter along a largest dimension of the opening, the valve frame being expandable to permit an increase in the diameter of the opening from 5 mm to 50 mm; and
a first leaflet coupled to the valve frame, the first leaflet having an open configuration in which the opening is exposed, and a closed configuration in which the first leaflet at least partially covers the opening,
wherein the valve frame is configured to expand to permit an increase in the diameter of the opening, and wherein the first leaflet is configured to be moveable between the open and closed configurations as the diameter of the opening expands from 5 mm to 50 mm,
wherein the valve frame comprises first and second frame sections connected by a pair of commissures, and
wherein the first frame section forms a U-shape having two arms extending away from an intermediate section, the intermediate section forming a base of the first frame section.

8. The valve replacement device of claim 7, wherein the intermediate section is planar.

9. The valve replacement device of claim 7, wherein the intermediate section is non-planar.

10. A valve replacement device comprising:
a valve frame defining an opening for passage of fluid, the valve frame having a diameter along a largest dimension of the opening, the valve frame having a height in a direction perpendicular to the diameter, the valve frame being expandable to increase the diameter in an operational configuration and contractible to decrease the diameter in a contracted configuration and having a height to diameter ratio ranging from 0.5:1 to 2.5:1 in the operational configuration; and
a first leaflet coupled to the frame,
wherein as the frame expands, the height decreases as the diameter increases,
wherein the valve frame includes first and second frame sections configured to move laterally apart from each other as the valve frame expands, and
wherein at least one of the first and second frame sections have a curve profile defined by an elliptical quadrant projected upon a cylinder.

11. The valve replacement device of claim 10, wherein the valve frame can expand in a length perpendicular to the diameter and preserve the height to diameter ratio at different diameters.

12. The valve replacement device of claim 1, wherein the valve frame comprises first and second frame sections connected by a pair of commissures, and
wherein at least one of the first and second frame sections have a curve profile defined by an elliptical quadrant projected upon a cylinder.

13. The valve replacement device of claim 12, wherein a center of an ellipse from which the elliptical quadrant is derived coincides with a point along a circumference of an axial end of the cylinder, and a minor axis and a major axis of the ellipse are co-axial with edges of a cross-section of the cylinder.

14. The valve replacement device of claim 10, wherein a center of an ellipse from which the elliptical quadrant is derived, coincides with a point along a circumference of an axial end of the cylinder, and a minor and major axis of the ellipse are co-axial with edges of a cross-section of the cylinder.

15. The valve replacement device of claim 1,
wherein the valve frame comprises first and second frame sections connected by a pair of commissures,
further comprising a first reinforcement feature that connects the pair of commissures,
further comprising a second reinforcement feature that connects the first and second frame sections, and
wherein the second reinforcement feature is used as a fixation site for transcatheter deployment or for fixation to native structures.

16. The valve replacement device of claim 10, wherein the valve frame includes first and second frame sections configured to move laterally apart from each other as the valve frame expands,
wherein the first and second frame sections are connected at a pair of commissures,
further comprising a first reinforcement feature that connects the pair of commissures,
and further comprising a second reinforcement feature that connects the first and second frame sections, and
wherein the second reinforcement feature is used as a fixation site for transcatheter deployment or for fixation to native structures.

17. The valve replacement device of claim 10,
wherein the valve frame includes first and second frame sections configured to move laterally apart from each other as the valve frame expands,
wherein the first and second frame sections are connected at a pair of commissures,
further comprising a first reinforcement feature that connects the pair of commissures,
further comprising a second reinforcement feature that connects the first and second frame sections, and
wherein at least one of the first and second reinforcement features is of a different shape than the other of the first and second reinforcement features.

18. The valve replacement device of claim 1,
wherein the valve frame comprises first and second frame sections connected by a pair of commissures,
further comprising a first reinforcement feature that connects the pairs of commissures,
further comprising a second reinforcement feature that connects the first and second frame sections, and
wherein at least one of the first and second reinforcement features is of a different thickness than the other of the first and second reinforcement features.

19. The valve replacement device of claim 1,
wherein the valve frame comprises first and second frame sections connected by a pair of commissures, further comprising a first reinforcement feature that connects the pairs of commissures,
further comprising a second reinforcement feature that connects the first and second frame sections, and
wherein at least one of the first and second reinforcement features is of a different shape than the other of the first and second reinforcement features.

20. A valve replacement device comprising:
a valve frame defining an opening for passage of fluid, the valve frame having a diameter along a largest dimension of the opening, the valve frame having a height in a direction perpendicular to the diameter, the valve frame being configured to expand to increase the diameter in an operational configuration and contractible to decrease the diameter in a contracted configuration and having a height to diameter ratio ranging from 0.5:1 to 2.5:1 in the operational configuration; and
a first leaflet coupled to the frame,
wherein as the frame expands, the height decreases as the diameter increases,
wherein the valve frame includes first and second frame sections configured to move laterally apart from each other as the valve frame expands,
wherein the first and second frame sections are connected at a pair of commissures,
further comprising a first reinforcement feature that connects the pair of commissures,
further comprising a second reinforcement feature that connects the first and second frame sections, and
wherein at least one of the first and second reinforcement features is of a different shape than the other of the first and second reinforcement features.

21. A valve replacement device, comprising:
a valve frame defining an opening for passage of fluid, the opening having a diameter along a largest dimension of the opening, the valve frame being expandable to permit an increase in the diameter of the opening from 5 mm to 50 mm; and
a first leaflet coupled to the valve frame, the first leaflet having an open configuration in which the opening is exposed, and a closed configuration in which the first leaflet at least partially covers the opening,
wherein the valve frame is configured to expand to permit an increase in the diameter of the opening, and wherein the first leaflet is configured to be moveable between the open and closed configurations as the diameter of the opening expands from 5 mm to 50 mm,
wherein the first leaflet maintains a constant surface area with expansion or contraction of the valve frame,
wherein the valve frame comprises first and second frame sections connected by a pair of commissures,
further comprising a first reinforcement feature that connects the pairs of commissures,
further comprising a second reinforcement feature that connects the first and second frame sections, and
wherein at least one of the first and second reinforcement features is of a different shape than the other of the first and second reinforcement features.

\* \* \* \* \*